United States Patent
Marshall et al.

(10) Patent No.: US 8,876,842 B2
(45) Date of Patent: Nov. 4, 2014

(54) MENISCAL REPAIR DEVICE

(75) Inventors: Peter Marshall, Bolton, MA (US);
Dennis Hubbard, Lancaster, MA (US)

(73) Assignee: Covidien LP, Mansfield, MA (US)

(*) Notice: Subject to any disclaimer, the term of this patent is extended or adjusted under 35 U.S.C. 154(b) by 193 days.

(21) Appl. No.: 12/724,866

(22) Filed: Mar. 16, 2010

(65) Prior Publication Data

US 2010/0228271 A1 Sep. 9, 2010

Related U.S. Application Data

(63) Continuation-in-part of application No. 11/805,223, filed on May 22, 2007, now Pat. No. 7,918,868.

(60) Provisional application No. 60/802,378, filed on May 22, 2006, provisional application No. 60/921,403, filed on Apr. 2, 2007, provisional application No. 61/165,608, filed on Apr. 1, 2009.

(51) Int. Cl.
| | | |
|---|---|---|
| *A61B 17/04* | (2006.01) | |
| *A61B 17/29* | (2006.01) | |
| *A61B 17/06* | (2006.01) | |
| *A61B 17/064* | (2006.01) | |

(52) U.S. Cl.
CPC ..... *A61B 17/0469* (2013.01); *A61B 2017/0475* (2013.01); *A61B 2017/0472* (2013.01); *A61B 17/0485* (2013.01); *A61B 2017/2923* (2013.01); *A61B 2017/06052* (2013.01); *A61B 2017/0477* (2013.01); *A61B 17/0467* (2013.01); *A61B 2017/0646* (2013.01); *A61B 17/0482* (2013.01); *A61B 2017/0474* (2013.01)
USPC .......................................................... 606/144

(58) Field of Classification Search
USPC .................................. 606/139, 144, 145, 148
See application file for complete search history.

(56) References Cited

U.S. PATENT DOCUMENTS

| | | | |
|---|---|---|---|
| 1,855,546 A | 4/1932 | File | |
| 2,012,776 A | 8/1935 | Roeder | |
| 2,880,728 A | 4/1939 | Rights | |
| 4,493,323 A * | 1/1985 | Albright et al. | ............... 606/144 |
| 4,836,205 A | 6/1989 | Barrett | |
| 4,935,027 A | 6/1990 | Yoon | |
| 4,994,074 A | 2/1991 | Bezwada et al. | |
| 5,037,433 A | 8/1991 | Wilk et al. | |

(Continued)

FOREIGN PATENT DOCUMENTS

| | | |
|---|---|---|
| DE | 290026 S | 7/1980 |
| EP | 1598017 A1 | 11/2005 |

(Continued)

OTHER PUBLICATIONS

European Search Report for corresponding EP07777216 date of mailing is Mar. 20, 2012 (8 pgs).

(Continued)

*Primary Examiner* — Dianne Dornbusch

(57) ABSTRACT

A meniscal repair device includes a handle with a thumbslide and a needle cartridge extending therefrom, the needle cartridge having distal tips having a specific directional orientation suited for a particular procedure. The meniscal repair device includes a needle rack and an obturator rack. A quantity of suture material is included in the meniscal repair device. The distal ends of the needle cartridge are adapted for penetrating soft tissue.

14 Claims, 87 Drawing Sheets

(56) References Cited

U.S. PATENT DOCUMENTS

| | | | |
|---|---|---|---|
| 5,085,661 A | 2/1992 | Moss | |
| 5,123,914 A | 6/1992 | Cope | |
| 5,250,055 A * | 10/1993 | Moore et al. | 606/148 |
| 5,281,237 A | 1/1994 | Gimpelson | |
| 5,330,488 A | 7/1994 | Goldrath | |
| 5,336,230 A | 8/1994 | Leichtling et al. | |
| 5,336,231 A | 8/1994 | Adair | |
| 5,364,410 A | 11/1994 | Failla et al. | |
| 5,391,182 A | 2/1995 | Chin | |
| 5,423,844 A | 6/1995 | Miller | |
| 5,458,609 A | 10/1995 | Gordon et al. | |
| 5,462,560 A * | 10/1995 | Stevens | 606/144 |
| 5,499,991 A | 3/1996 | Garman et al. | |
| 5,501,691 A | 3/1996 | Goldrath | |
| 5,531,699 A | 7/1996 | Tomba et al. | |
| 5,544,664 A | 8/1996 | Benderev et al. | |
| 5,562,684 A | 10/1996 | Kammerer | |
| 5,569,269 A | 10/1996 | Hart et al. | |
| 5,573,542 A | 11/1996 | Stevens | |
| 5,601,571 A | 2/1997 | Moss | |
| 5,611,515 A | 3/1997 | Benderev et al. | |
| 5,620,012 A | 4/1997 | Benderev et al. | |
| 5,653,716 A | 8/1997 | Malo | |
| 5,665,096 A | 9/1997 | Yoon | |
| 5,681,333 A | 10/1997 | Burkhart | |
| 5,722,981 A * | 3/1998 | Stevens | 606/148 |
| 5,741,278 A | 4/1998 | Stevens | |
| 5,749,884 A | 5/1998 | Benderev et al. | |
| 5,776,150 A | 7/1998 | Nolan et al. | |
| 5,782,845 A | 7/1998 | Shewchuk | |
| 5,797,928 A | 8/1998 | Kogasaka | |
| RE36,020 E | 12/1998 | Moore et al. | |
| 5,842,478 A | 12/1998 | Benderev et al. | |
| 5,895,395 A * | 4/1999 | Yeung | 606/144 |
| 5,897,563 A | 4/1999 | Yoon | |
| 5,921,993 A | 7/1999 | Yoon | |
| 5,938,668 A | 8/1999 | Scirica et al. | |
| 5,941,439 A | 8/1999 | Kammerer et al. | |
| 5,954,732 A | 9/1999 | Hart et al. | |
| 6,022,360 A | 2/2000 | Reimels | |
| 6,045,571 A | 4/2000 | Hill et al. | |
| 6,047,826 A | 4/2000 | Kalinski et al. | |
| 6,059,800 A | 5/2000 | Hart et al. | |
| 6,066,146 A | 5/2000 | Carroll et al. | |
| 6,071,289 A | 6/2000 | Stefanchik et al. | |
| 6,110,183 A | 8/2000 | Cope | |
| 6,113,610 A | 9/2000 | Poncet | |
| RE36,974 E | 11/2000 | Bonutti | |
| 6,171,317 B1 | 1/2001 | Jackson et al. | |
| 6,206,895 B1 | 3/2001 | Levinson | |
| 6,293,961 B2 | 9/2001 | Schwartz et al. | |
| 6,306,159 B1 | 10/2001 | Schwartz et al. | |
| 6,319,271 B1 | 11/2001 | Schwartz et al. | |
| 6,443,963 B1 | 9/2002 | Baldwin et al. | |
| 6,451,024 B1 | 9/2002 | Thompson et al. | |
| 6,491,707 B2 | 12/2002 | Makower et al. | |
| 6,500,184 B1 | 12/2002 | Chan et al. | |
| 6,524,317 B1 | 2/2003 | Ritchart | |
| 6,533,795 B1 | 3/2003 | Tran et al. | |
| 6,605,096 B1 | 8/2003 | Ritchart | |
| 6,638,286 B1 * | 10/2003 | Burbank et al. | 606/157 |
| 6,679,895 B1 | 1/2004 | Sancoff et al. | |
| 6,699,263 B2 | 3/2004 | Cope | |
| 6,770,084 B1 | 8/2004 | Bain et al. | |
| 6,893,448 B2 | 5/2005 | O'Quinn et al. | |
| 6,932,824 B1 | 8/2005 | Roop et al. | |
| 6,972,027 B2 | 12/2005 | Fallin et al. | |
| 6,984,237 B2 | 1/2006 | Hatch et al. | |
| 6,988,985 B2 | 1/2006 | Suzuki et al. | |
| 7,090,690 B2 | 8/2006 | Foerster et al. | |
| 7,118,583 B2 | 10/2006 | O'Quinn et al. | |
| 7,141,057 B2 | 11/2006 | Burbank et al. | |
| 7,153,312 B1 | 12/2006 | Torrie et al. | |
| 7,156,857 B2 | 1/2007 | Pasricha et al. | |
| 7,166,116 B2 | 1/2007 | Lizardi et al. | |
| 7,211,093 B2 | 5/2007 | Sauer et a | |
| 7,232,447 B2 | 6/2007 | Gellman et al. | |
| 7,232,448 B2 | 6/2007 | Battles et al. | |
| 7,306,613 B2 | 12/2007 | Kawashima et al. | |
| 7,320,693 B2 | 1/2008 | Pollack et al. | |
| 7,390,328 B2 | 6/2008 | Modesitt | |
| 7,449,024 B2 | 11/2008 | Stafford | |
| 2004/0039442 A1 | 2/2004 | St. Goar et al. | |
| 2004/0122473 A1 | 6/2004 | Ewers et al. | |
| 2004/0249395 A1 | 12/2004 | Mikkaichi et al. | |
| 2005/0021055 A1 | 1/2005 | Toubia et al. | |
| 2005/0043746 A1 | 2/2005 | Pollak et al. | |
| 2006/0069398 A1 | 3/2006 | Suzuki et al. | |
| 2006/0241658 A1 | 10/2006 | Cerundolo | |
| 2007/0118153 A1 | 5/2007 | Funamura et al. | |
| 2007/0179509 A1 | 8/2007 | Nagata et al. | |
| 2007/0282351 A1 | 12/2007 | Harada et al. | |
| 2008/0114380 A1 | 5/2008 | Takemoto et al. | |
| 2008/0140092 A1 | 6/2008 | Stone et al. | |
| 2008/0140094 A1 | 6/2008 | Schwartz et al. | |
| 2008/0177288 A1 | 7/2008 | Carlson | |
| 2008/0228204 A1 | 9/2008 | Hamilton et al. | |
| 2008/0243147 A1 | 10/2008 | Hamilton et al. | |
| 2008/0243148 A1 | 10/2008 | Mikkaichi et al. | |
| 2008/0255591 A1 | 10/2008 | Harada et al. | |
| 2008/0269783 A1 | 10/2008 | Griffith | |

FOREIGN PATENT DOCUMENTS

| | | |
|---|---|---|
| JP | 4226643 | 8/1992 |
| JP | 05-161655 | 6/1993 |
| JP | 06-024533 B | 4/1994 |
| JP | 07-328020 | 12/1995 |
| JP | 2003-159254 | 6/2003 |
| JP | 3331215 B | 8/2003 |
| JP | 2004-041733 | 2/2004 |
| JP | 2006025932 | 2/2006 |
| JP | 2006025933 | 2/2006 |
| JP | 2006025934 | 2/2006 |
| JP | 08-252257 | 10/2008 |
| WO | WO 95/22932 | 8/1995 |
| WO | WO02/22026 A1 | 3/2002 |
| WO | WO 2004/006782 | 1/2004 |
| WO | WO 2006/037639 | 4/2006 |
| WO | WO 2006/082810 | 8/2006 |
| WO | WO 2007/139785 | 12/2007 |

OTHER PUBLICATIONS

Canadian Office Action dated Mar. 27, 2014 in Canadian Application No. 2,652,512.

Australian Patent Examination Report dated Mar. 12, 2013 in Australian Appln. No. 2010201249.

Japanese Office Action dated Dec. 5, 2013 in Japanese Appln. No. 2010-079777.

* cited by examiner

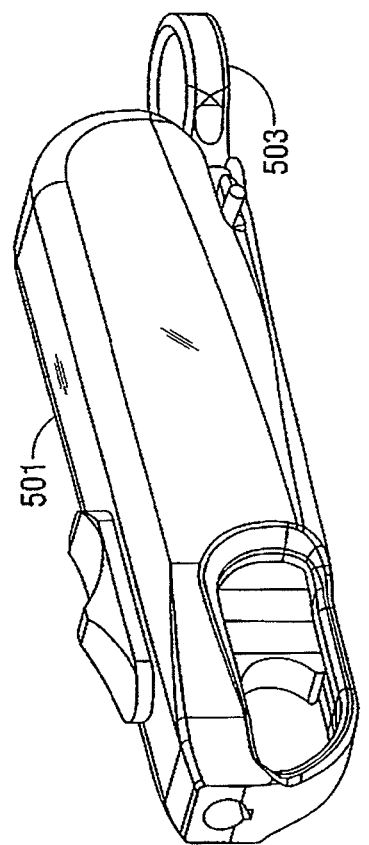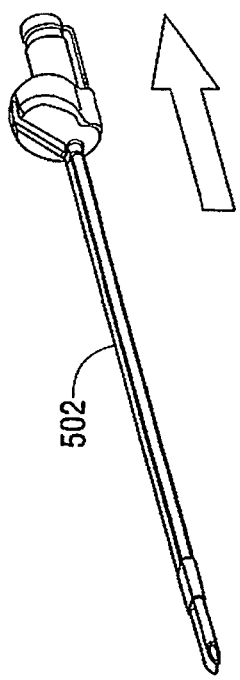
FIG. 98

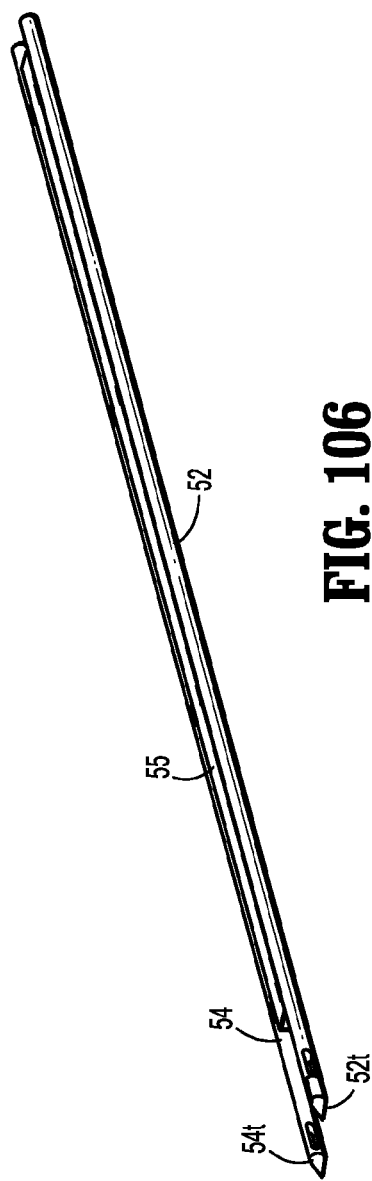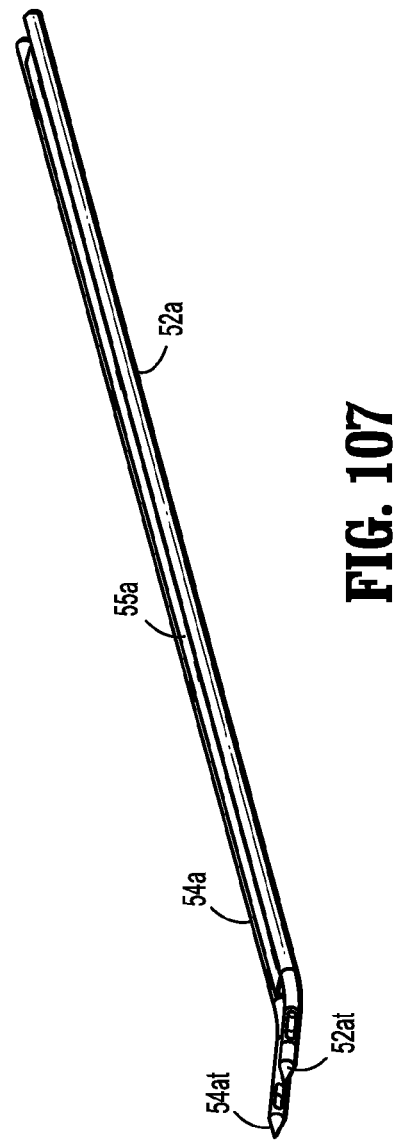

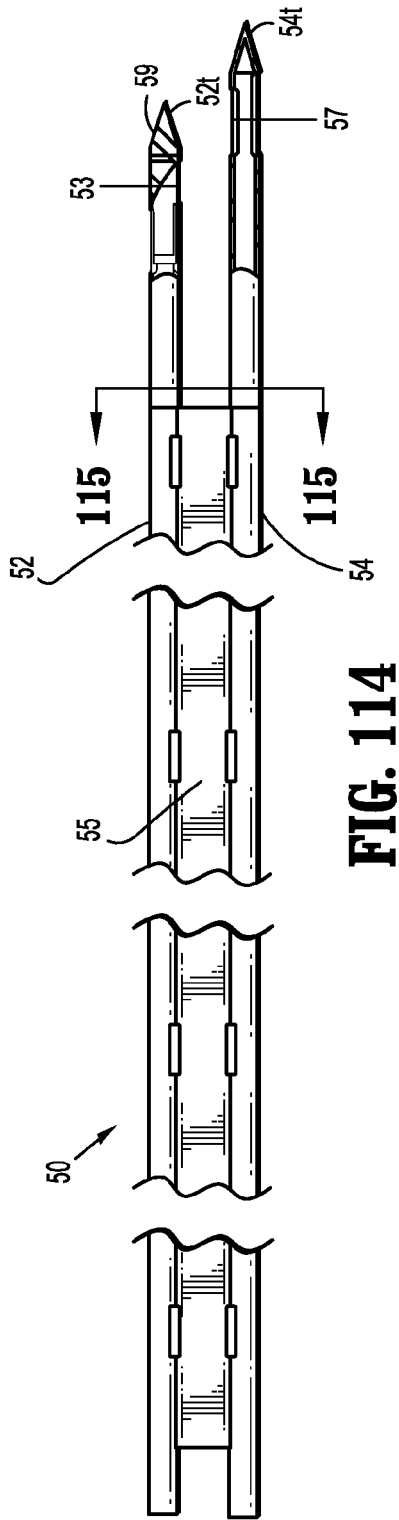
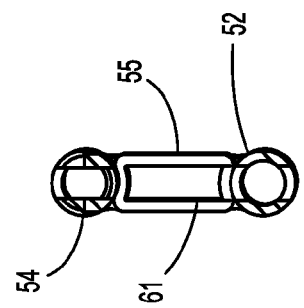
FIG. 114
FIG. 115

MENISCAL REPAIR DEVICE

CROSS-REFERENCE TO RELATED APPLICATIONS

This application claims the benefit and priority to U.S. Provisional Patent Application No. 61/165,608, filed Apr. 1, 2009, and is a continuation-in-part of U.S. patent application Ser. No. 11/805,223, filed May 22, 2007, now U.S. Pat. No. 7,918,868, which claims the benefit and priority to U.S. Provisional Patent Application No. 60/802,378, filed May 22, 2006, and U.S. Provisional Patent Application No. 60/921,403, filed Apr. 2, 2007, the entire contents of each of which are incorporated herein by reference.

BACKGROUND

1. Technical Field

The present disclosure relates to surgical methods and apparatus in general, and more particularly to surgical methods and apparatus for the repair of the meniscus.

2. Background of Related Art

The knee has two C-shaped pieces of cartilage called the lateral meniscus and the medial meniscus. They help disperse friction in the knee joint between the femur (thighbone) and the tibia (shinbone). Once a meniscus is torn, it no longer functions as it should and either needs to be repaired or removed. Since the meniscus has a very poor blood supply, it is unlikely that a damaged meniscus would be able to undergo a normal healing process. Since removal of the meniscus increases the risk of osteoarthritis, it is preferable to repair the meniscus when possible.

One method of repairing a damaged meniscus involves arthroscopic surgery. The goal of the surgery is to securely hold the damaged tissue together long enough to facilitate healing. This is accomplished by threading long needles into the meniscus and out an incision in the back. Suture threads are tied together on the outside of the knee to bring the tear together. By utilizing specially designed devices employing multiple sutures and knot pusher instruments, surgeons can repair a meniscus while making a relatively small incision.

SUMMARY

The current disclosure describes an apparatus for approximating soft tissues for repairing meniscal tear injuries. The apparatus may be a disposable suture passing instrument that is pre-loaded with a length of suture material having a pre-formed knot at a first end that, in use, is passed through the meniscus surrounding a tear and is passed from a suture feed needle to a suture catch needle.

The apparatus may include a housing and a needle assembly disposed at a distal end of the housing. The needle assembly may be releasably secured to the distal end of the housing. The needle assembly may include a first needle, e.g., a suture feed needle, including a lumen defined therein, and having first member, e.g., a shape memory needle, and second member, e.g., an ejector wire, disposed within the lumen of the first needle. The needle assembly may also include a second needle, e.g., a suture catch needle, including a lumen defined therein, and having a third member, e.g., an obturator, disposed within the lumen of the second needle. The distal ends of the first and second needles may be configured and adapted to penetrate tissue.

A length of suture material may be loaded into and retrained within the first member, and the second member may be adapted and configured to eject the length of suture material from within the first member. The third member disposed within the second window may be adapted and configured to engage a length of suture and to frictionally secure the length of suture within a window defined within an outer surface of the second needle.

An actuator may be slidably coupled to the housing along a longitudinal axis of the housing. Distal movement of the actuator along the longitudinal axis of the housing urges the first and second members through the first needle, and urges the third member through the second needle. For example, in response to the distal movement of the actuator, the first and second members may move distally through the first needle, and the third member may move proximally through the second needle. In addition, the second member may be disposed within the first member, and the first member may travel a first distance and the second member may travel a second distance, the second distance being different from the first distance.

A method of repairing a meniscal tear may include the steps of: providing a meniscal repair device including a first needle and a second needle, passing the first needle including a length of suture material at least partially through a tissue, moving the first needle along with the suture material closer to the second needle, securing the suture material to the second needle, and withdrawing the meniscal repair device from the tissue, thereby forming a loop passing at least partially through the tissue.

These and other embodiments of the present disclosure will be described in greater detail below with reference to the appended figures.

BRIEF DESCRIPTION OF THE DRAWINGS

FIGS. 92-103 are a series of views showing a fifth method and apparatus for repairing a meniscal tear;

FIG. 106 is a perspective view of a needle cartridge having a straight tip;

FIG. 107 is a perspective view of a needle cartridge having a curved tip;

FIG. 114 is a top view of the needle cartridge of FIG. 106 with the distal tips shown in cross-section;

FIG. 115 is an end cross-sectional view of the needle cartridge of FIG. 114 taken along section line 115-115;

DETAILED DESCRIPTION

Figure 1:
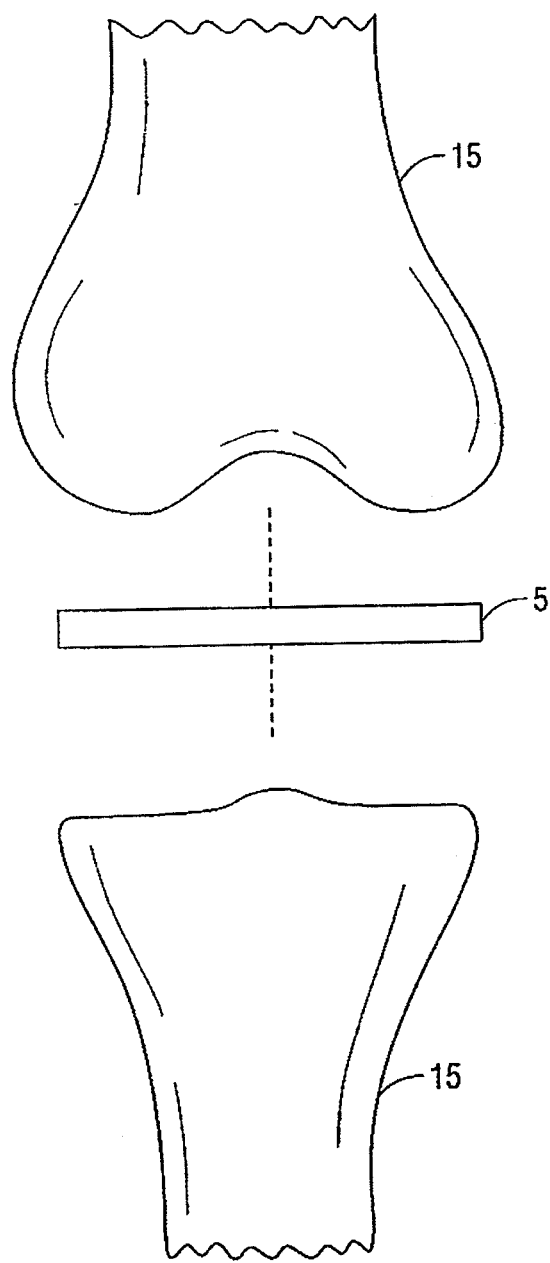
FIG. 1 is a schematic front view of a knee joint.
Figure 2:
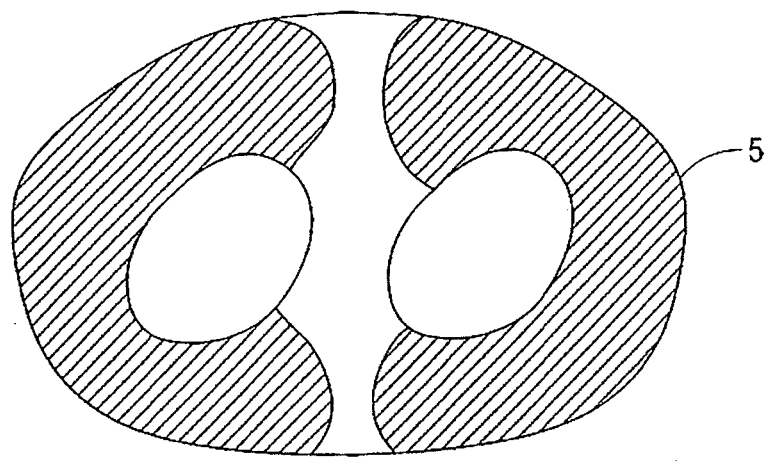
FIG. 2 is a schematic top view, in cross-section, of the meniscus of the knee joint.
Figure 3:
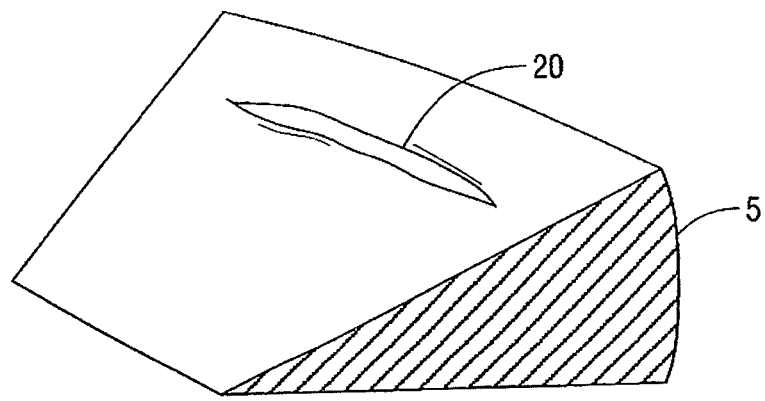
FIG. 3 is a schematic perspective view, in partial section, of the meniscus of the knee joint.

Particular embodiments of the present disclosure will be described herein with reference to the accompanying drawings. In the following description, well-known functions or constructions are not described in detail to avoid obscuring the present disclosure in unnecessary detail. As shown in the drawings and as described throughout the following descriptions, and as is traditional when referring to relative positioning on an object, the term "proximal" refers to the end of the apparatus that is closer to the user and the term "distal" refers to the end of the apparatus that is further from the user.

First Preferred Method and Apparatus

Figure 4:
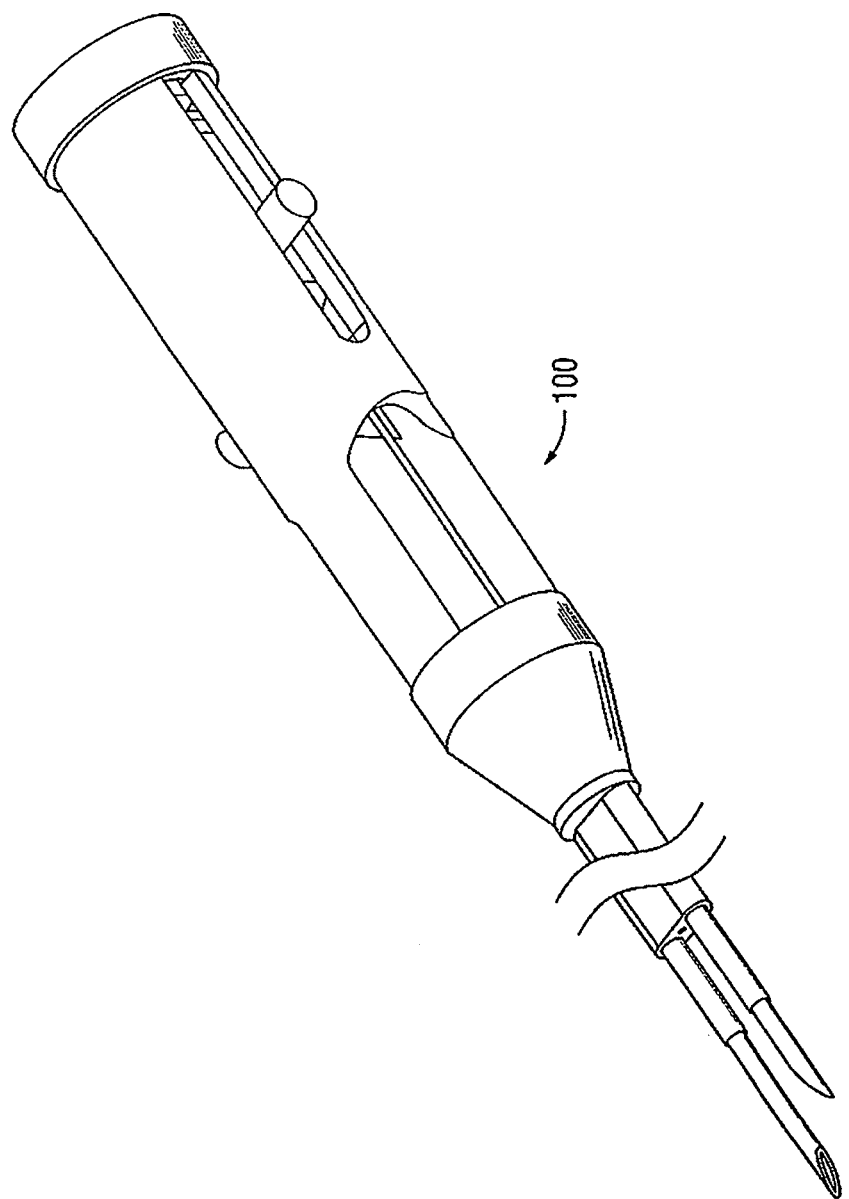
FIGS. 4-16 are a series of views showing a first method and apparatus for repairing a meniscal tear.
Figure 5:
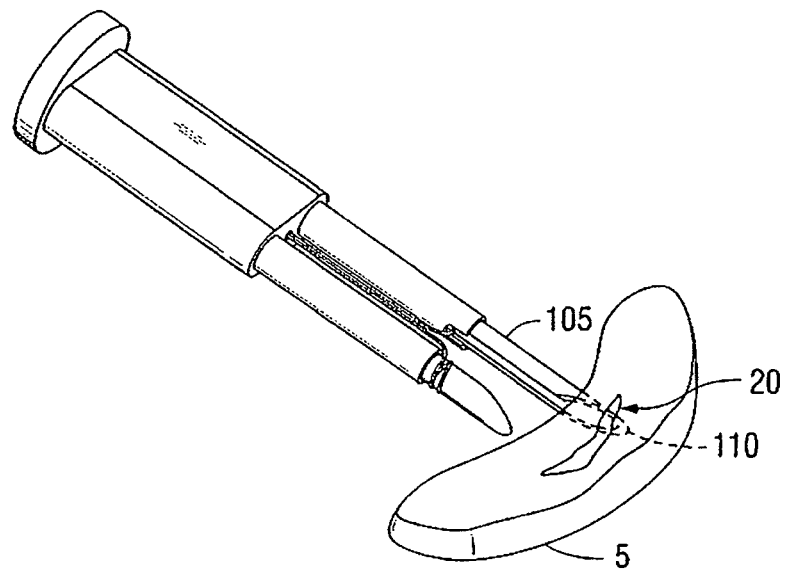

Looking first at FIGS. 4 and 5, there is shown an apparatus 100 for use in closing tear 20 in meniscus 5.

More particularly, in one preferred form of the present invention, and still looking now at FIGS. 4 and 5, a first needle 105 is first advanced so that its distal tip 110 is positioned within, but not completely through, meniscus 5.

Figure 6:
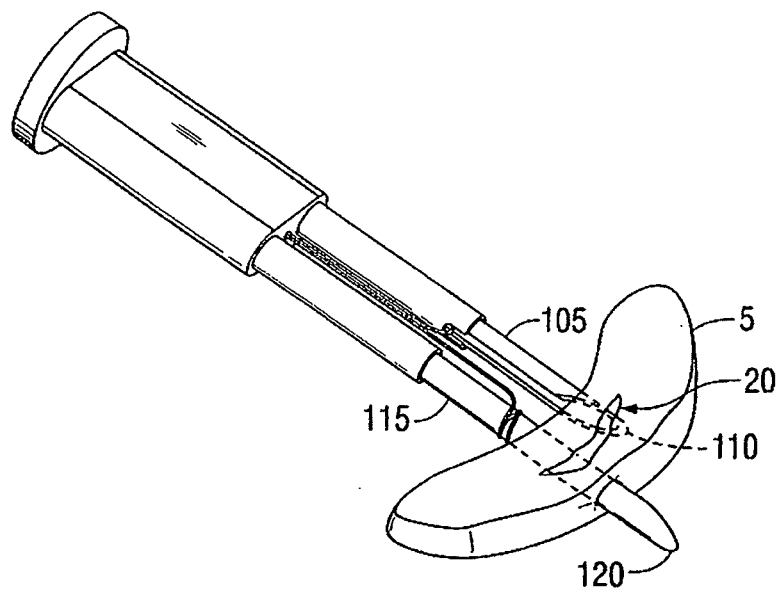

Next, as seen in FIG. 6, a second needle 115 is advanced completely through the meniscus, so that the distal tip 120 of second needle 115 is positioned on the far side of the meniscus.

Figure 7:
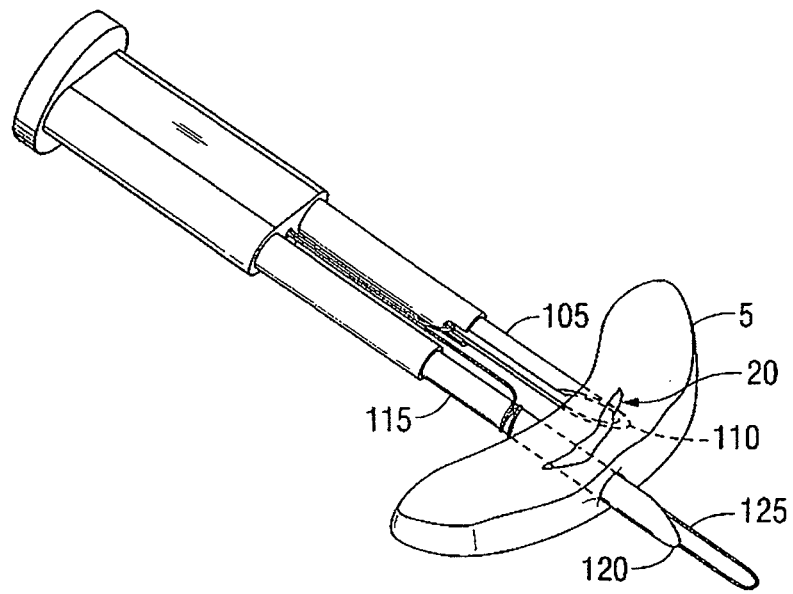
Figure 8:
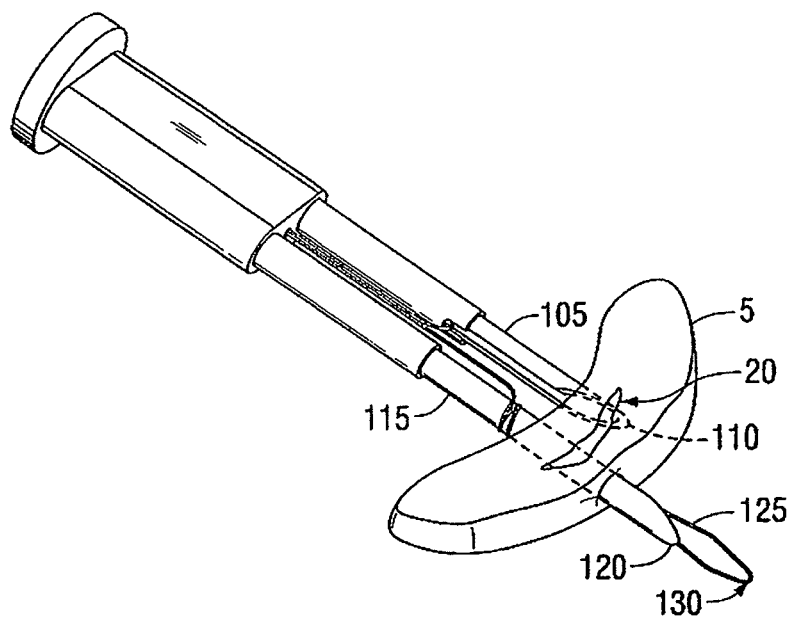
Figure 9:
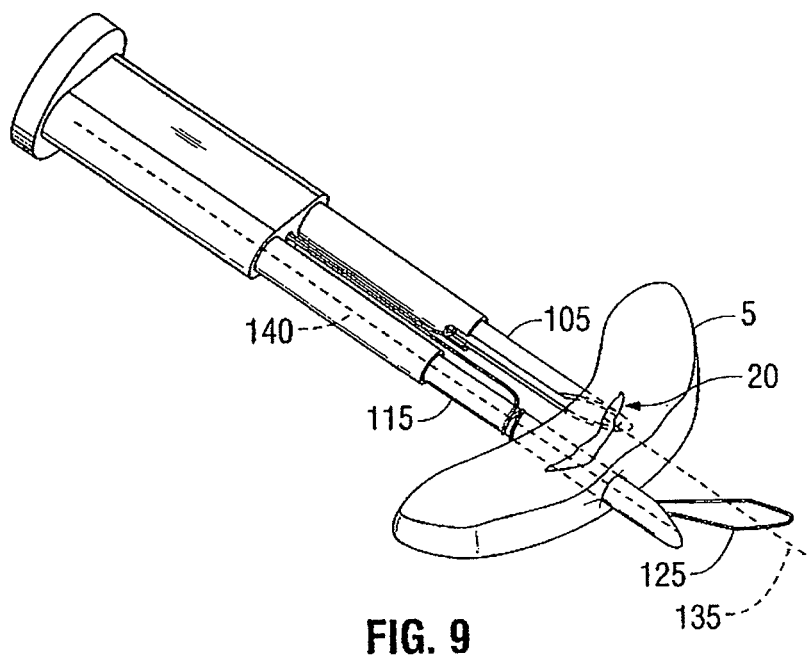

Then, and looking now at FIGS. 7-9, a snare 125 is advanced out the distal end 120 of second needle 115. Snare 125 is formed and arranged so that when the snare is in its fully-extended position (FIG. 9), the loop 130 of snare 125 is axially aligned with the longitudinal axis 135 of first needle 105. To this end, snare 125 may comprise an elongated body 140 having the loop 130 set at its distal end, with loop 130 being set at an angle to the longitudinal axis of elongated body 140. At least one of loop 130 and elongated body 140 comprises a resilient material, in order that loop 130 and elongated body 140 may be (i) received within second needle 115, and (ii) loop 130 may project across the longitudinal axis 135 of first needle 105 when snare 125 is in its fully-extended position (FIG. 9).

Figure 10:
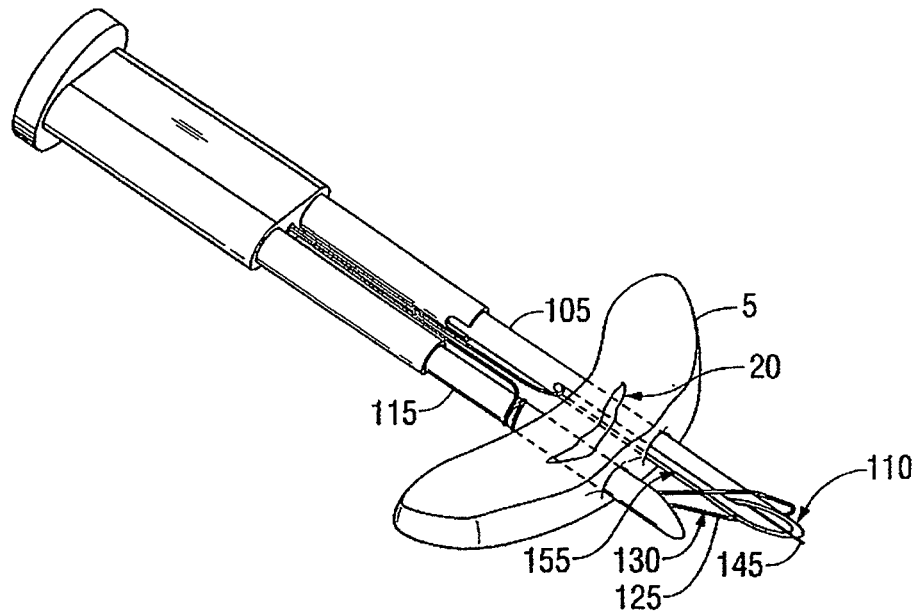

Next, and looking now at FIG. 10, first needle 105 is advanced completely through meniscus 5, so that the distal end 110 of first needle 105 extends through loop 130 of snare 125. Then first needle 105 is used to advance a suture 145 through loop 130 of snare 125. This may be affected in a variety of ways.

Figure 11:
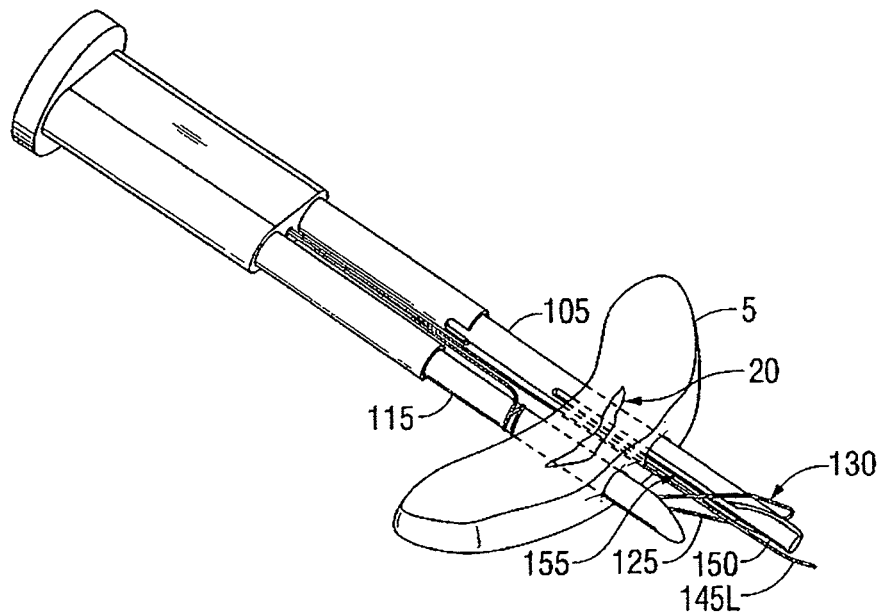
Figure 12:
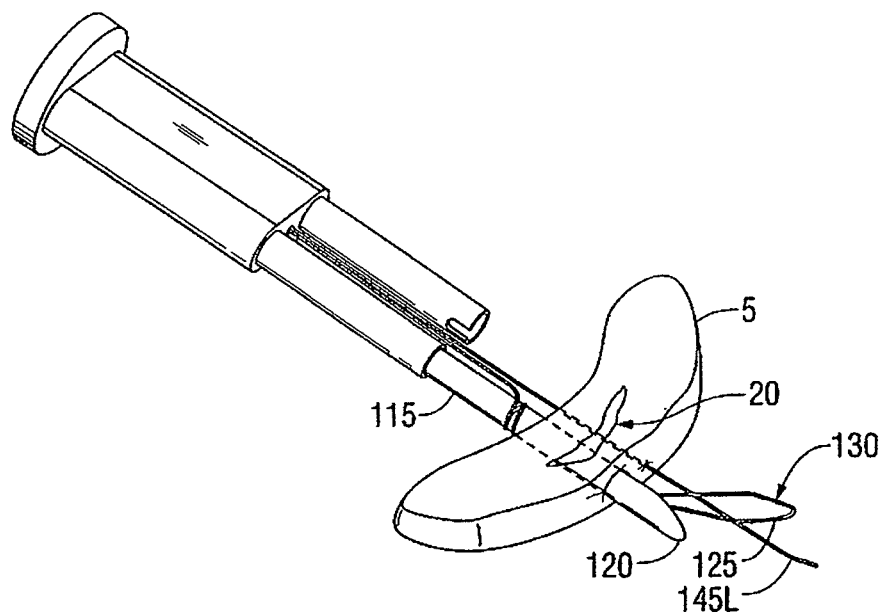

By way of example but not limitation, and looking now at FIGS. 10-12, suture 145 may be pre-disposed within first needle 105 so that suture 145 is carried through the meniscus and through loop 130 of snare 125 with the advancement of first needle 105. Then a driver 150 may be used to eject the leading portion 145L (FIG. 11) of suture 145 from the interior of first needle 105. To this end, a slot 155 may be provided in first needle 105 to assist in ejecting leading portion 145L of suture 145 from first needle 105. Finally first needle 105 is withdrawn, leaving leading portion 145L of suture 145 extending through (i) meniscus 5, and (ii) loop 130 of snare 125. The approach shown in FIGS. 10-12 can be advantageous in many circumstances, since it works well with both braided suture and monofilament suture. In this respect it will be appreciated that braided suture is generally preferable for meniscal repairs, since it tends to form a smaller knot which is less susceptible to slipping.

In an alternative approach, where suture 145 has sufficient column strength (e.g., where suture 145 comprises relatively thick monofilament suture), after first needle 105 is advanced through meniscus 5 (FIG. 10) and through loop 130 of snare 125, the suture can be pushed through first needle 105 so that leading portion 145L of suture 145 extends through both meniscus 5 and loop 130 of snare 125. Then, while suture 145 is maintained in place, first needle 105 can be withdrawn, with the column strength of the suture ensuring that leading portion 145L of suture 145 does not retreat from its position extending through meniscus 5 and loop 130 of snare 125. Of course, this latter approach does suffer from the disadvantage that it requires the use of suture with sufficient column strength (e.g., monofilament suture) and hence this approach can be difficult to practice with conventional braided suture.

Figure 13:
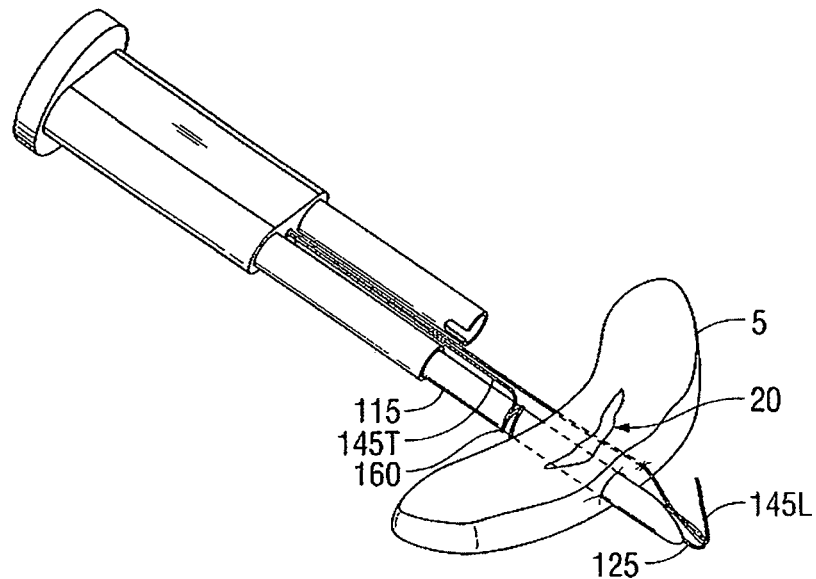
Figure 14:
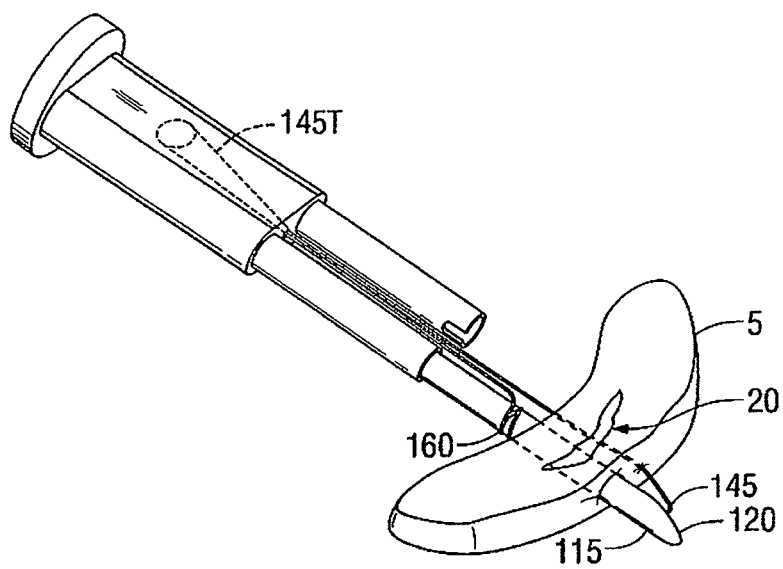
Figure 15:
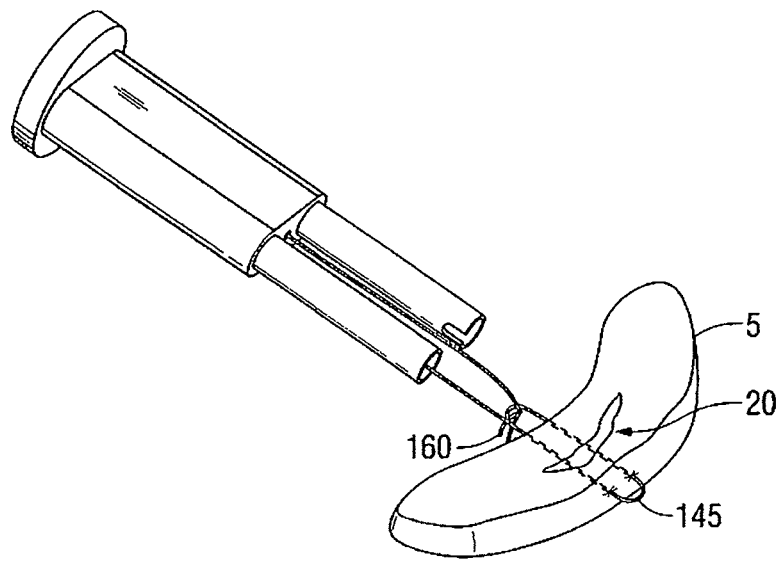

Regardless of the particular approach used to achieve the position shown in FIG. 12, once this position has been achieved, the next step is to carry leading portion 145L of suture 145 back to the near side of the meniscus. More particularly, and looking now at FIGS. 13-15, snare 125 is retracted back into second needle 115, and then second needle 115 is withdrawn back through the meniscus, carrying leading portion 145L of suture 145 with it.

Thus, at this point in the procedure, suture 145 will have been passed from the near side of the meniscus, across the meniscus and then back again. Significantly, by appropriately positioning the first needle 105 and second needle 115 during the suture passing operation, the suture will extend across the tear 20 formed in meniscus 5.

Next, the suture is tied down so as to close the tear in the meniscus. This may be done in a variety of ways which will be apparent to those skilled in the art in view of the present disclosure. However, in one preferred form of the invention, a trailing portion 145T of suture 145 may be arranged in the form of a pre-formed, uncinched knot 160 disposed about the exterior of second needle 115 (see, for example, FIGS. 13 and 14), with an intermediate portion 145I of suture 145 being disposed within apparatus 100. As a result of this construction, when snare 125 and second needle 115 carry leading portion 145L of suture 145 back through the meniscus, they will also carry leading portion 145L of suture 145 back through pre-formed, uncinched knot 160 (FIG. 15), which is itself formed from trailing portion 145T of that same suture 145. It will be appreciated that, as second needle 115 is withdrawn, pre-formed, uncinched knot 160 will slip off the end of second needle 115, into direct contact with leading portion 145L of suture 145, as the suture passes back through itself.

Figure 16:
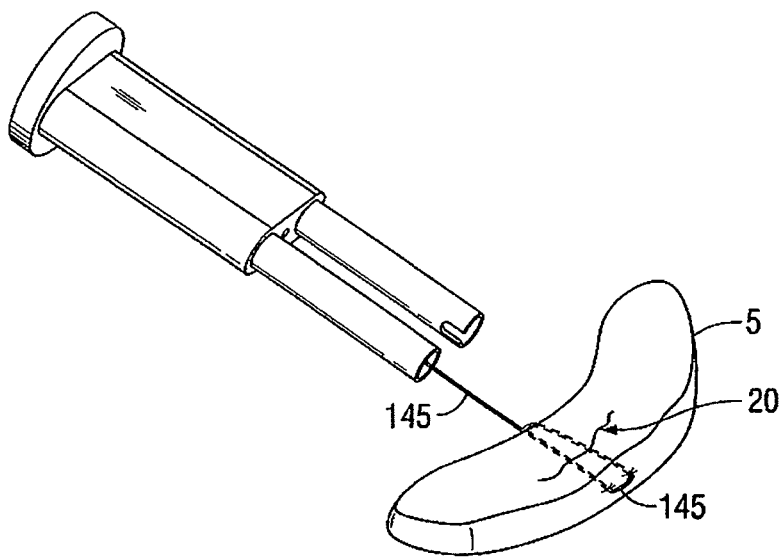

Then, and looking now at FIG. 16, suture 145 is pulled taut so as to simultaneously (i) pull tear 20 closed, and (ii) tighten pre-formed knot 160 onto the suture, whereby to fix the suture in position and thereby close tear 20 in meniscus 5. The trailing end 145T of suture 145 can then be trimmed away in ways well known in the art, thereby leaving a low-profile suture fixation within the meniscus.

Second Preferred Method and Apparatus

Figure 17:
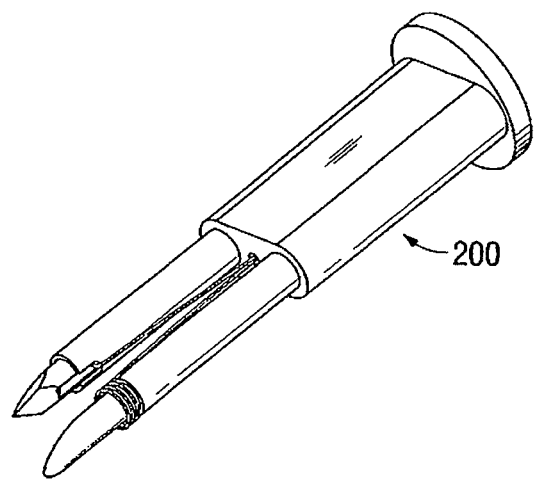
FIGS. 17-30 are a series of views showing a second method and apparatus for repairing a meniscal tear.
Figure 18:
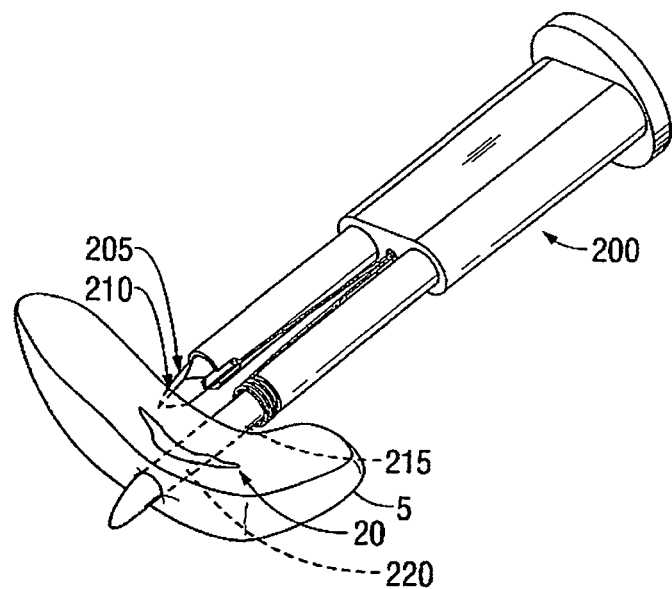

Looking now at FIGS. 17 and 18, there is shown an apparatus 200 for use in closing tear 20 in meniscus 5.

More particularly, in one preferred form of the invention, and still looking now at FIGS. 17 and 18, a first needle 205 is first advanced so that its distal tip 210 is positioned within, but not completely through, meniscus 5.

Figure 19:
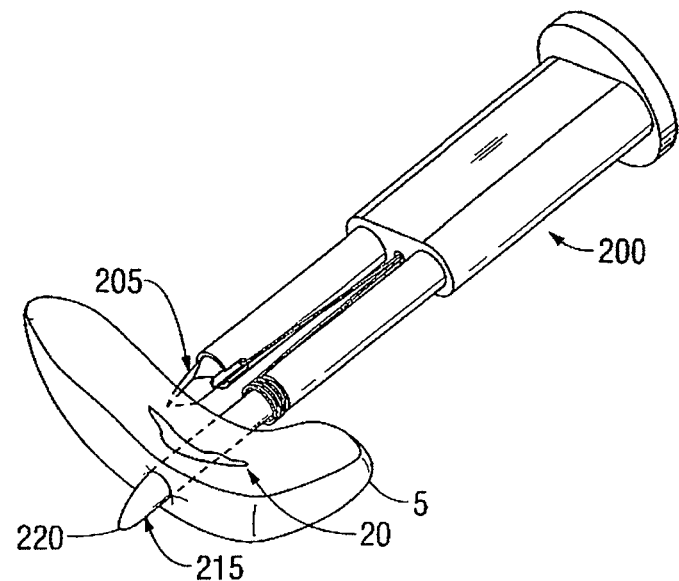
Figure 20:
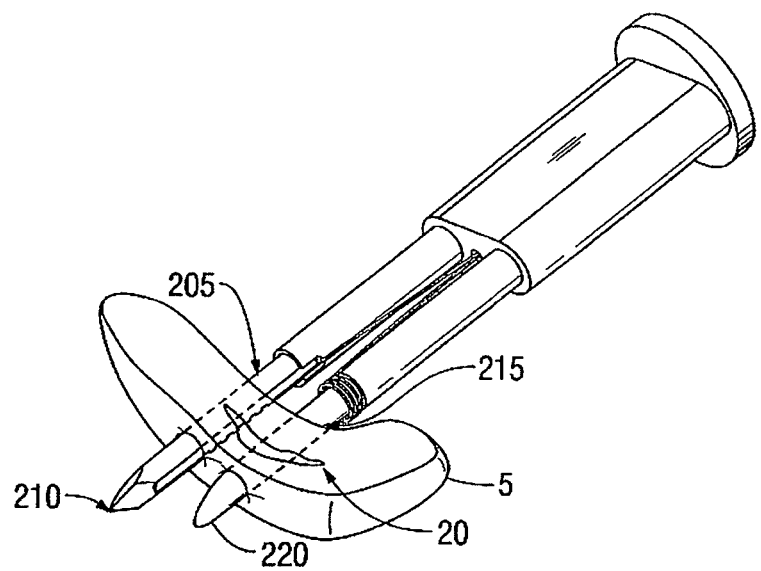

Next, as seen as FIG. 19, a second needle 215 is advanced completely through the meniscus, so that the distal tip 220 of second needle 215 lies on the far side of the meniscus. Then, and looking now at FIG. 20, first needle 205 is advanced all the way across meniscus 5.

Figure 21:
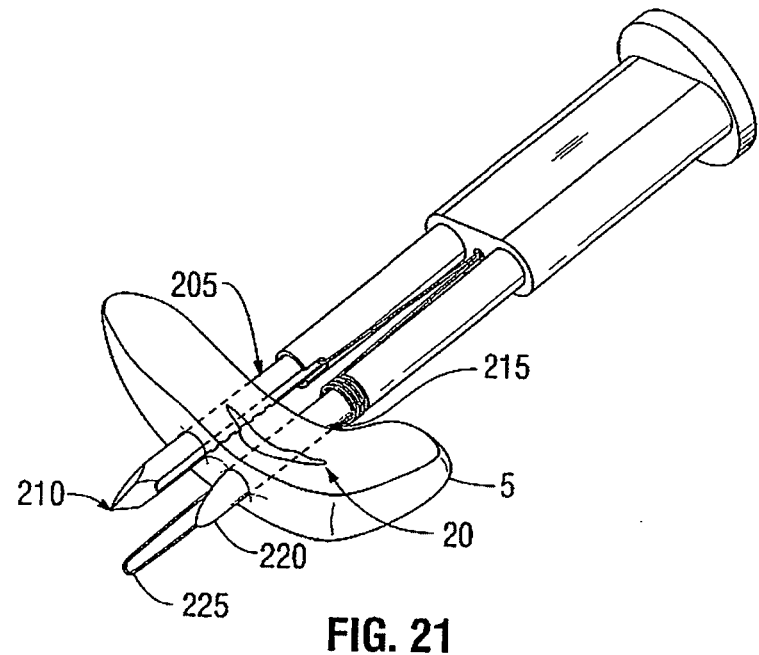
Figure 22:
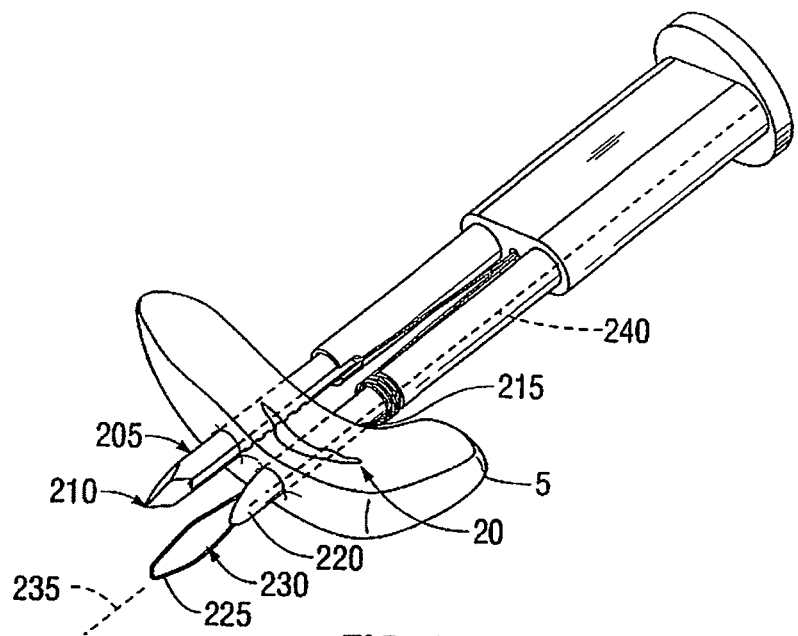

Then, and looking now at FIGS. 21 and 22, a snare 225 is advanced out the distal end 220 of second needle 215. Snare 225 is formed and arranged so that when the snare is in its fully-extended position (FIG. 22), the loop 230 of snare 225 is axially aligned with the longitudinal axis 235 of second needle 215. To this end, snare 225 may comprise an elongated body 240 having loop 230 set at its distal end, with loop 230 being aligned with the longitudinal axis of elongated body 240.

Figure 23:
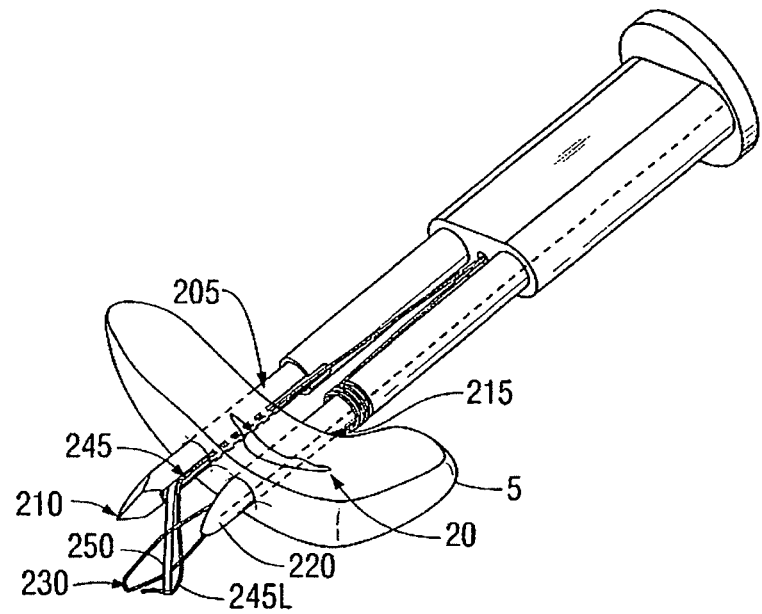

Next, and looking now at FIG. 23, a suture holder 250 carrying a suture 245 is advanced out the distal end 210 of first needle 205. Suture holder 250 is configured so that the suture holder will carry the leading portion 245L of suture 245 through loop 230 of snare 225 when the suture holder is extended out of first needle 205.

Figure 24:
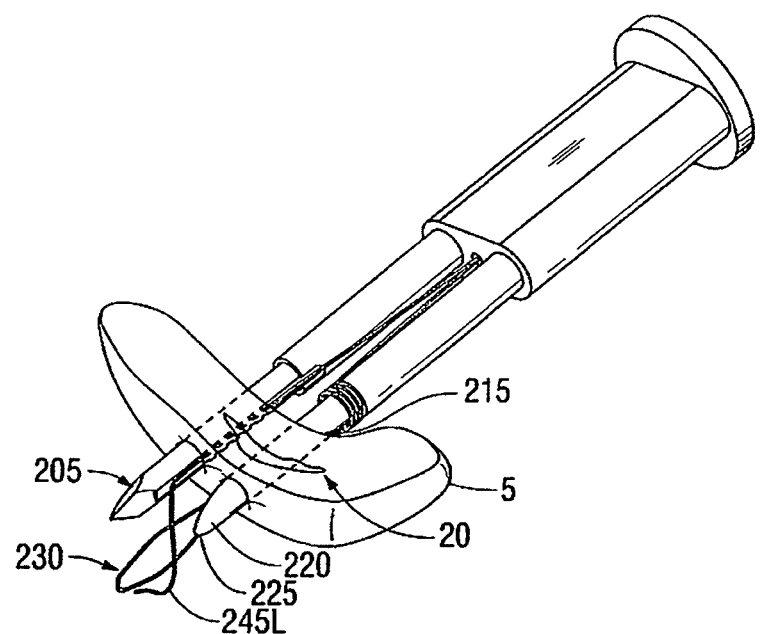
Figure 25:
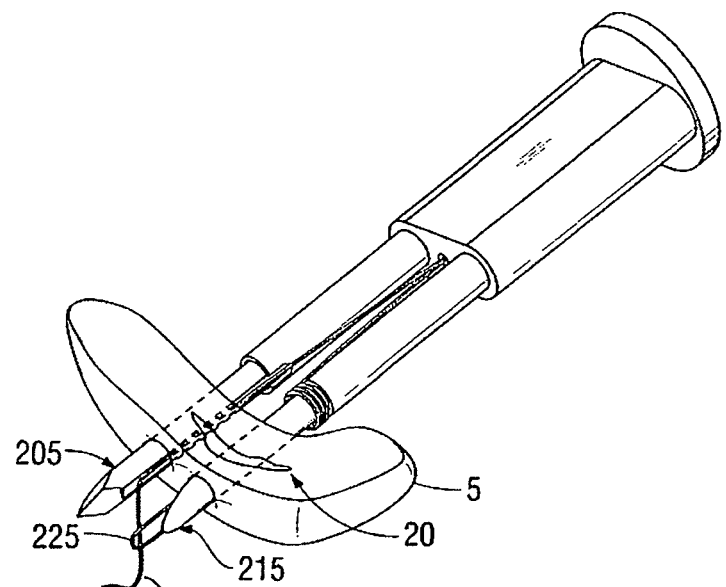
Figure 26:
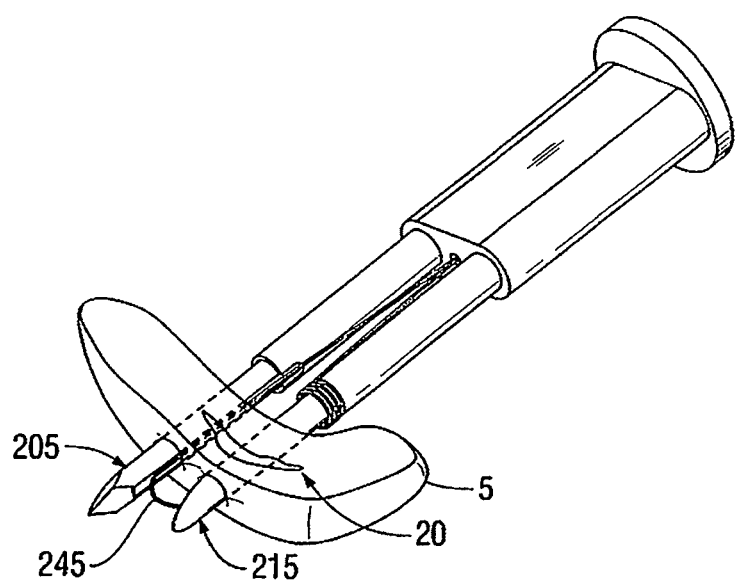
Figure 27:
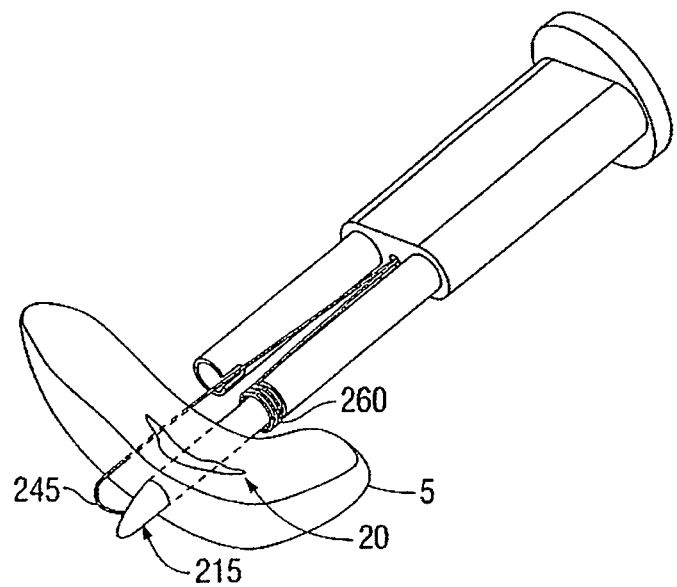
Figure 28:
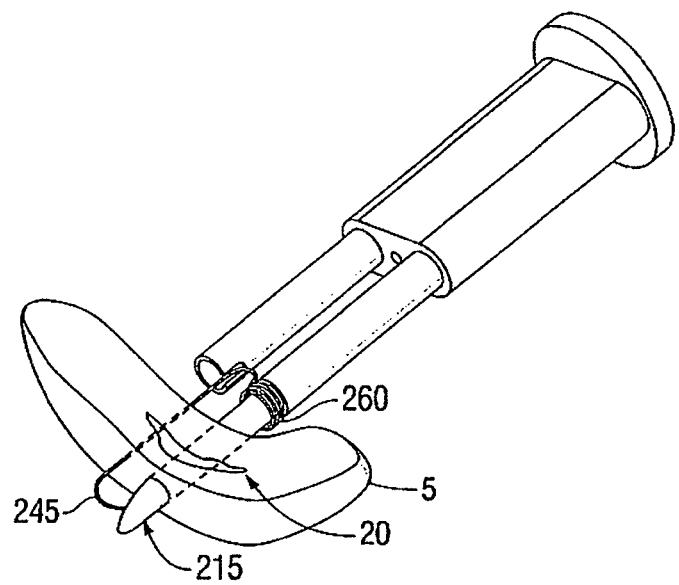
Figure 29:
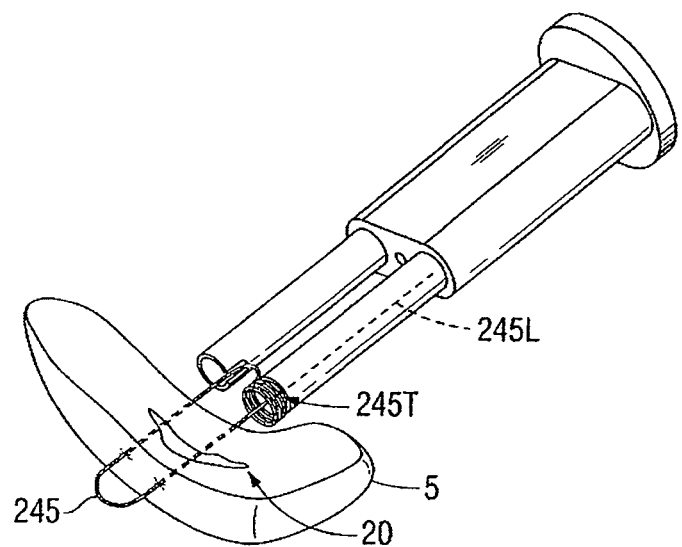

Then suture holder 250 is withdrawn, leaving the leading portion 245L of suture 245 extending though loop 230 of snare 225 (FIG. 24).

Next, leading portion 245L of suture 245 is carried back to the near side of the meniscus. More particularly, and looking now at FIGS. 25-29, snare 225 is retracted back into second needle 215, second needle 215 is withdrawn back through the meniscus, and then first needle 205 is withdrawn back through the meniscus.

Thus, at this point in the procedure, suture 245 will have been passed from the near side of the meniscus, through the meniscus and then back again. Significantly, by appropriately positioning first needle 205 and second needle 215 during the suture passing operation, suture 245 will extend across tear 20 formed in meniscus 5.

Next, the suture is tied down so as to close the tear in the meniscus. This may be done in a variety of ways which will be apparent to those skilled in the art in view of the present disclosure. However, in one preferred form of the invention, the trailing portion 245T of suture 245 may be arranged in the form of a pre-formed, uncinched knot 260 disposed about the exterior of second needle 215 (see, for example, FIG. 28) so that when snare 225 and second needle 215 carry leading portion 245L of suture 245 back through the meniscus, they will also carry leading portion 245L of suture 245 back through pre-formed, uncinched knot 260 (FIG. 29), which is formed by trailing portion 245T of suture 245. It will be appreciated that, as second needle 215 is withdrawn, pre-formed, uncinched knot 260 will slip off the end of second needle 215, into direct contact with leading portion 245L of suture 245, as the suture passes back through itself.

Figure 30:
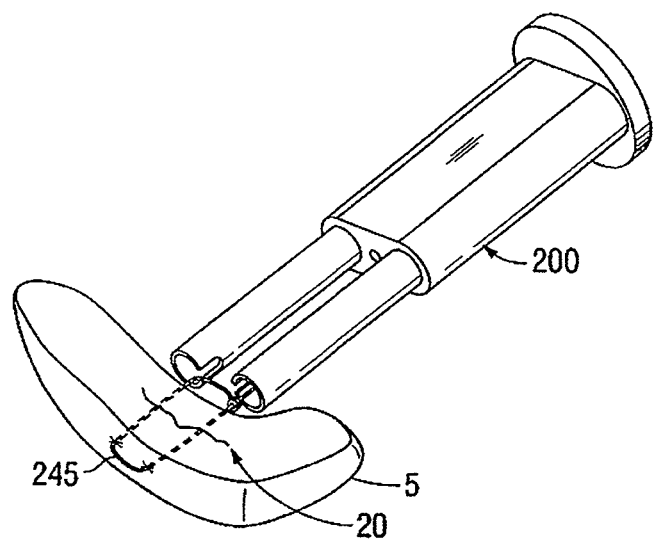
Figure 31:
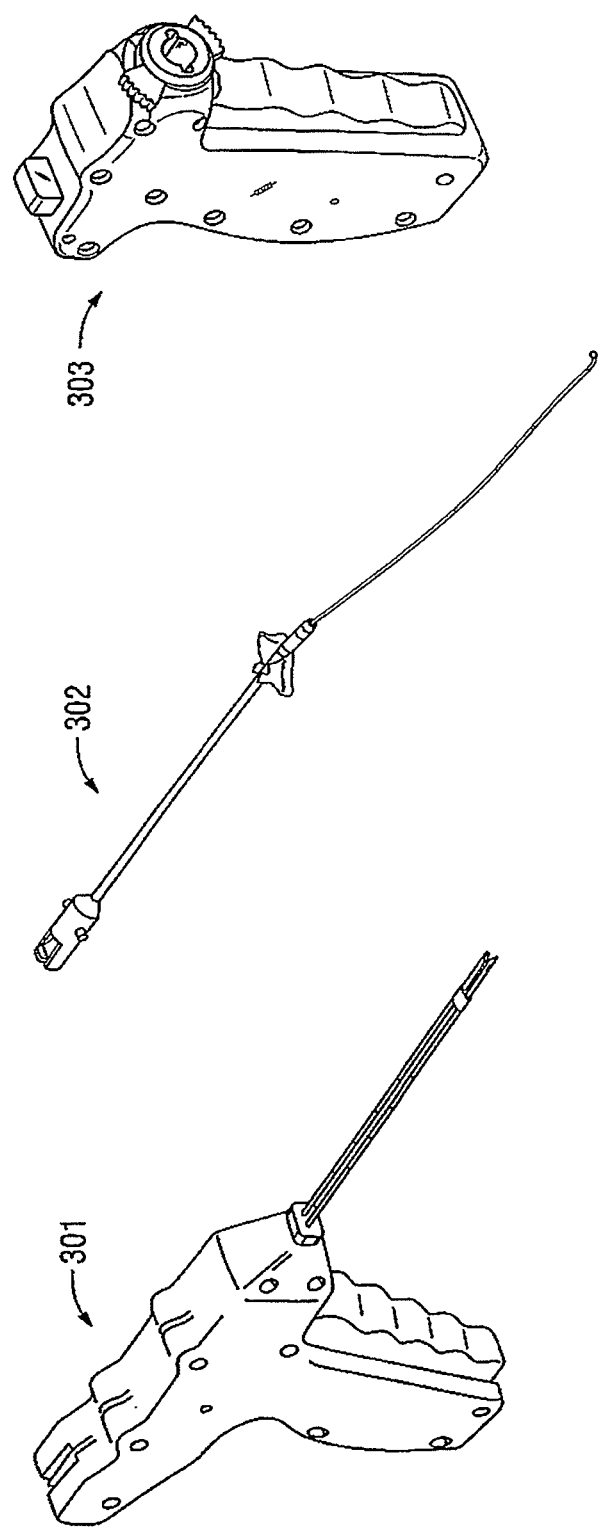
FIGS. 31-65 are a series of views showing a third method and apparatus for repairing a meniscal tear, with the meniscus being omitted from selected views in order to simplify the drawing and enhance comprehension.
Figure 32:
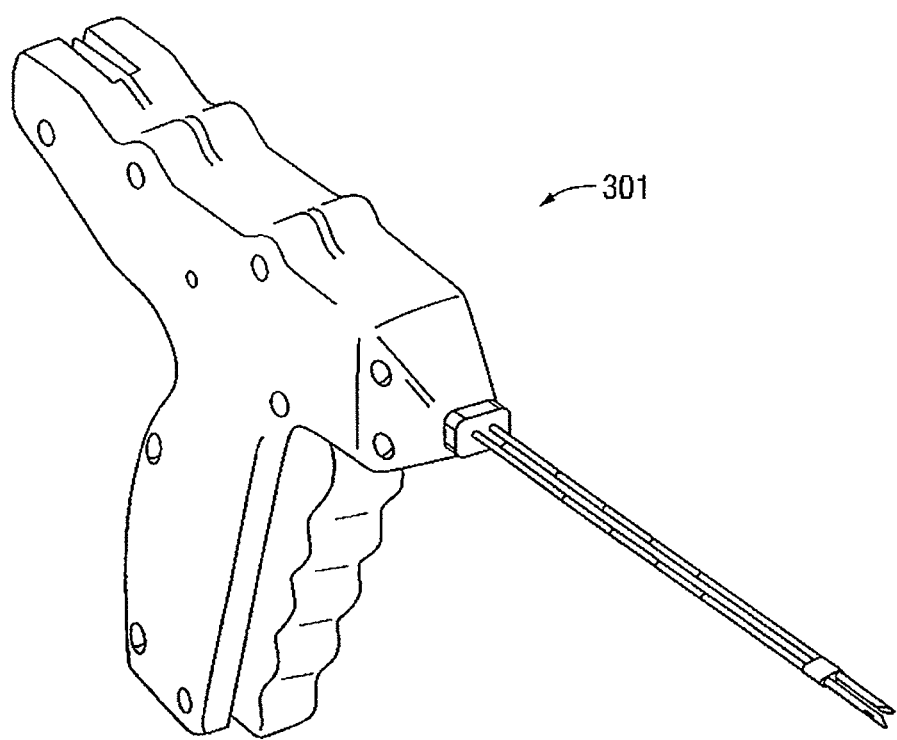
Figure 33:
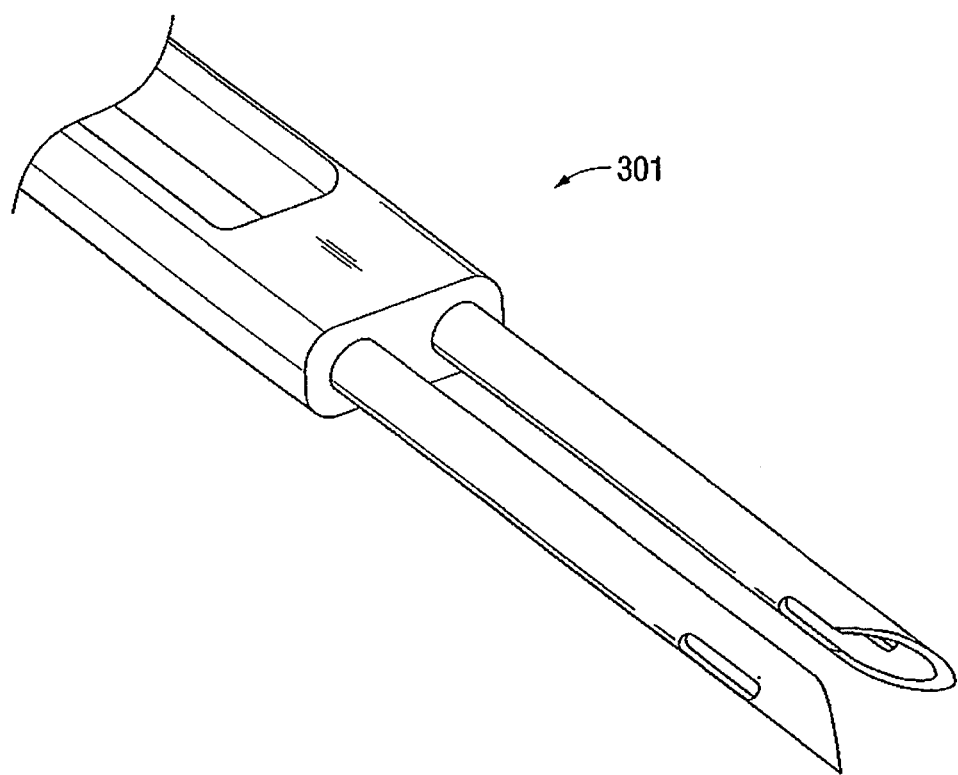
Figure 34:
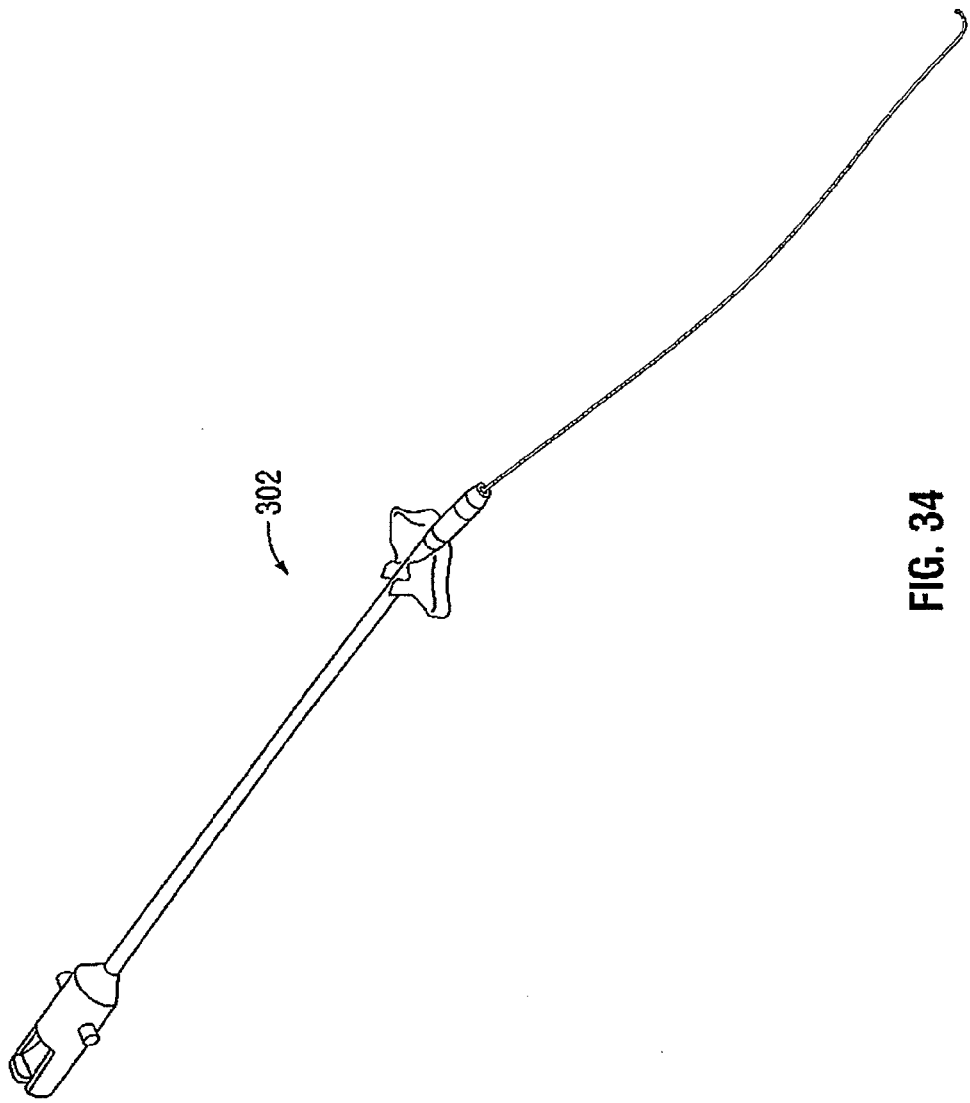

Then, and looking now at FIG. 30, trailing portion 245T of suture 245 is pulled taut so as to simultaneously (i) pull tear 20 closed, and (ii) tighten pre-formed knot 260 onto the suture, whereby to fix the suture in position and thereby close tear 20 in meniscus 5. The trailing end 245T of suture 245 can then be trimmed away in ways well known in the art, thereby leaving a low-profile suture fixation within the meniscus.

Third Preferred Method and Apparatus

Figure 35:
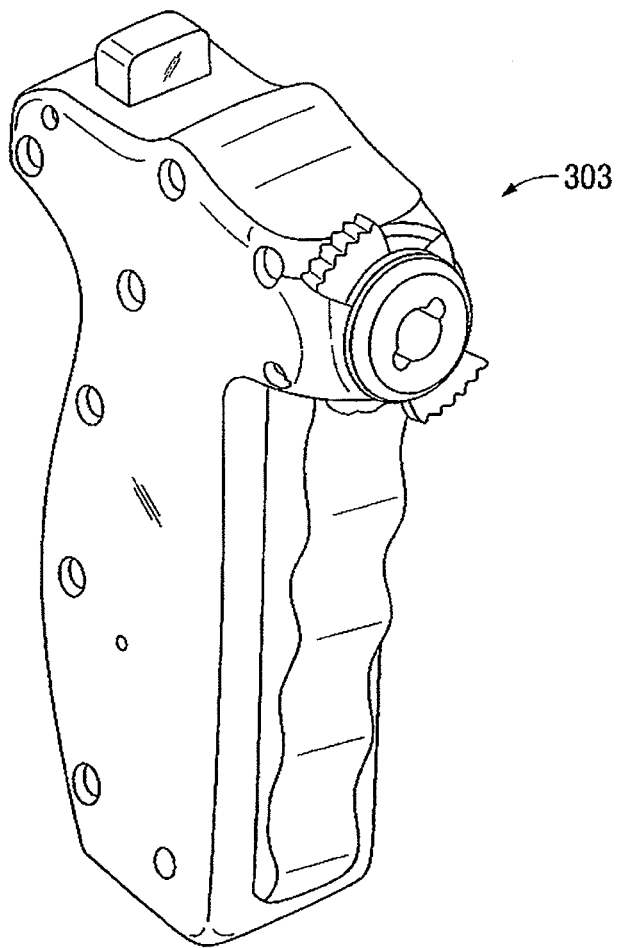
Figure 36:
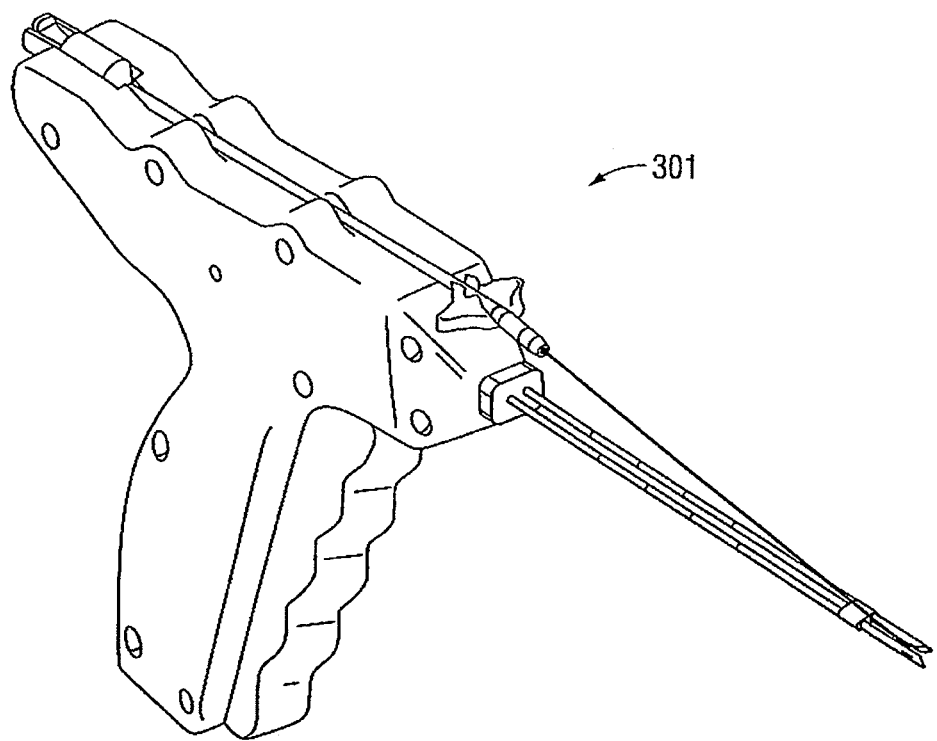
Figure 37:
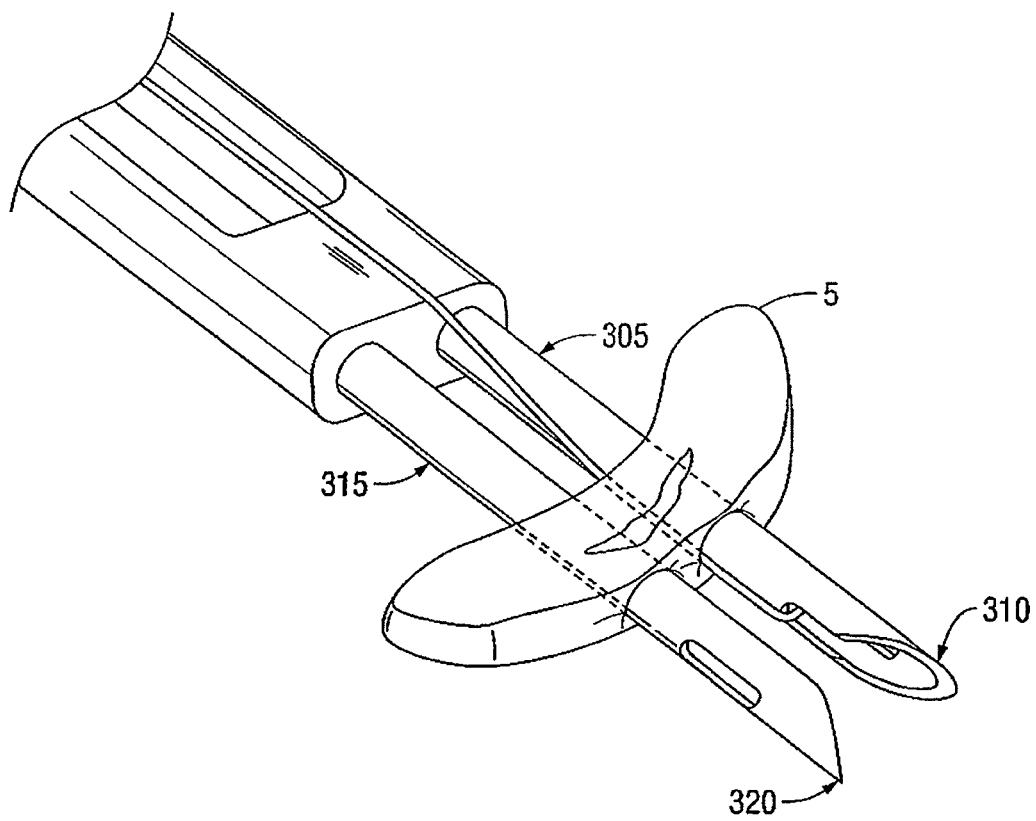

Looking now at FIGS. 31-35, there is shown an apparatus 300 for use in closing tear 20 in meniscus 5. Apparatus 300 generally comprises a suture passer 301 (FIGS. 31-33), a suture cartridge 302 (FIG. 34) and a knot pusher/cutter 303 (FIG. 35). Specific details of the construction and function of suture passer 301, suture cartridge 302 and knot pusher/cutter 303 will be disclosed in the course of the following discussion of using apparatus 300 to close tear 20 in meniscus 5.

Figure 38:
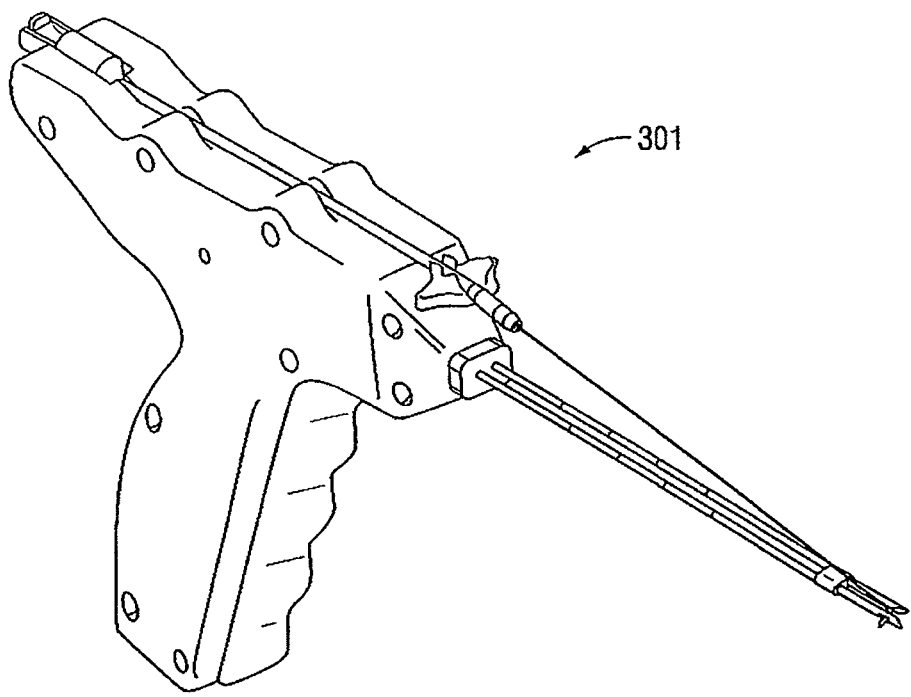
Figure 39:
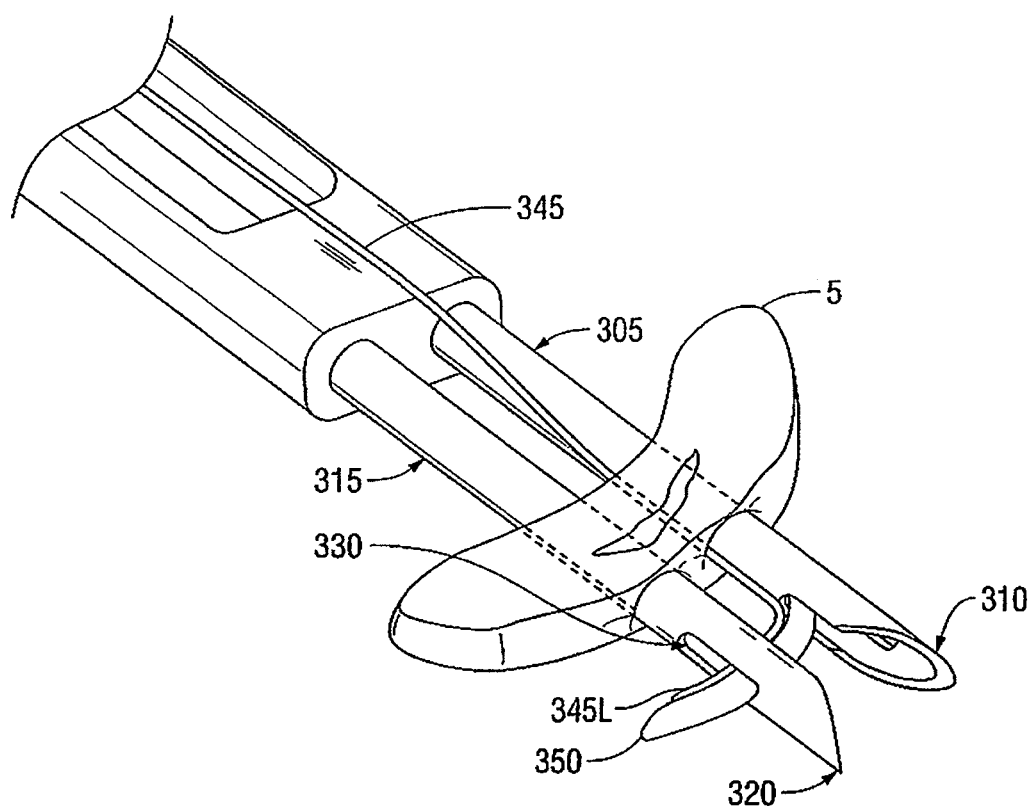
Figure 40:
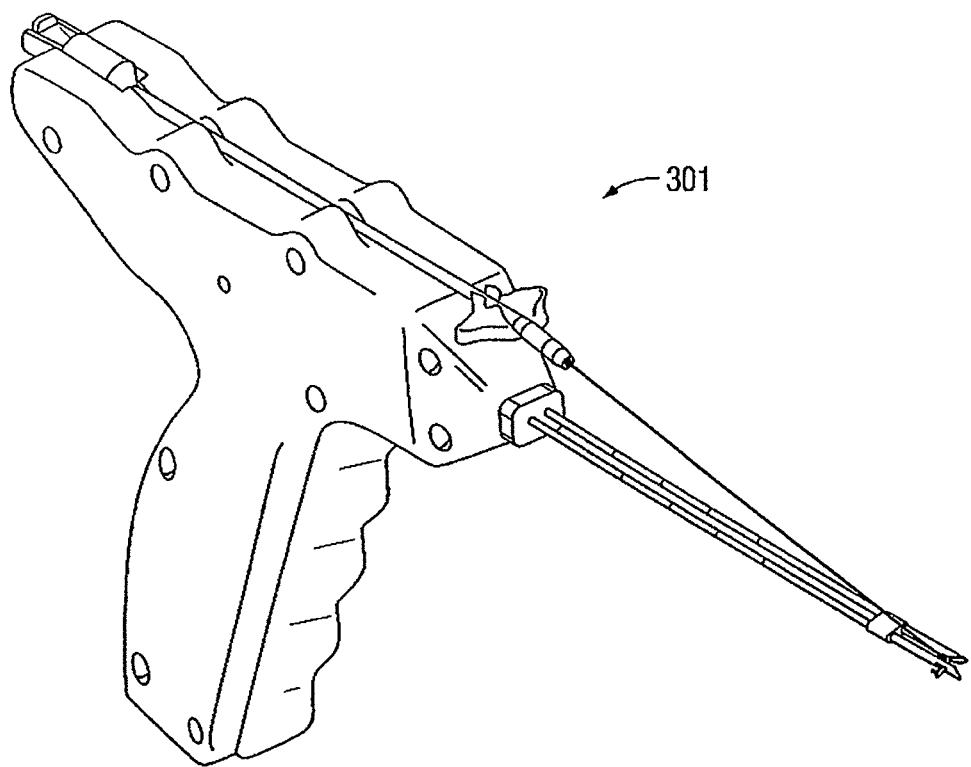
Figure 41:
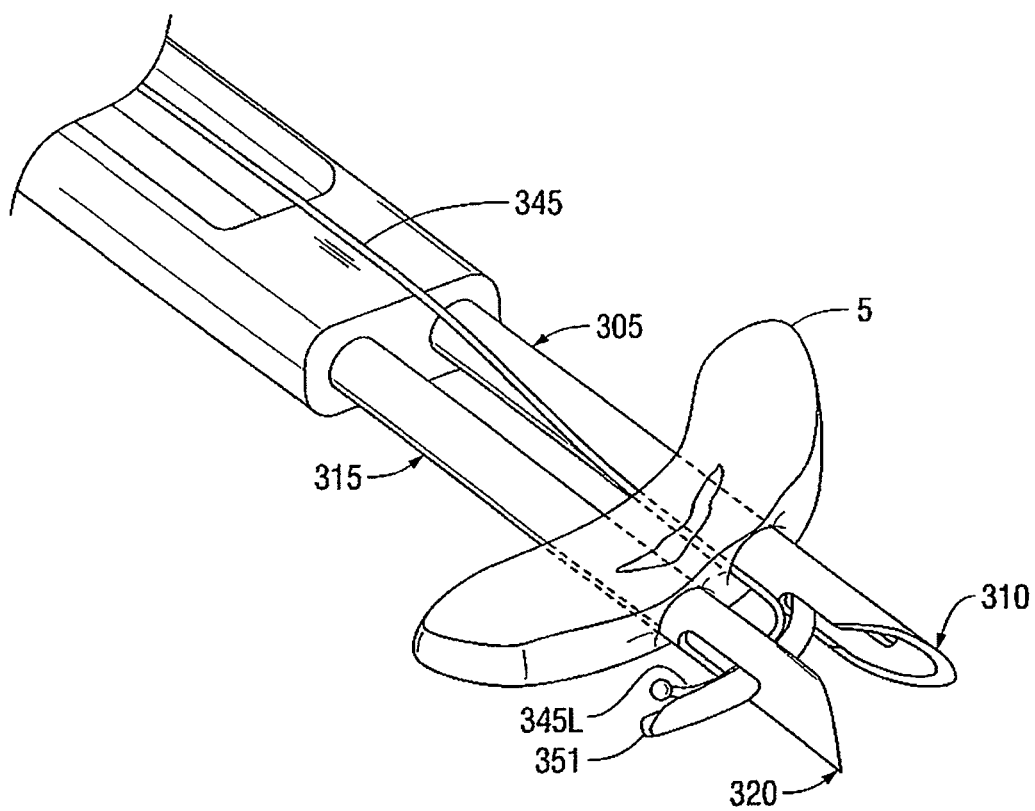

Looking now at FIGS. 31-33, 36 and 37, suture passer 301, with suture cartridge 302 mounted thereon, is first manipulated so that its first needle 305 and its second needle 315 are advanced so that their distal tips 310, 320 are passed completely through meniscus. Next, as seen as FIGS. 38-39, a suture holder 350 carrying a suture 345 is advanced out distal end 310 of first needle 305. Suture holder 350 is configured so that the suture holder will carry the leading portion 345L of suture 345 through a slot 330 of second needle 315 when the suture holder is extended out of first needle 305. Then, as shown in FIGS. 40 and 41, an ejector wire 351 is used to eject leading portion 345L of suture 345 from suture holder 350.

Figure 42:
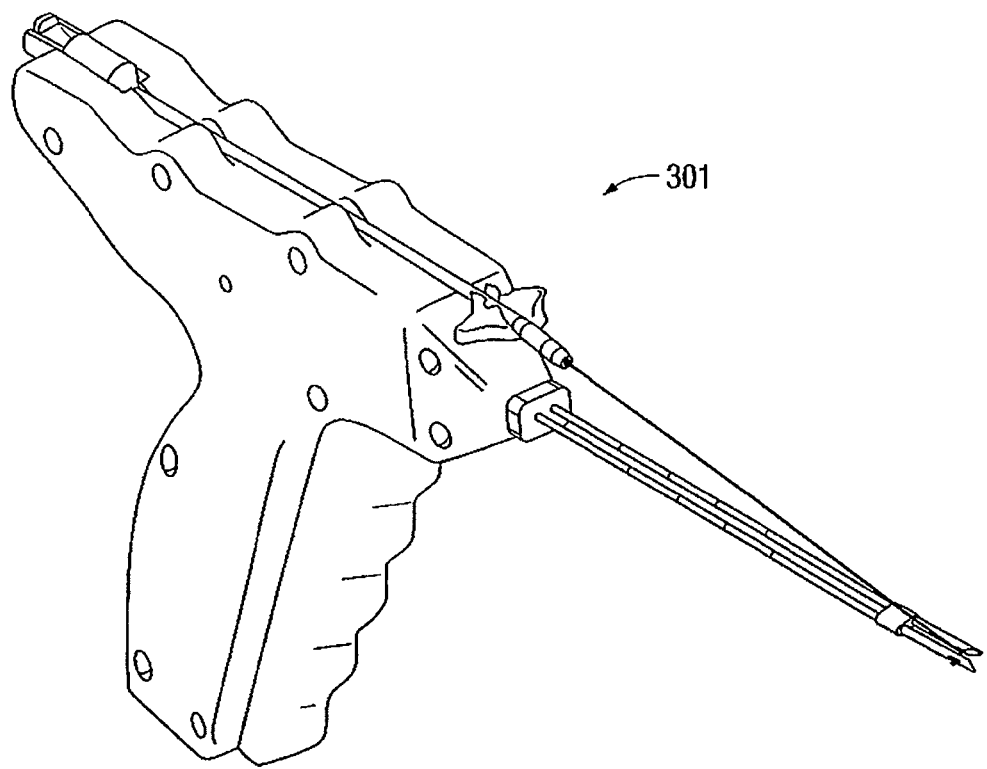
Figure 43:
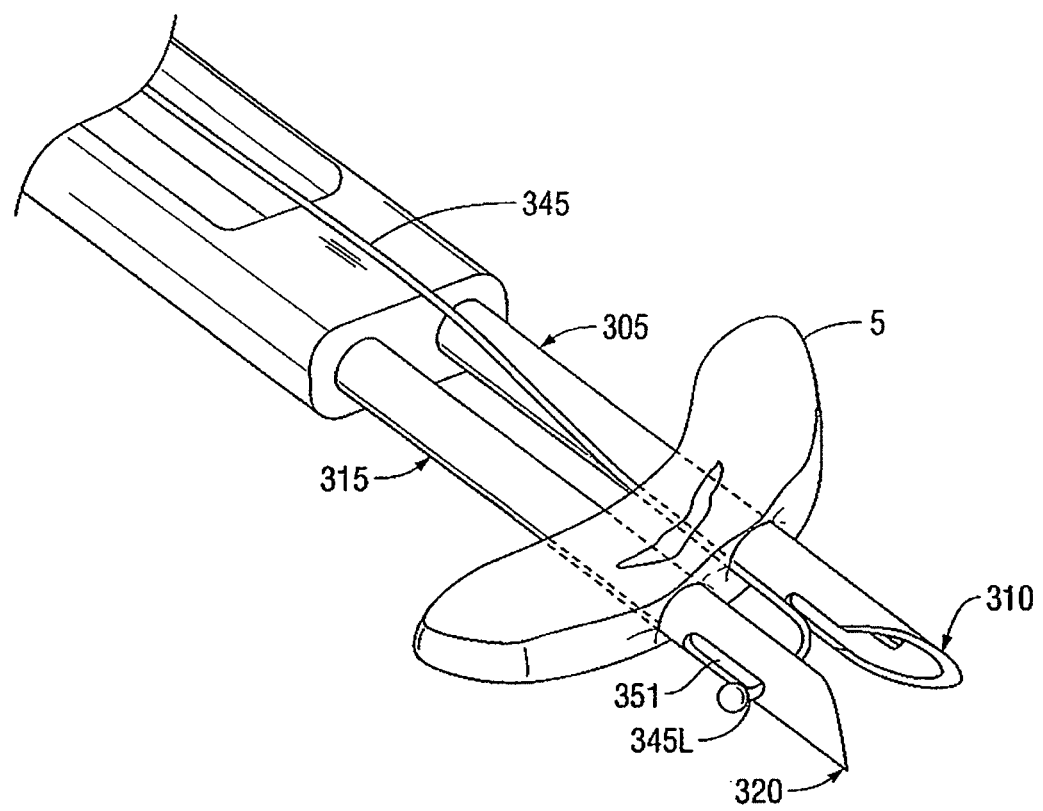

At this point, suture holder 350 is withdrawn, leaving leading portion 345L of suture 345 extending though slot 330 of second needle 315. See FIGS. 42 and 43. Then an obturator 352 is advanced within second needle 315 so as to pin leading portion 345L of suture 345 to second needle 315.

Figure 44:
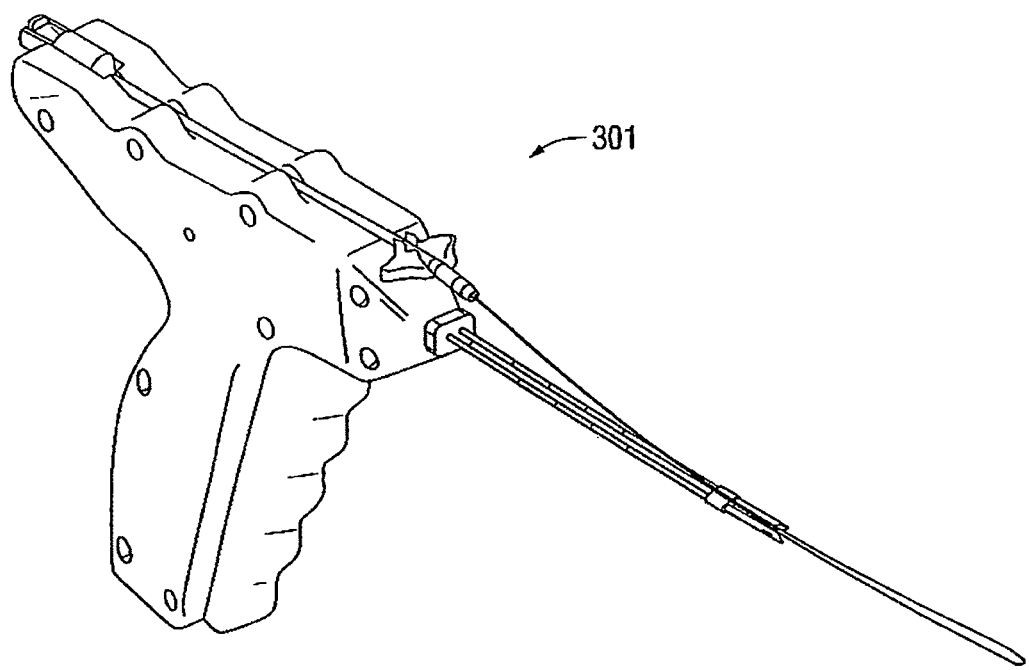
Figure 45:
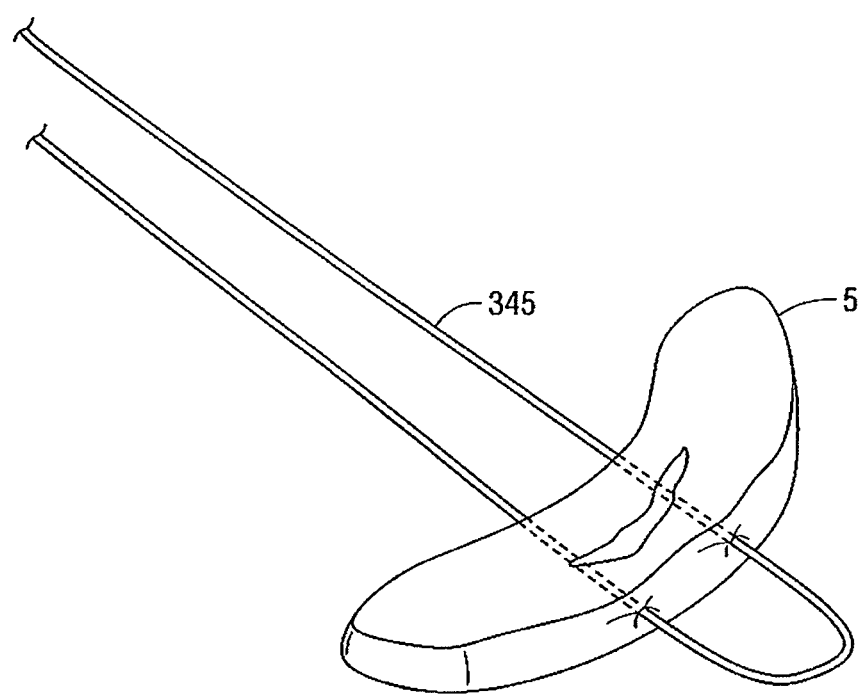

Next, suture passer 301 is retracted so that its first needle 305 and second needle 315 are withdrawn from the meniscus. See FIGS. 44 and 45. Thus, at this point in the procedure, suture 345 will have been passed from the near side of the meniscus, through the meniscus and then back again. Significantly, by appropriately positioning first needle 305 and second needle 315 during the suture passing operation, suture 345 will extend across tear 20 formed in meniscus 5.

Figure 46:
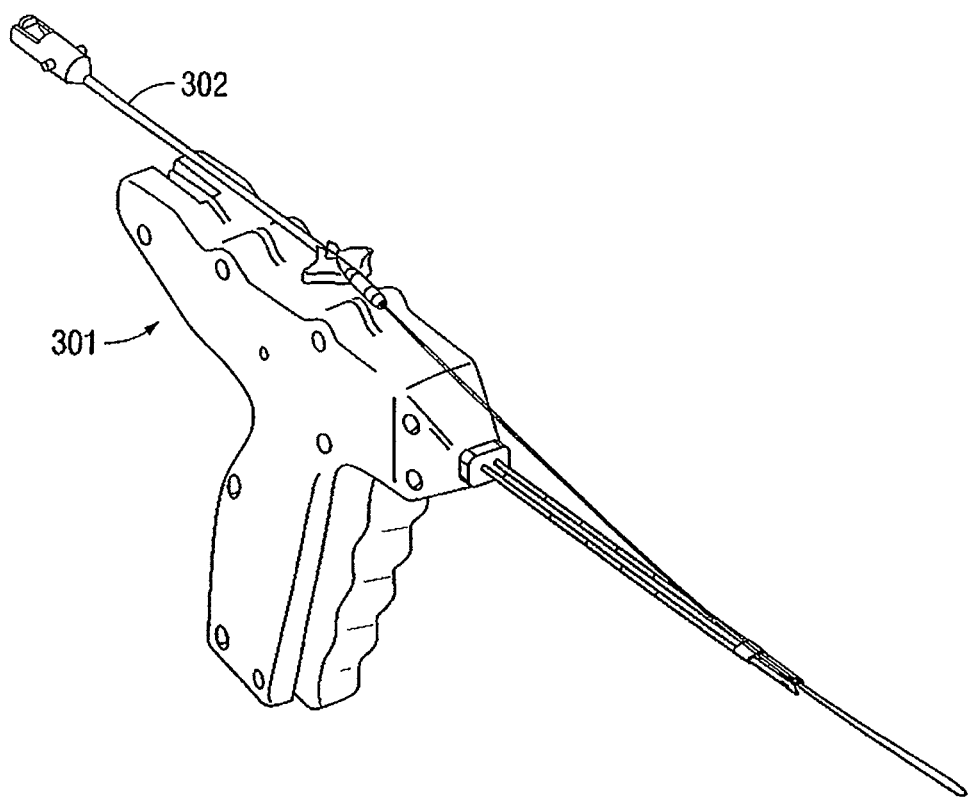
Figure 47:
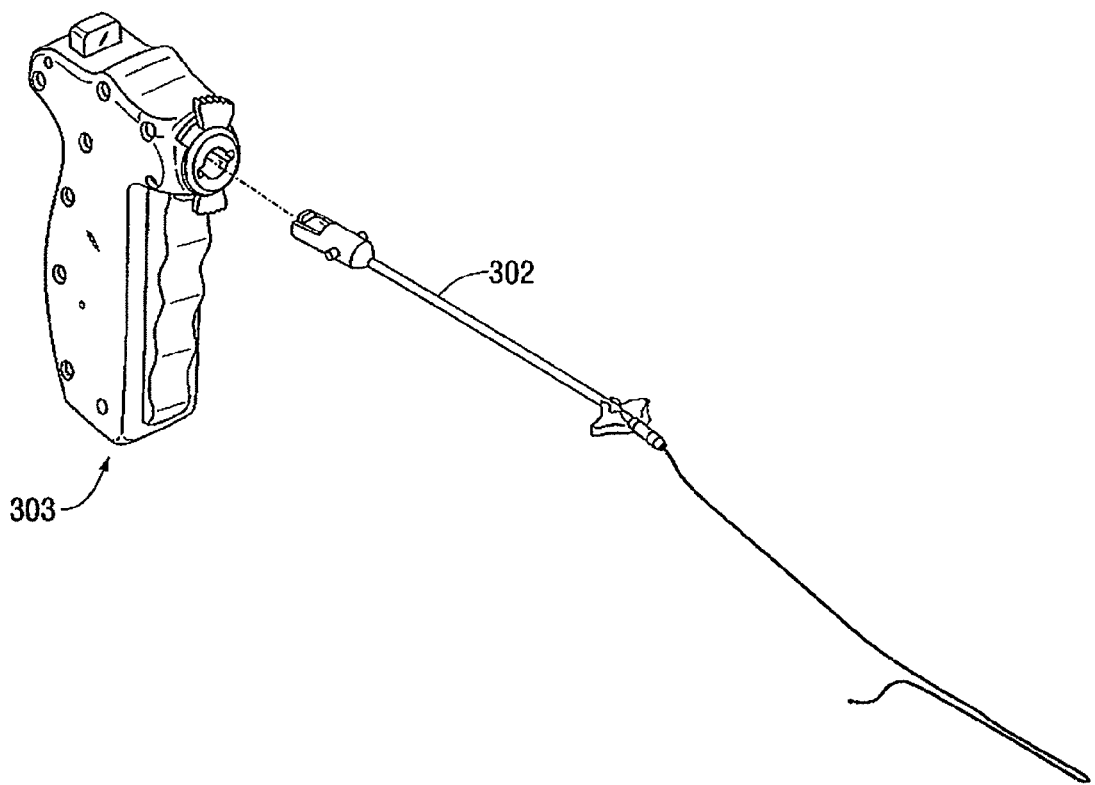
Figure 48:
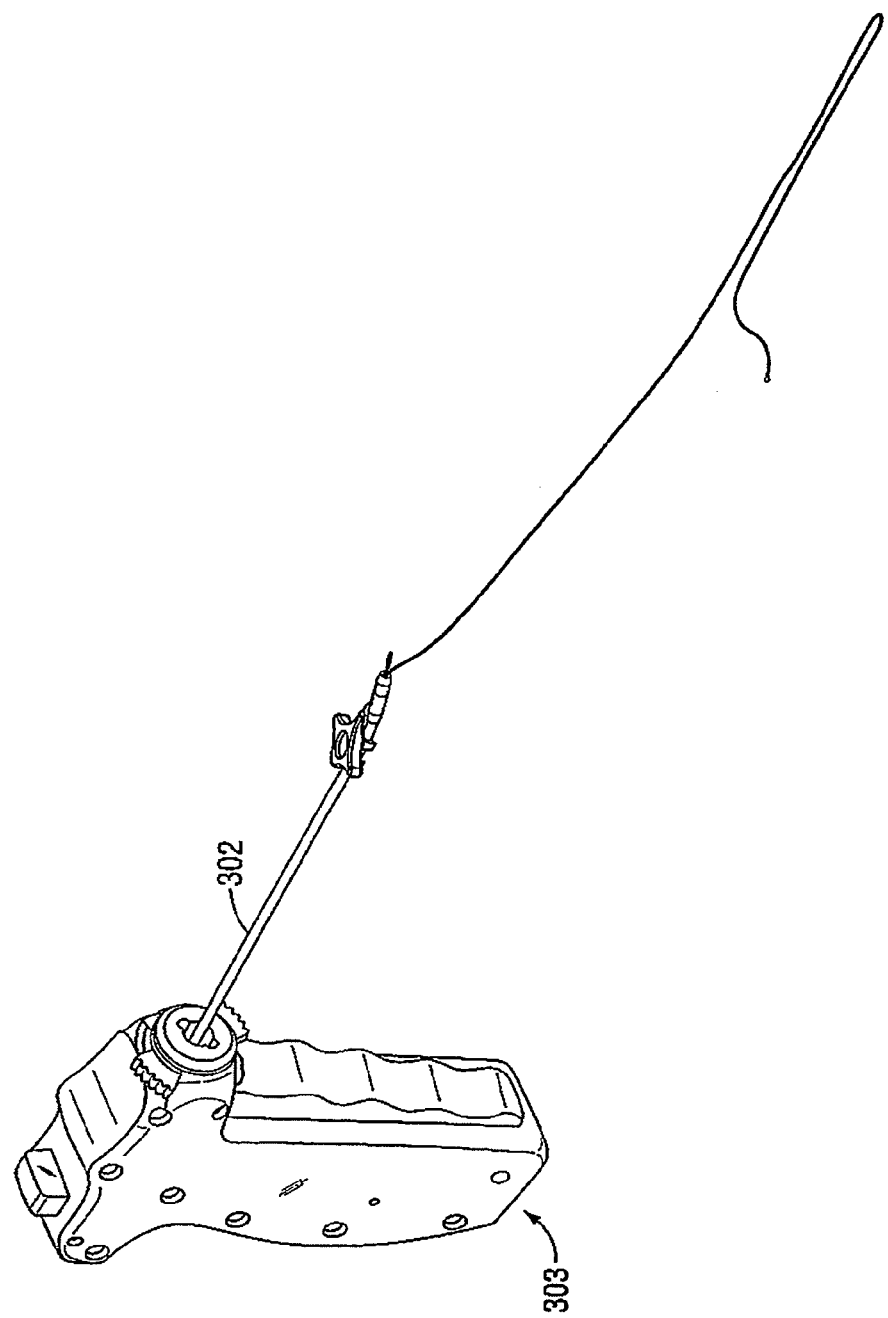
Figure 49:
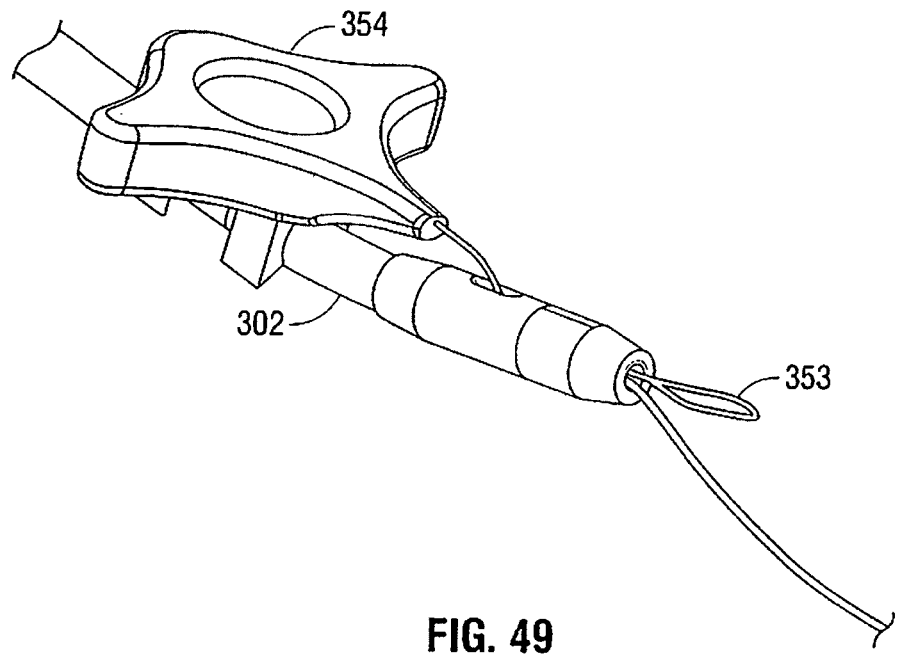
Figure 50:
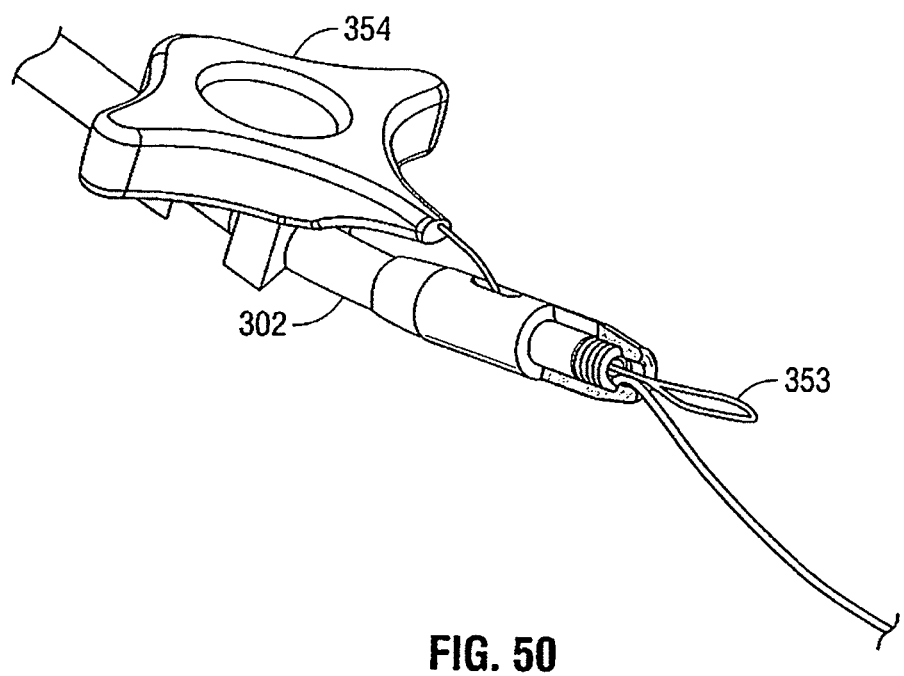
Figure 51:
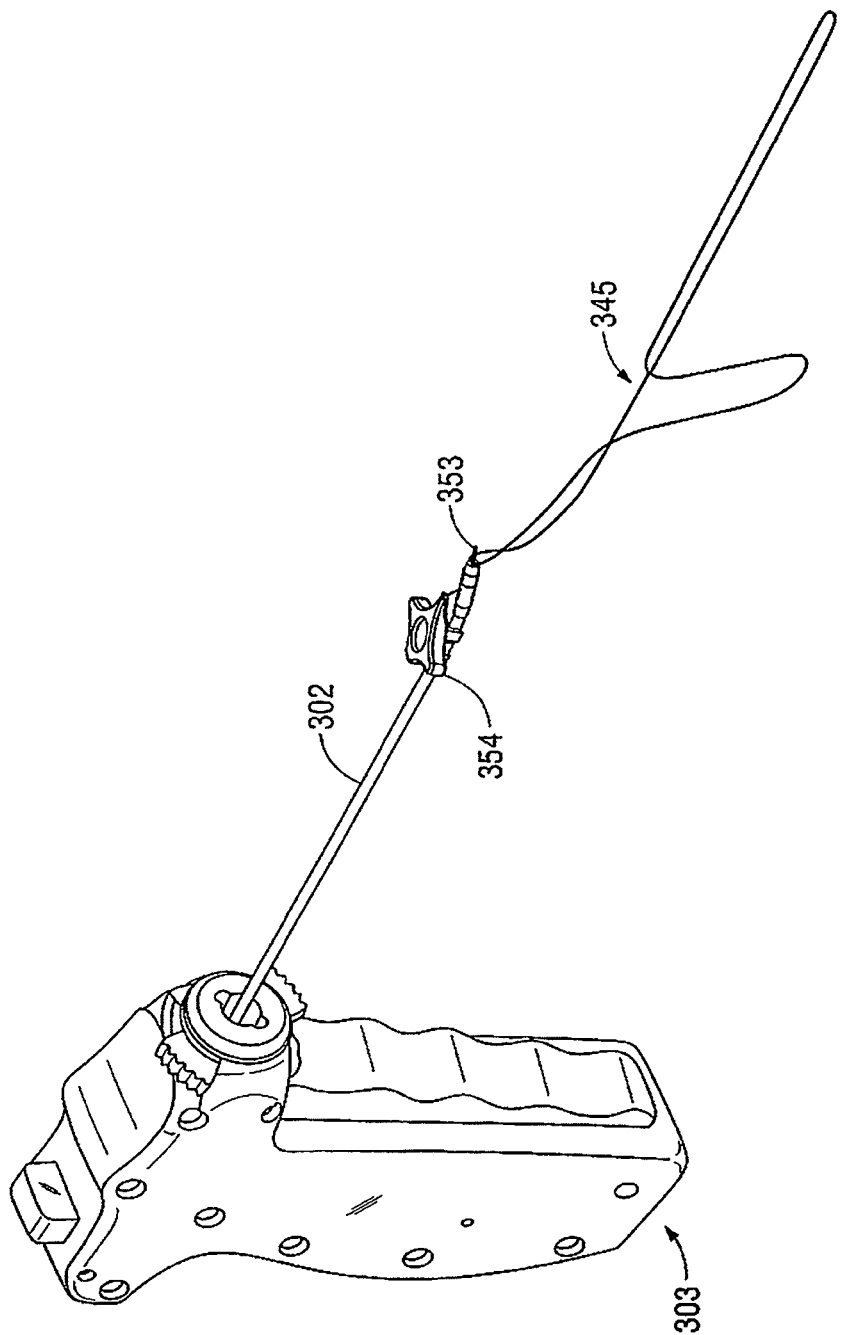
Figure 52:
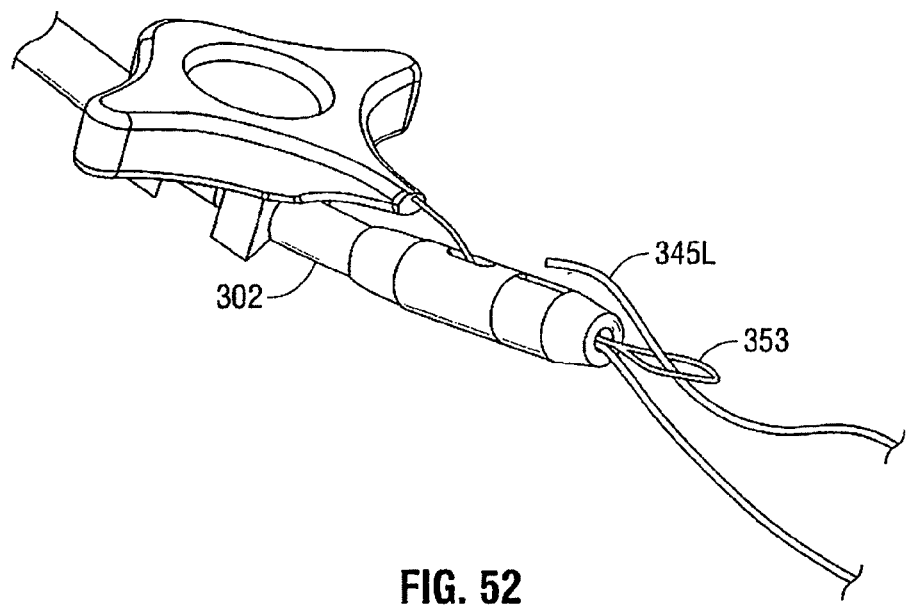
Figure 53:
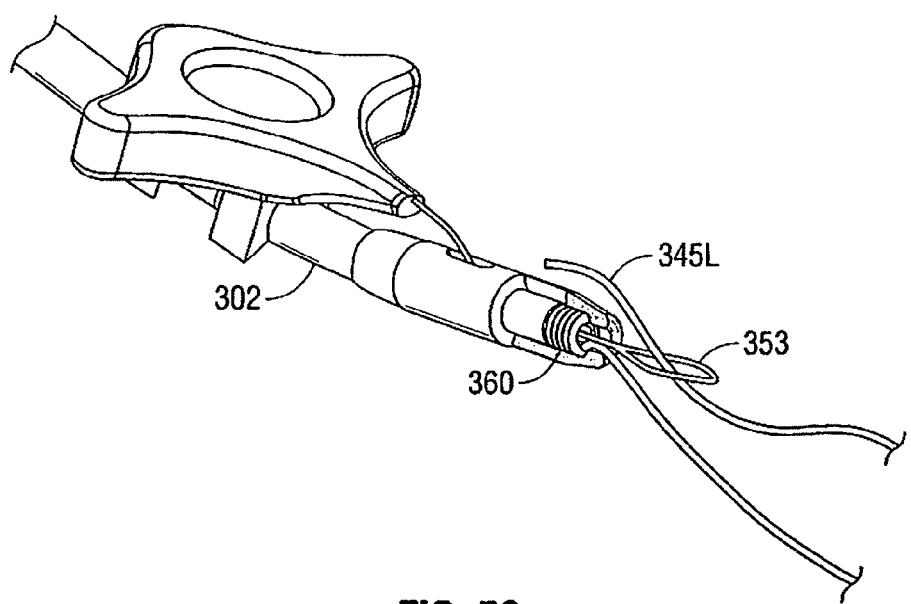
Figure 54:
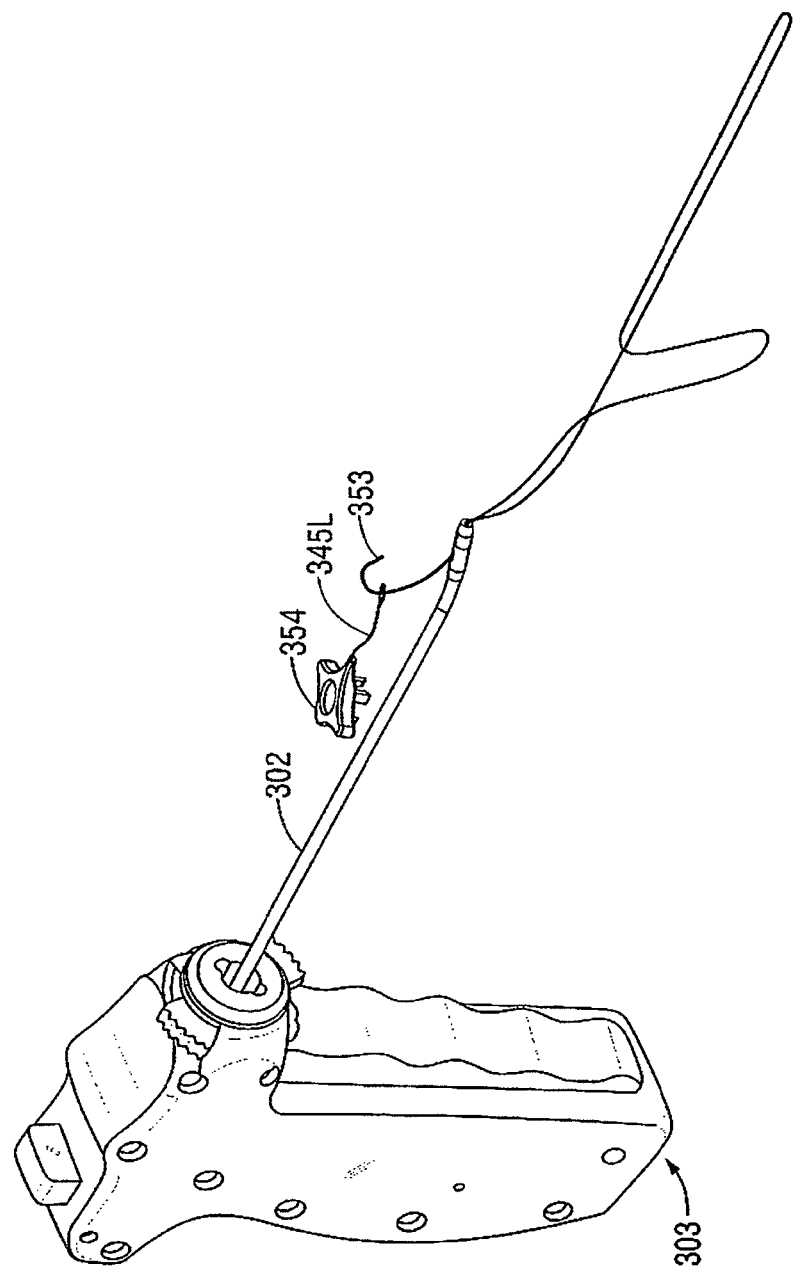
Figure 55:
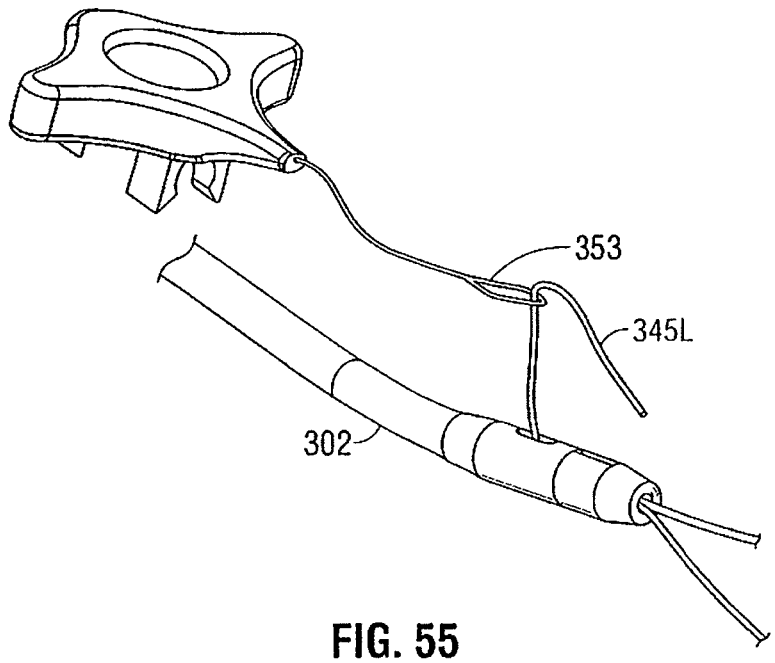
Figure 56:
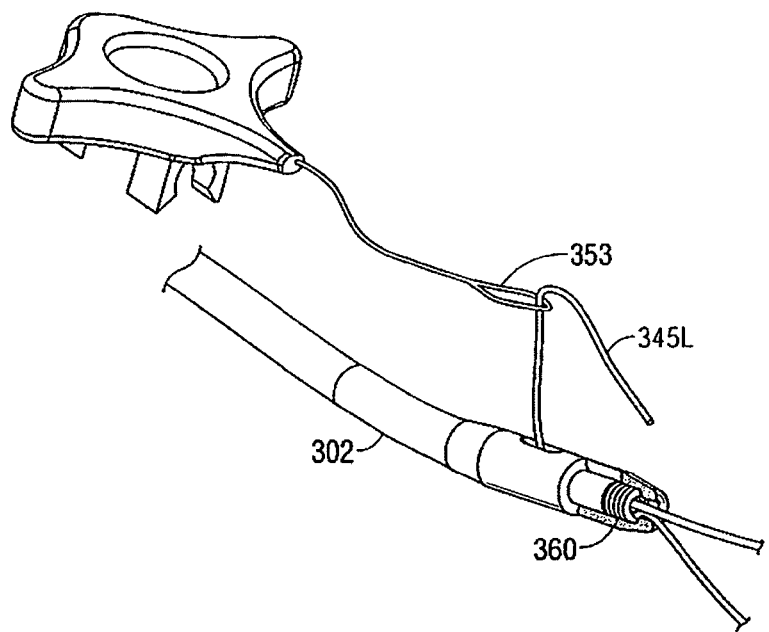

Next, the suture is tied down so as to close the tear in the meniscus. This may be done in a variety of ways which will be apparent to those skilled in the art in view of the present disclosure. In one preferred form of the invention, this is accomplished in the following way. First, as shown in FIG. 46, suture cartridge 302 is dismounted from suture passer 301. Then suture cartridge 302 is mounted to knot pusher/cutter 303 (FIG. 47) and locked in place (FIG. 48). At this point, and looking now at FIGS. 49 and 50, suture cartridge 302 is ready to receive leading portion 345L of suture 345. Next, leading portion 345L of suture 345 is inserted into a loop 353 of a snare basket 354, as shown in FIGS. 51-53. Snare basket 354 essentially comprises a conventional suture threader component, or needle threader component, in the sense that a collapsible loop is formed at the end of a pullable tab. Then snare basket 354 is retracted, carrying leading portion 345L of suture 345 through a pre-formed, uncinched knot 360 formed in the trailing portion 345T of suture 345 and disposed at the tip of knot pusher/cutter 303. See FIGS. 54-56. It will be appreciated that as snare basket 354 carries leading portion 345L of suture 345 through pre-formed, uncinched knot 360, the suture passes back through itself.

Figure 57:
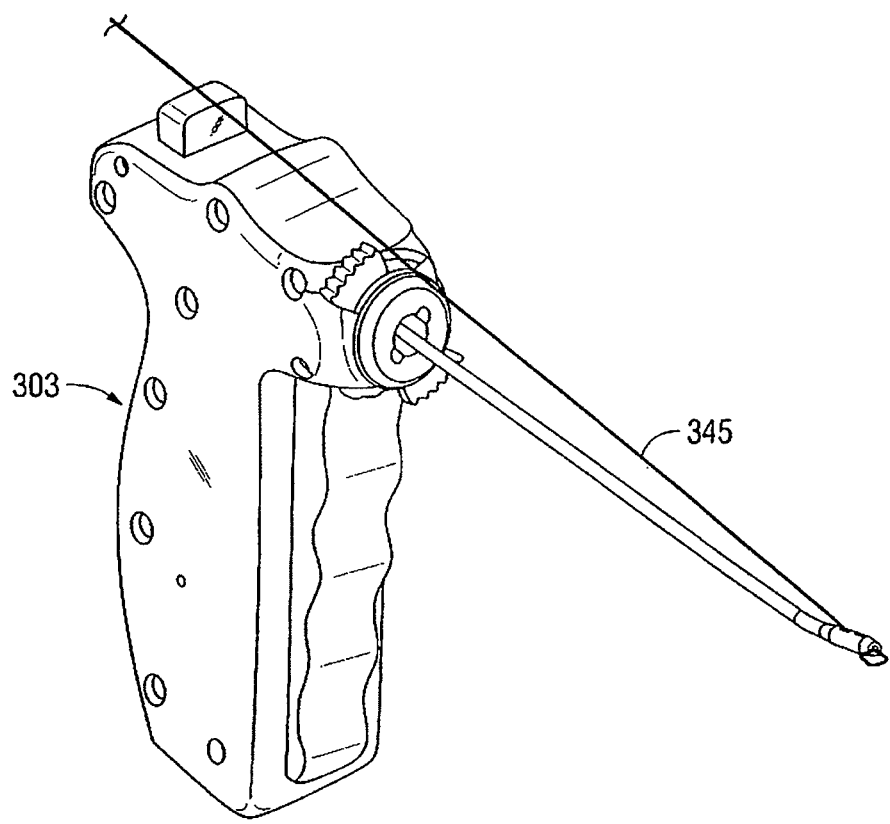
Figure 58:
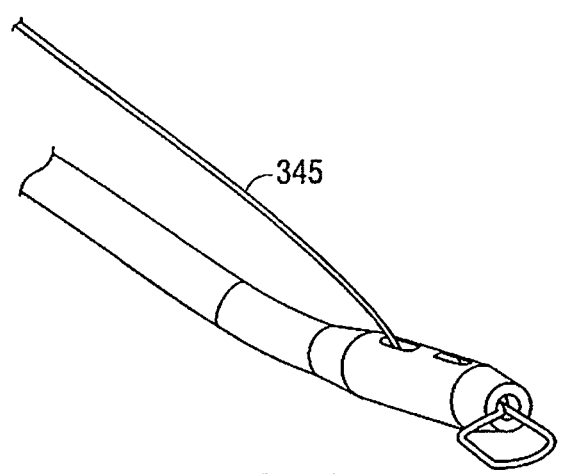
Figure 59:
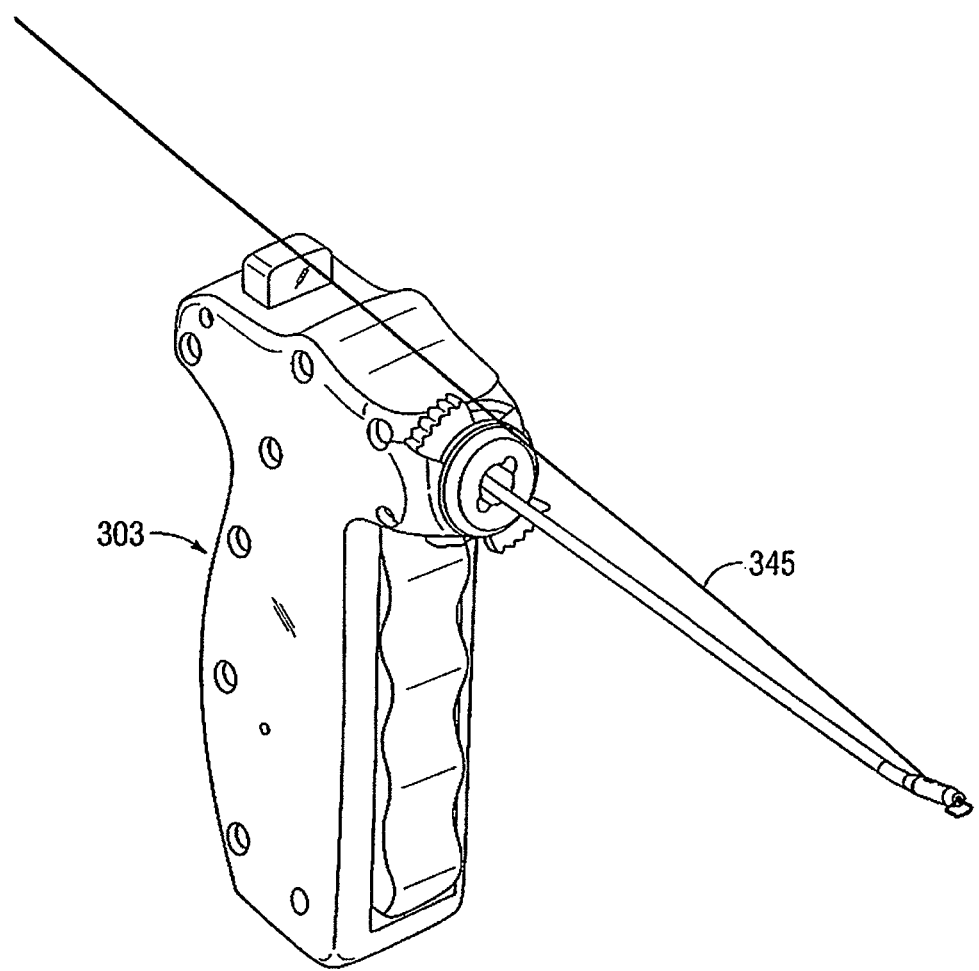
Figure 60:
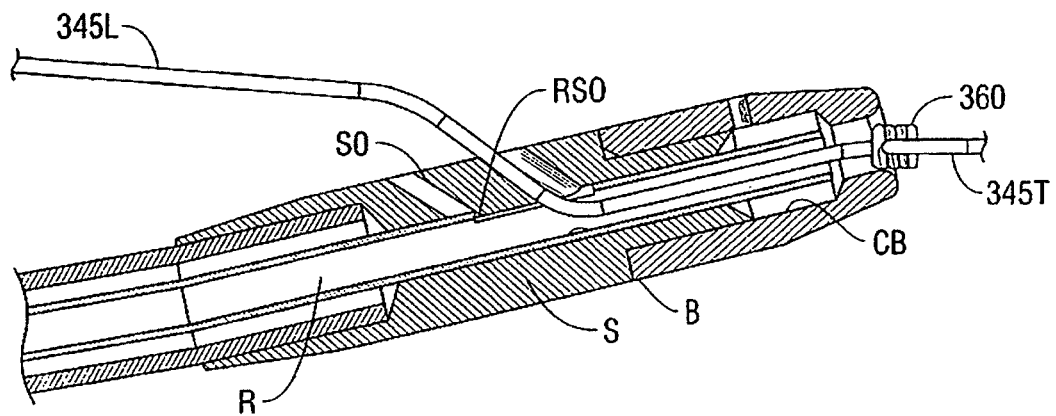
Figure 61:
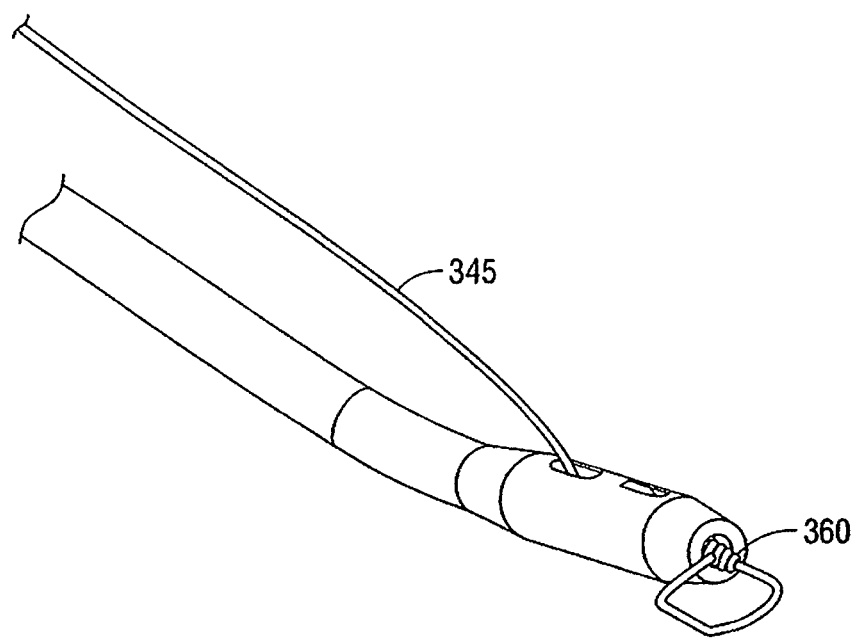
Figure 62:
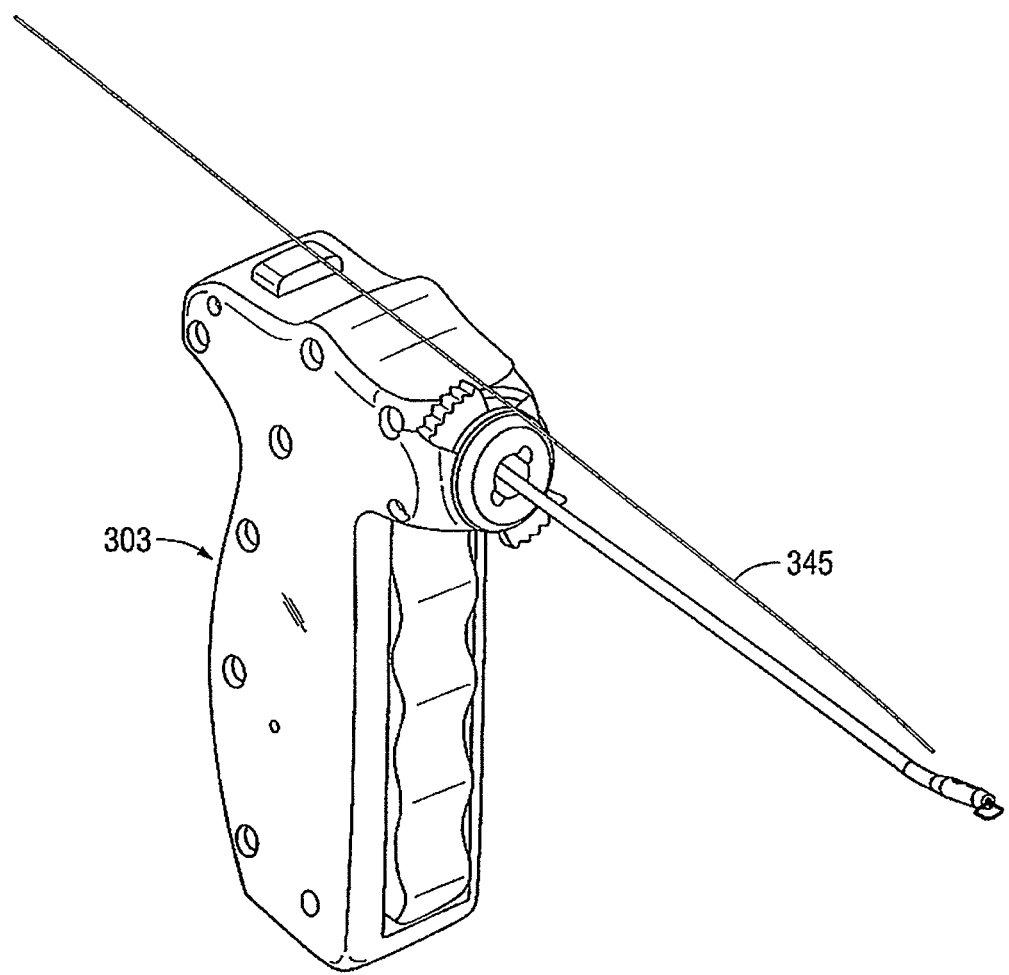
Figure 63:
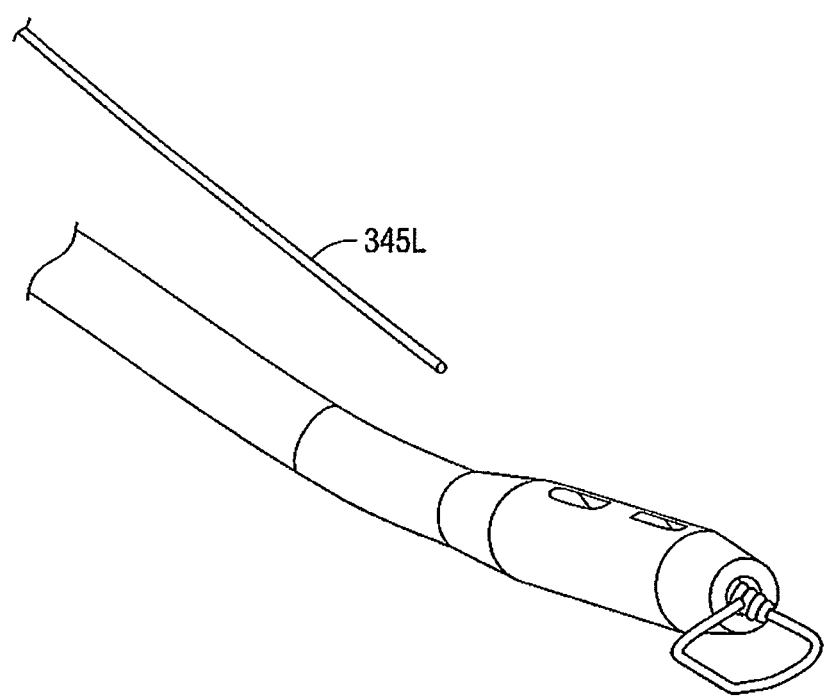
Figure 64:
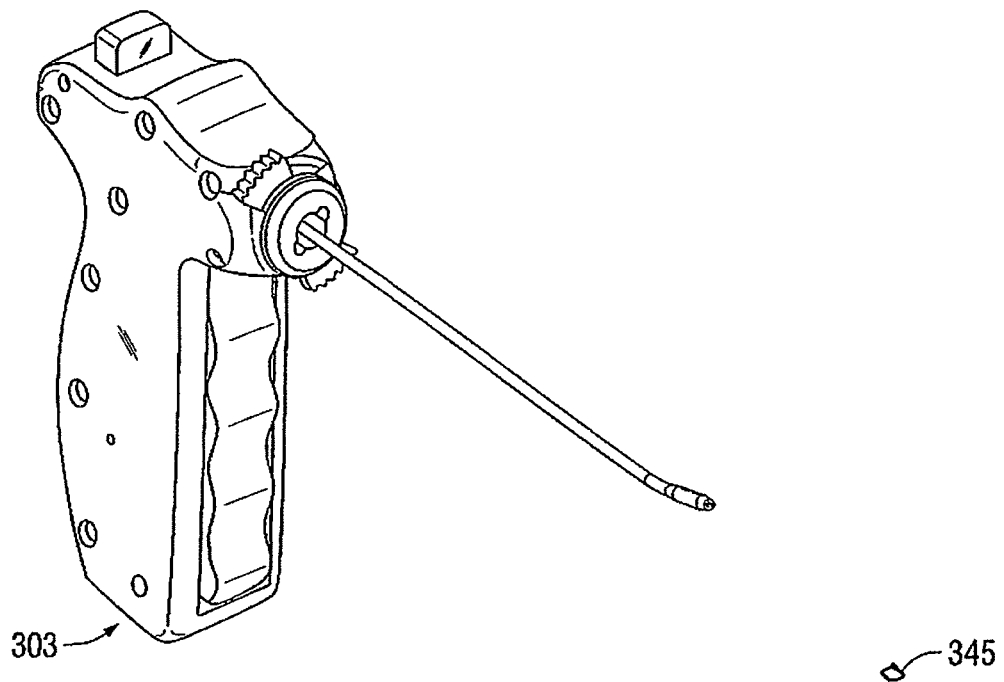
Figure 65:
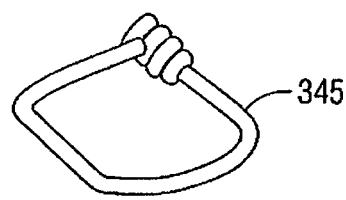

Then, and looking now at FIGS. 57-59, knot pusher/cutter 303 is advanced distally so as to bring pre-formed, un-cinched knot 360 to the near side surface of the meniscus. Next, as shown in FIGS. 60 and 61, pre-formed, un-cinched knot 360 is tightened. Then leading portion 345L of suture 345 is trimmed away by knot pusher/cutter 303 (FIGS. 62 and 63). Finally, knot pusher/cutter 303 is removed, leaving suture 345 closing the tear in the meniscus (FIGS. 64 and 65) with a low-profile suture fixation.

In one preferred form of the invention, and looking now at FIG. 60, knot pusher/cutter 303 comprises a shaft S having a central bore B, a counterbore CB and a side opening SO. A hollow ram R, having a ram side opening RSO, is slidably disposed within bore B of shaft S. Prior to knot deployment, the pre-formed, uncinched knot 360 is seated within counterbore CB; and after leading portion 345L of suture 345 is passed through pre-formed, uncinched knot 360, leading portion 345L is drawn through ram side opening RSO and shaft side opening SO; and when the knot is to be separated from shaft S, ram R is moved distally, first pushing the knot out of the shaft and, after cinching, thereafter cutting leading portion 345L of suture 345 by virtue of moving side opening SO out of alignment with ram side opening RSO.

In one preferred form of the invention, the cinched knot is separated from shaft S in a first discrete step, and then the suture is cut in a second discrete step.

Fourth Preferred Method and Apparatus

Figure 66:
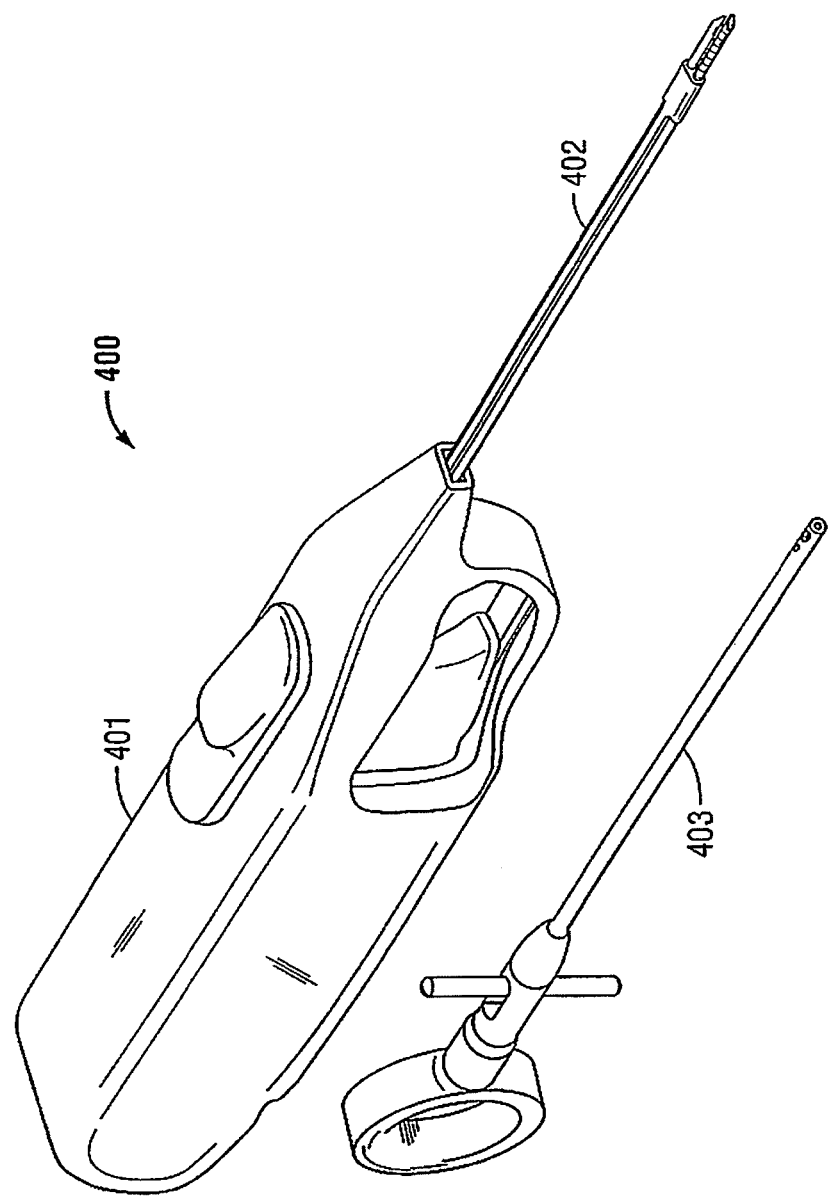
FIGS. 66-91 are a series of views showing a fourth method and apparatus for repairing a meniscal tear, with the meniscus being omitted from selected views in order to simplify the drawing and enhance comprehension.

Looking now at FIG. 66, there is shown an apparatus 400 for use in closing tear 20 in meniscus 5. Apparatus 400 generally comprises a handle 401, a needle cartridge 402 and a pusher/cutter 403. Pusher/cutter 403 is similar to suture cartridge 302 discussed above, in the sense that it carries a pre-formed, uncinched knot, etc., as will hereinafter be discussed. Specific details of the construction and function of handle 401, needle cat ridge 402 and pusher/cutter 403 will be disclosed in the course of the following discussion of using apparatus 400 to close tear 20 in meniscus 5.

Figure 67:
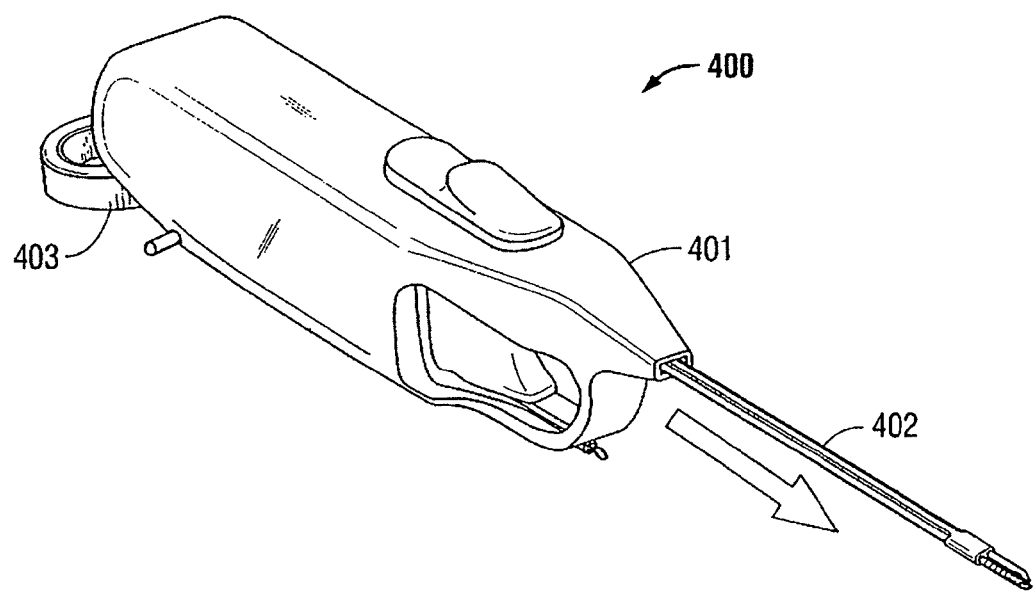
Figure 68:
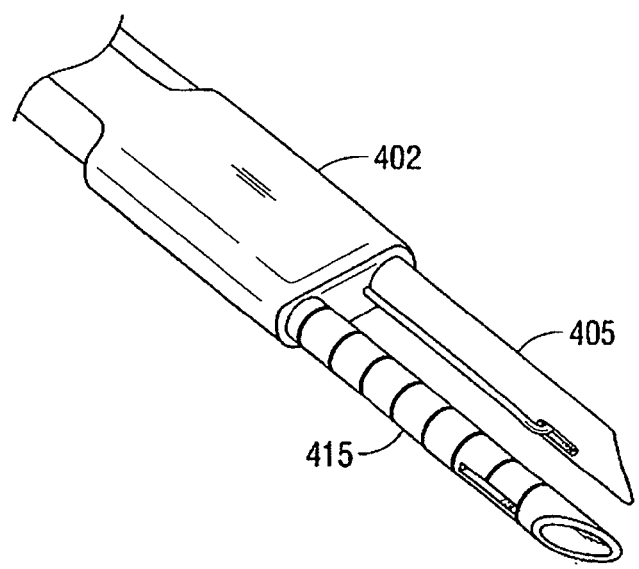

Looking now at FIGS. 67 and 68, apparatus 400 is manipulated so that its first needle 405 and its second needle 415 are advanced so that their distal tips 410, 420 are passed completely through meniscus 5.

Figure 69:
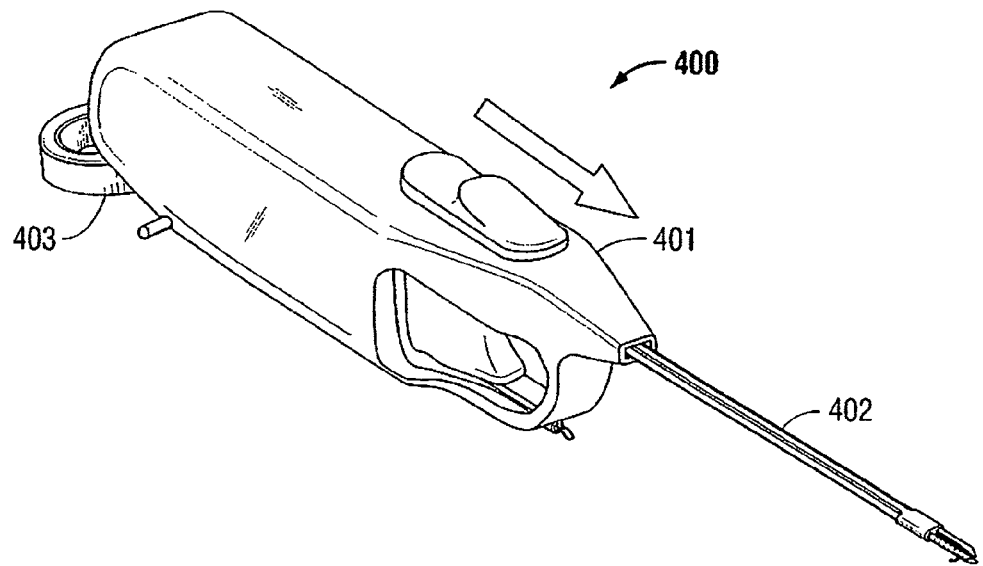
Figure 70:
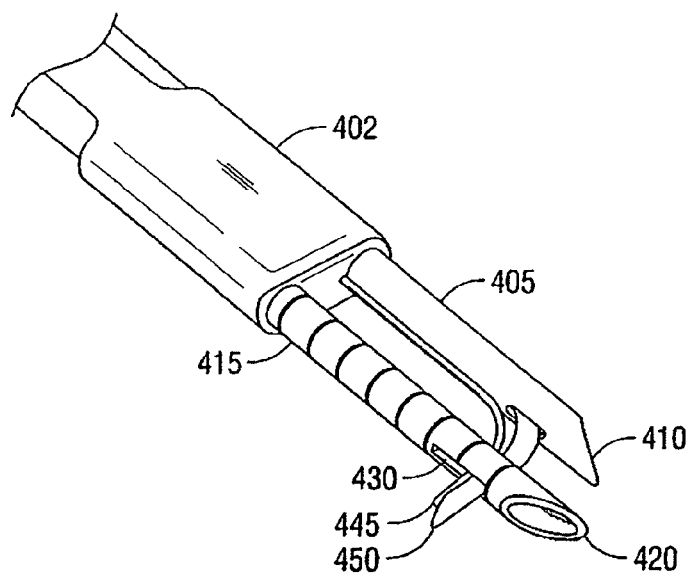

Next, as seen as FIGS. 69 and 70, a suture holder 450 carrying a suture 445 is advanced out distal end 410 of first needle 405. Suture holder 450 is configured so that the suture holder will carry the leading portion 445L of suture 445 through a slot 430 of second needle 415 when the suture holder is extended out of first needle 405.

Figure 71:
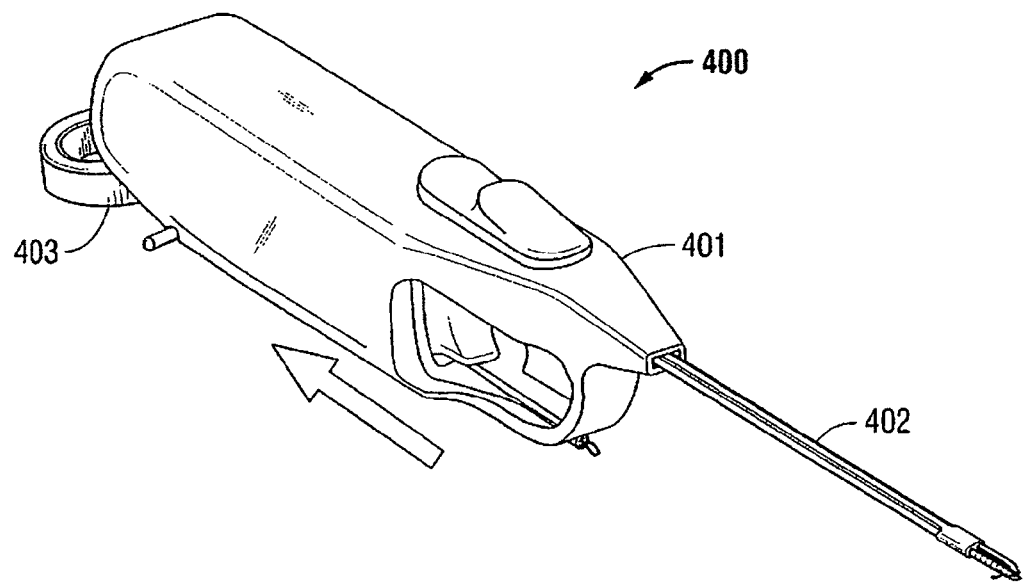
Figure 72:
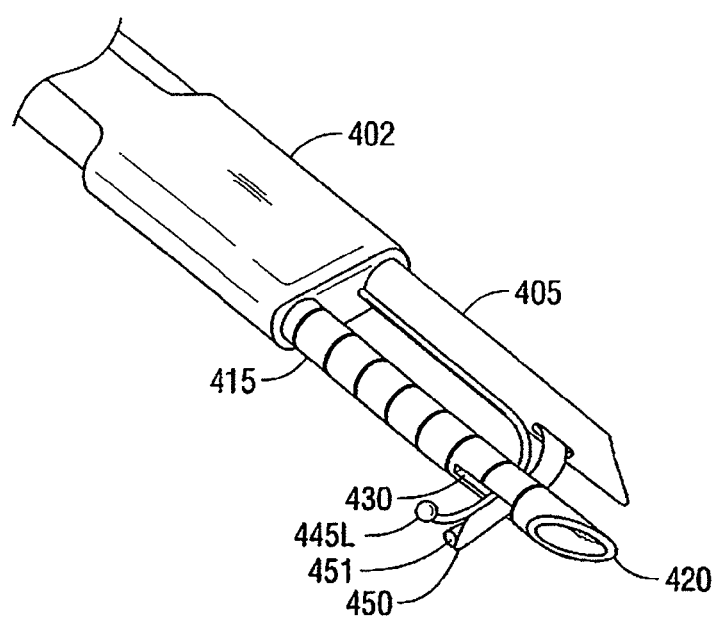
Figure 73:
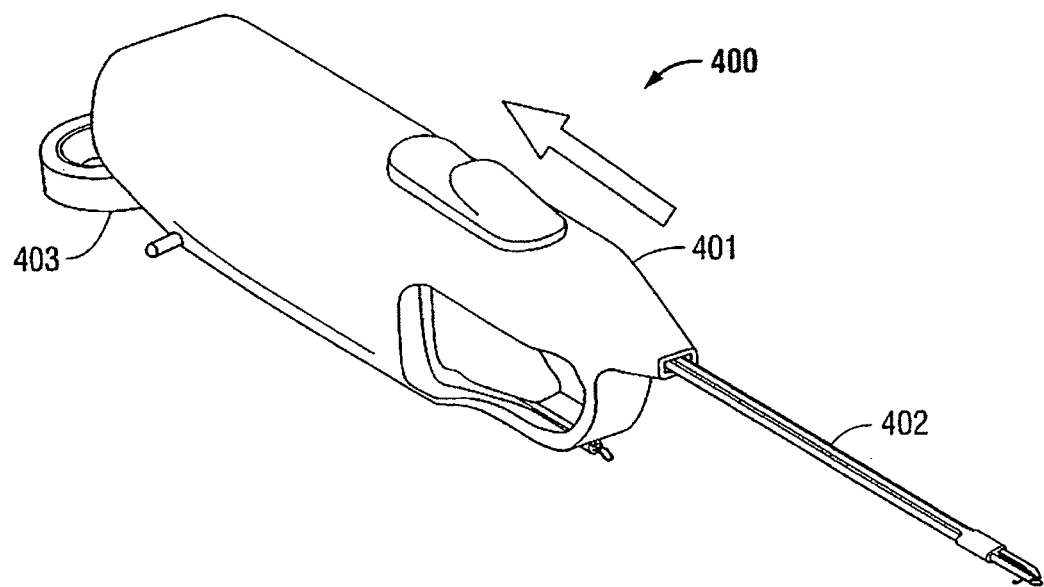
Figure 74:
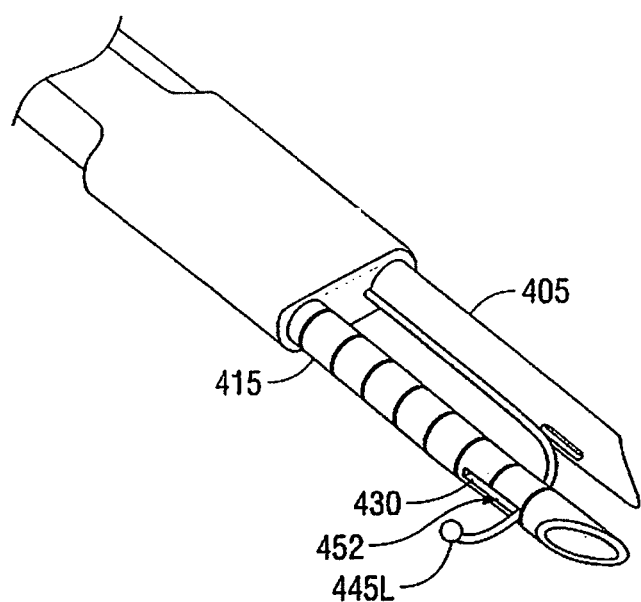

Then, as shown in FIGS. 71 and 72, an ejector wire 451 is used to eject leading portion 445L of suture 445 from suture holder 450. At this point, suture holder 450 is withdrawn, leaving leading portion 445L of suture 445 extending though slot 430 of second needle 415. See FIGS. 73 and 74. Then an obturator 452 is advanced within second needle 415 so as to pin leading portion 445L of suture 445 to second needle 415.

Figure 75:
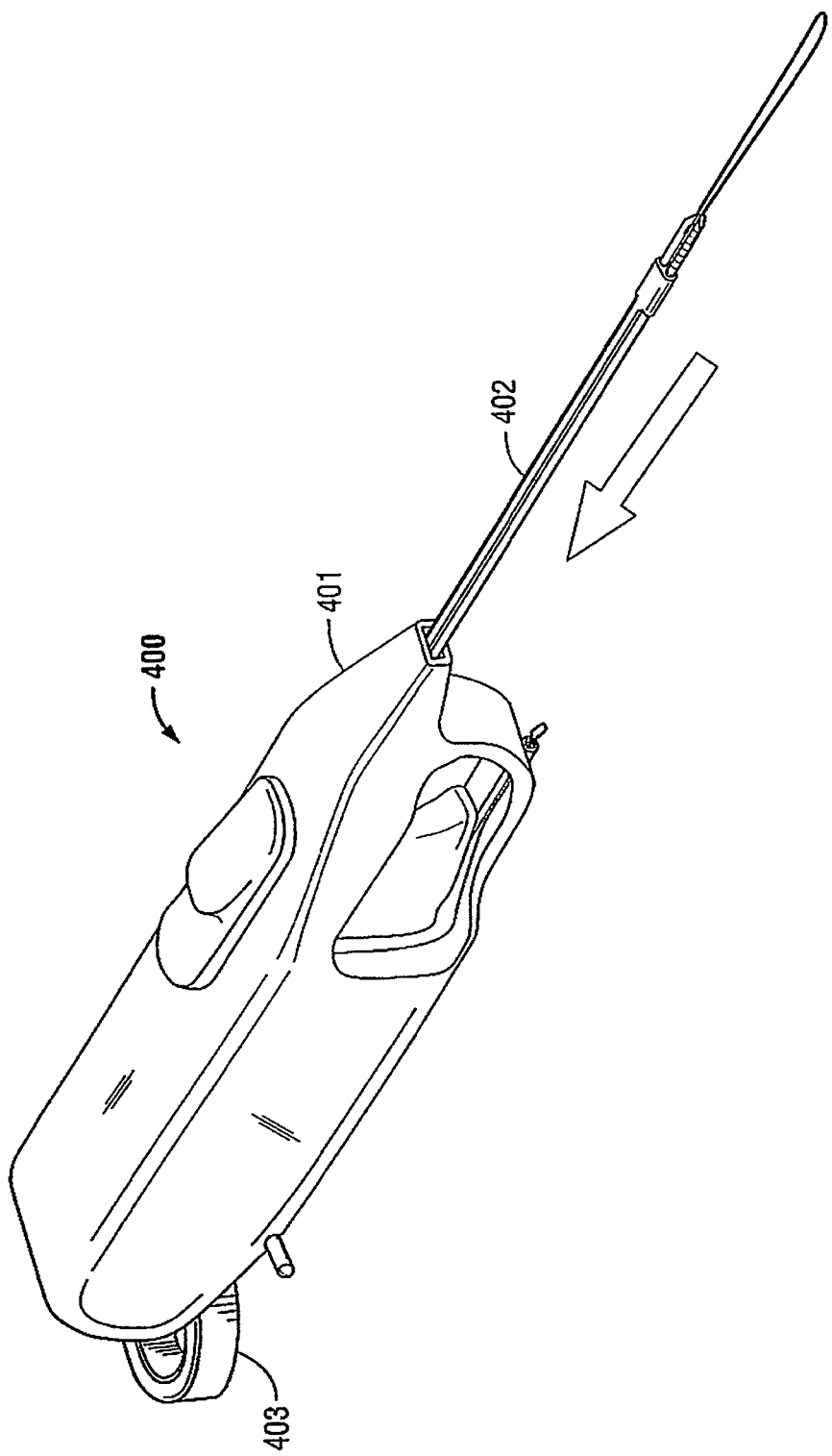

Next, handle 401 is retracted so that its first needle 405 and second needle 415 are withdrawn from the meniscus. See FIG. 75. Thus, at this point in the procedure, suture 445 will have been passed from the near side of the meniscus, through the meniscus and then back again. Significantly, by appropriately positioning first needle 405 and second needle 415 during the suture passing operation, suture 445 will extend across tear 20 formed in meniscus 5.

Figure 76:
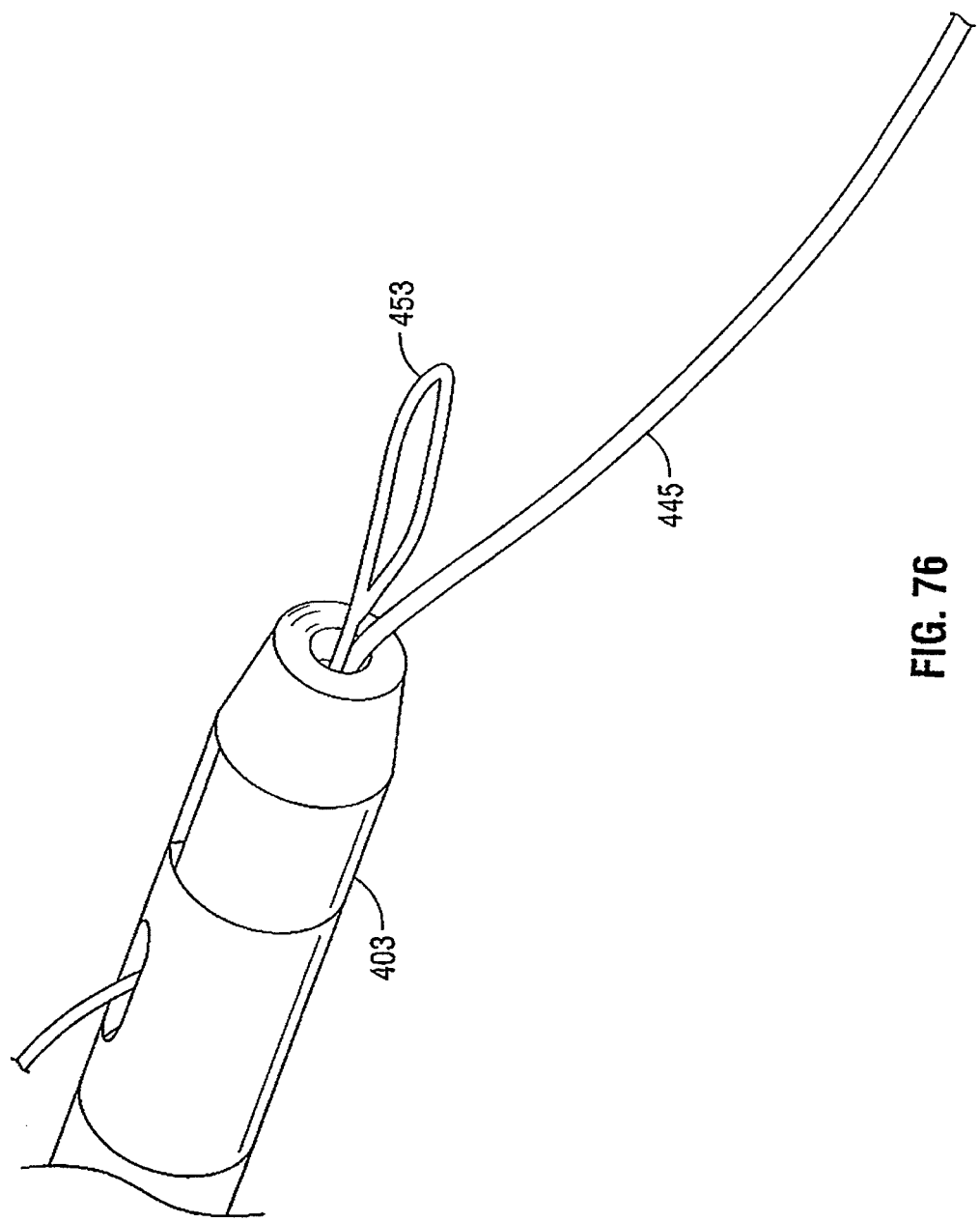
Figure 77:
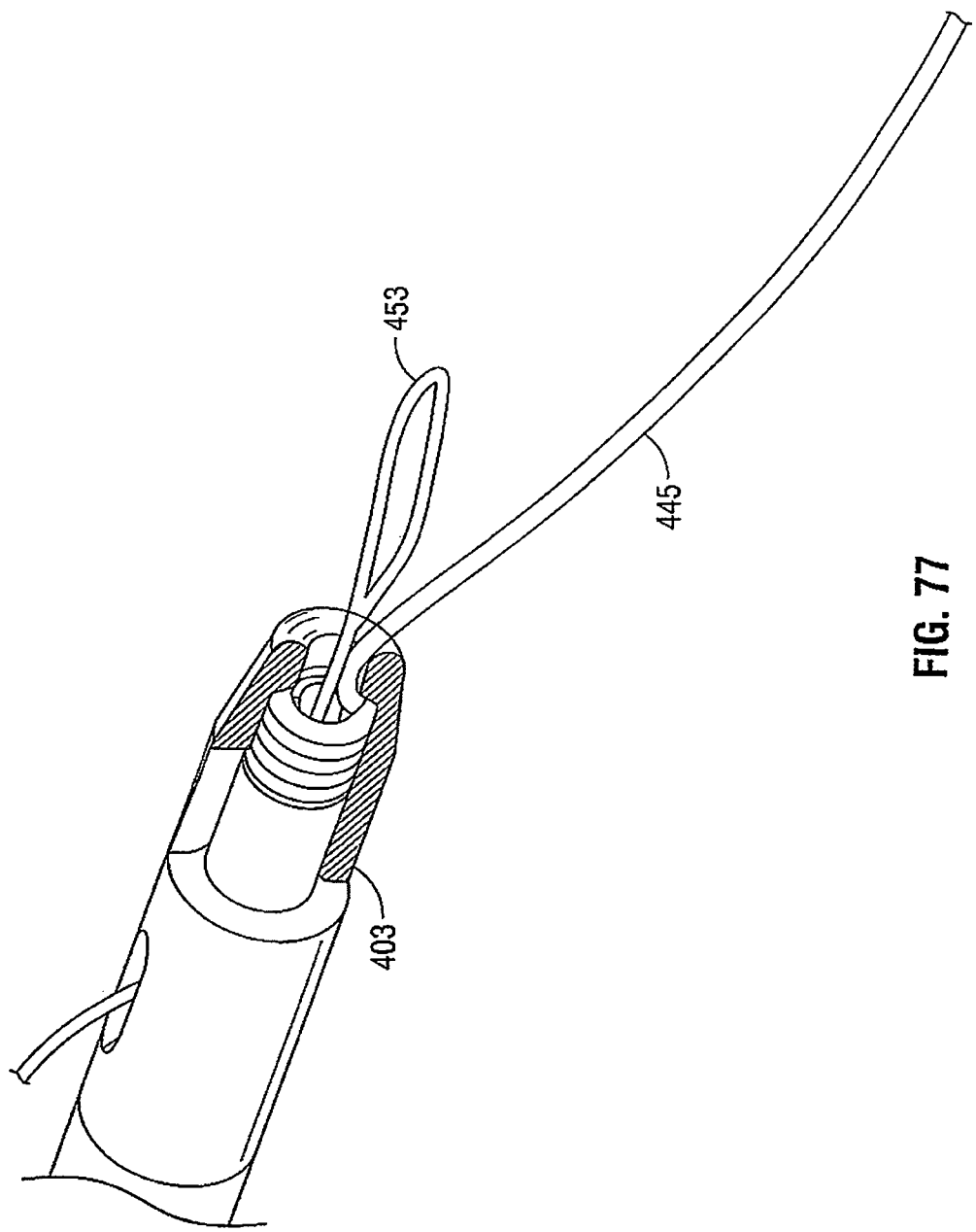
Figure 78:
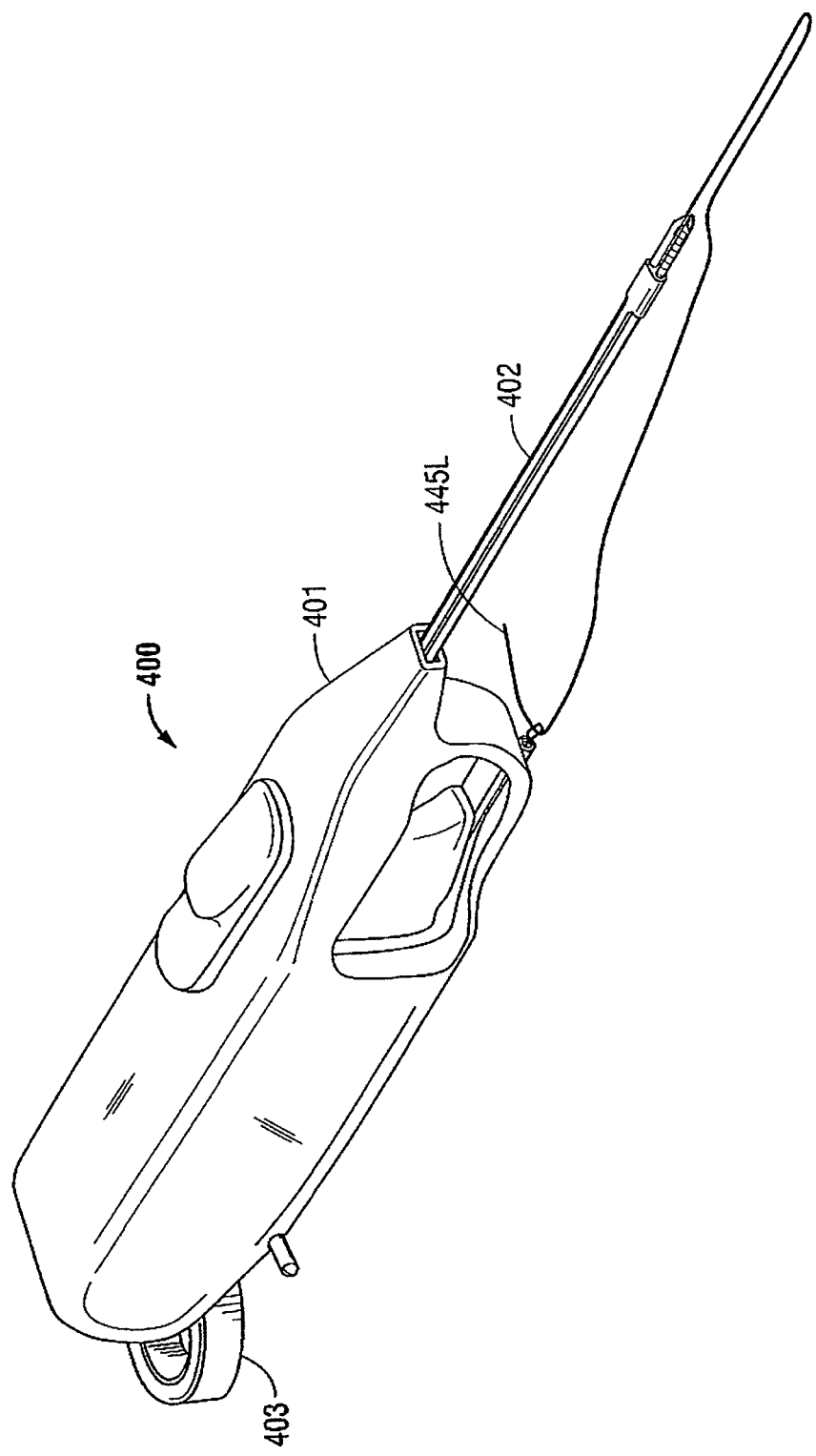
Figure 79:
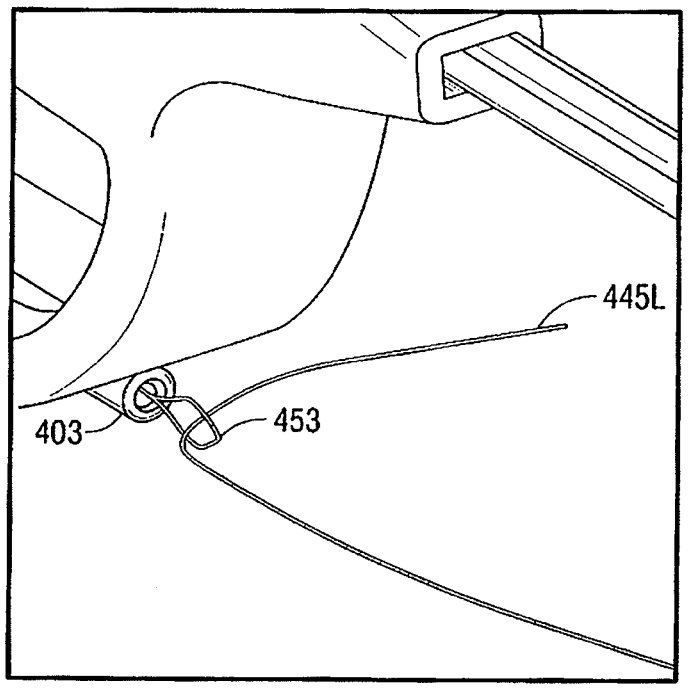
Figure 80:
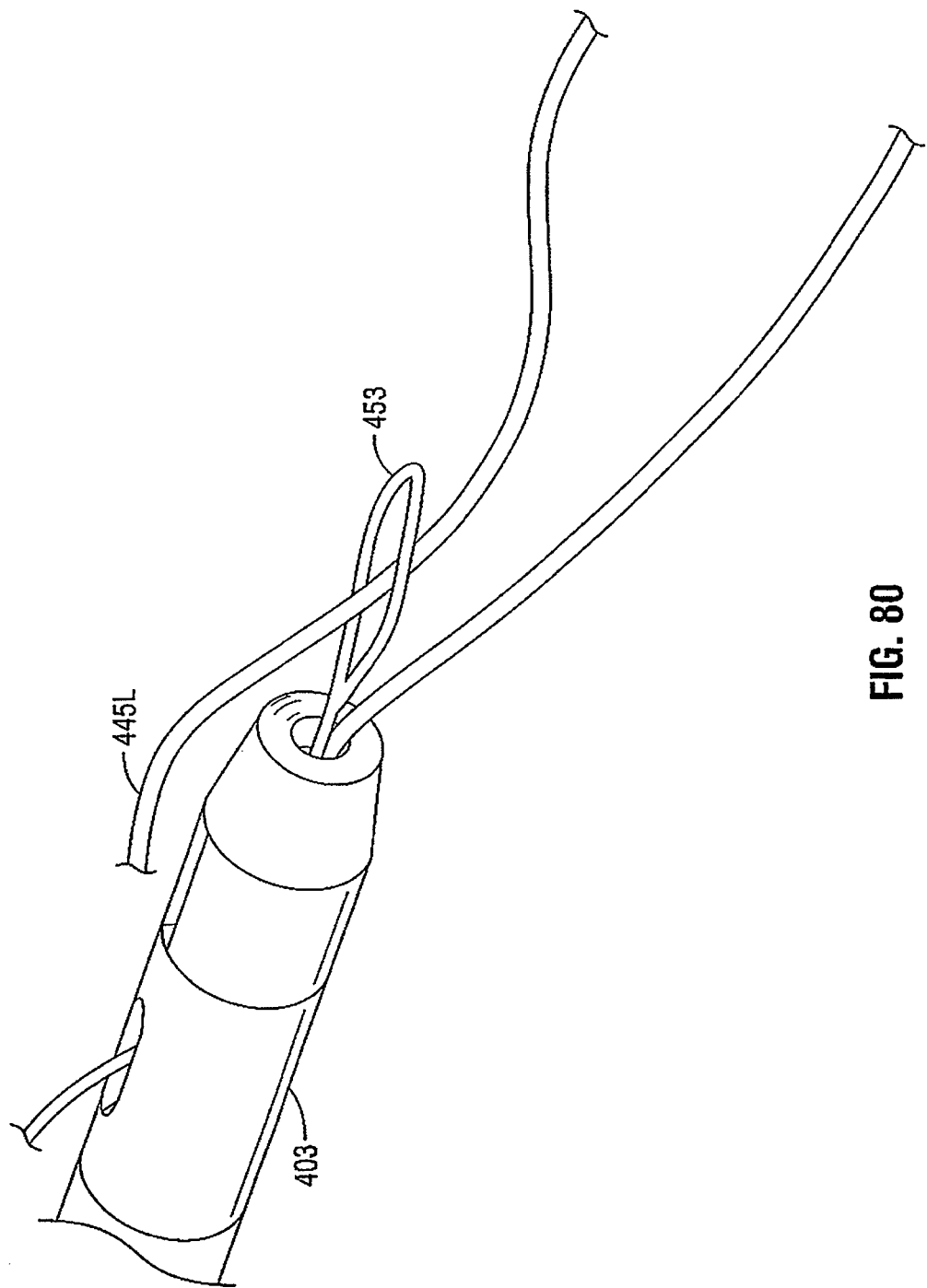
Figure 81:
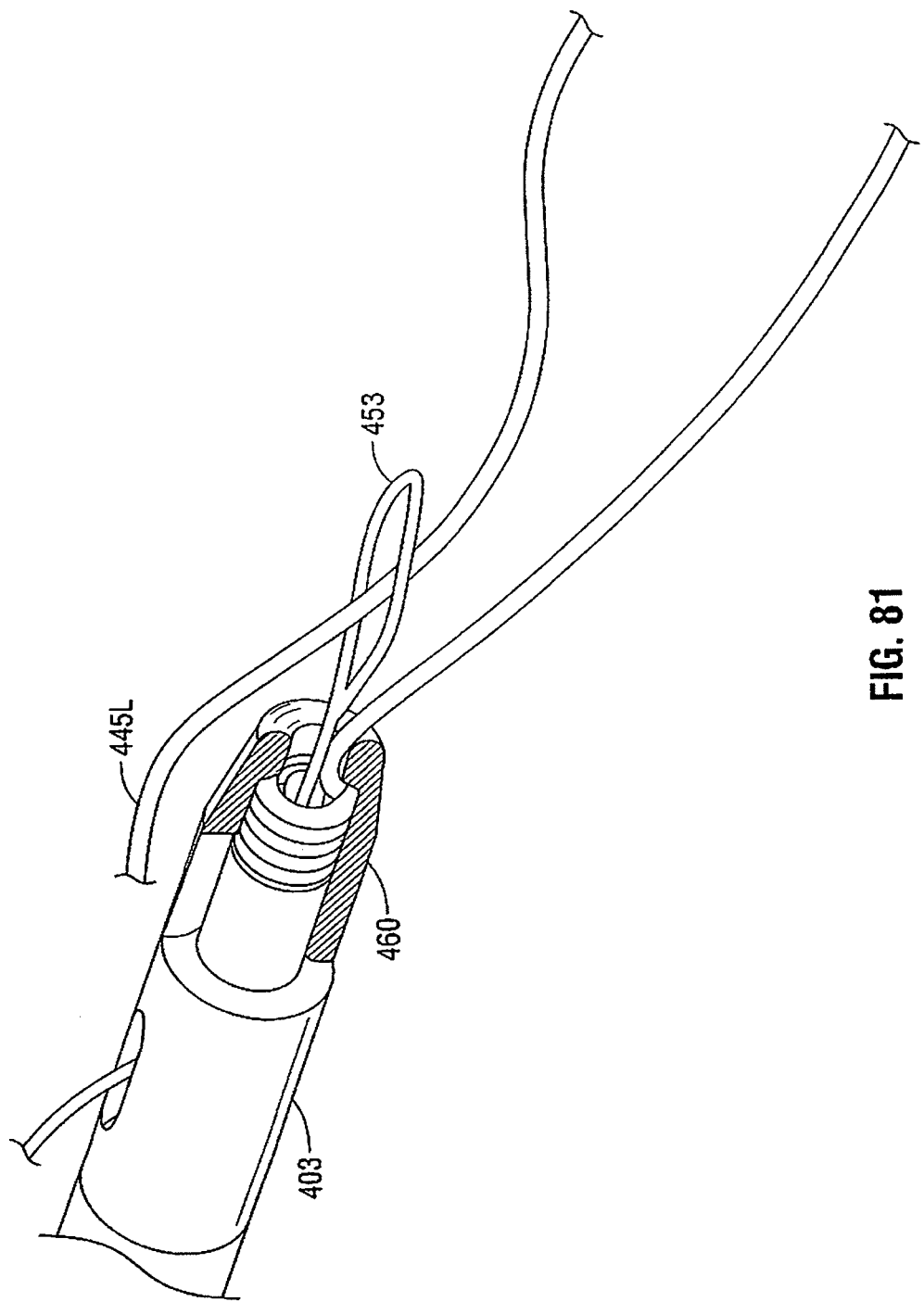
Figure 82:
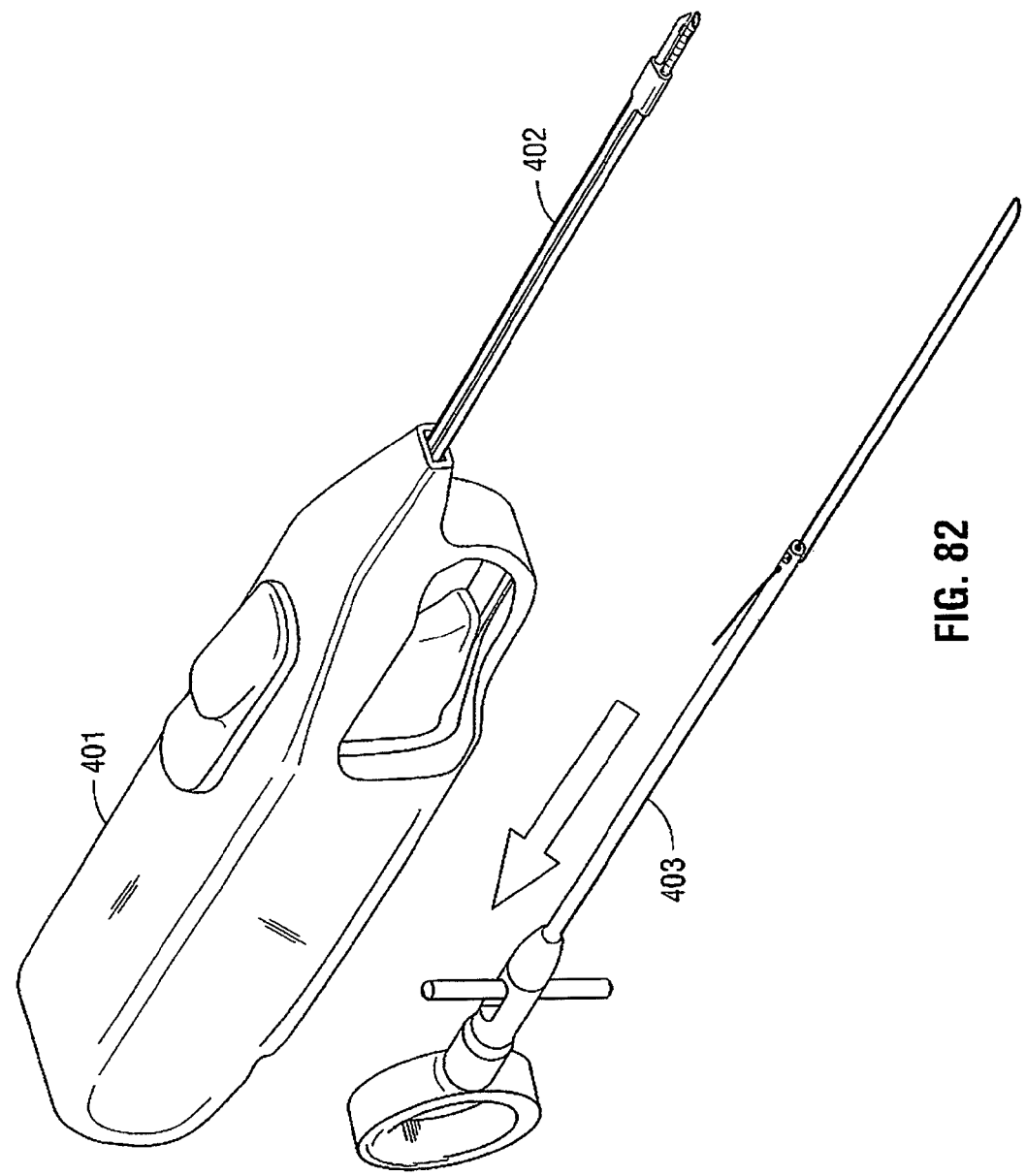
Figure 83:
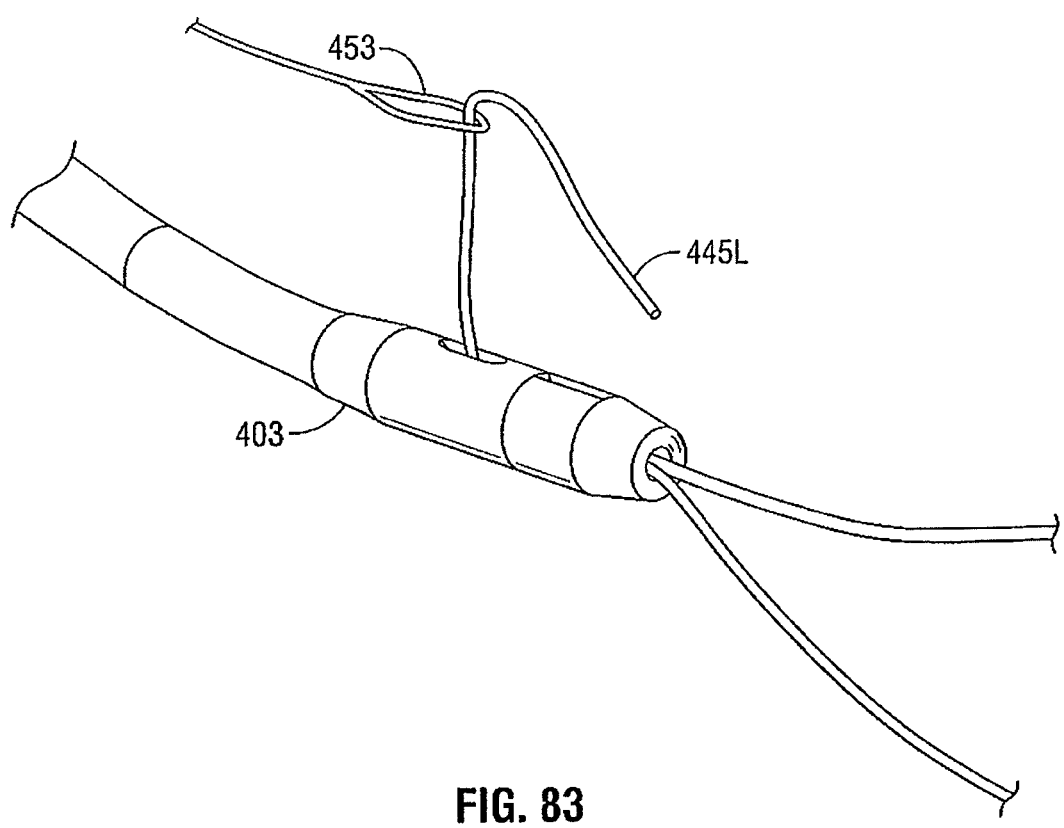
Figure 84:
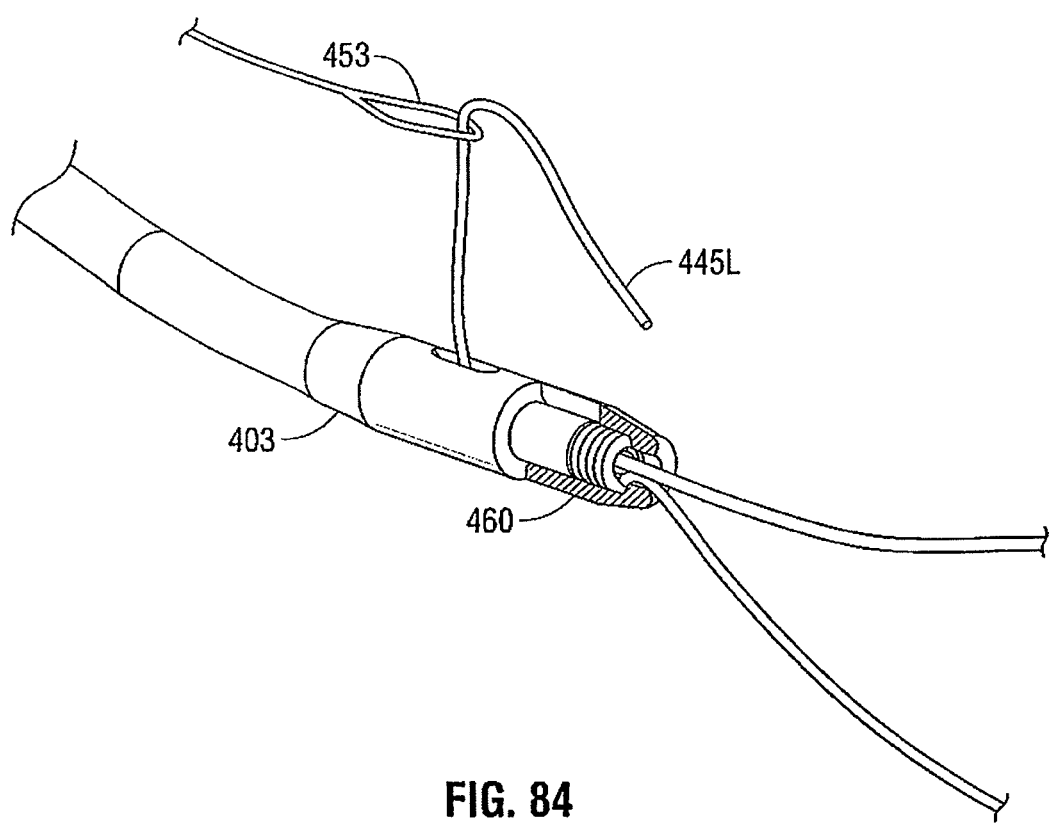

Next, the suture is tied down so as to close the tear in the meniscus. This may be done in a variety of ways which will be apparent to those skilled in the art in view of the present disclosure. In one preferred form of the invention, this is accomplished in the following way. Looking now at FIGS. 76 and 77, pusher/cutter 403 is ready to receive leading portion 445L of suture 445. Then, as shown in FIGS. 78-81, leading portion 445L of suture 445 is inserted into a loop 453 of pusher/cutter 403. Again, loop 453 of pusher/cutter 403 essentially comprises a conventional suture threader component, or needle threader component, in the sense that a collapsible loop is formed at the end of a pullable shaft. Then pusher/cutter 403 is detached from handle 401, carrying leading portion 445L of suture 445. Next, leading portion 445L of suture 445 is passed through a pre-formed, uncinched knot 460 disposed at the tip of pusher/cutter 403 (FIGS. 82-84). It will be appreciated that as leading portion 445L of suture 445 is passed through pre-formed, uncinched knot 460, the suture passes back through itself.

Figure 85:
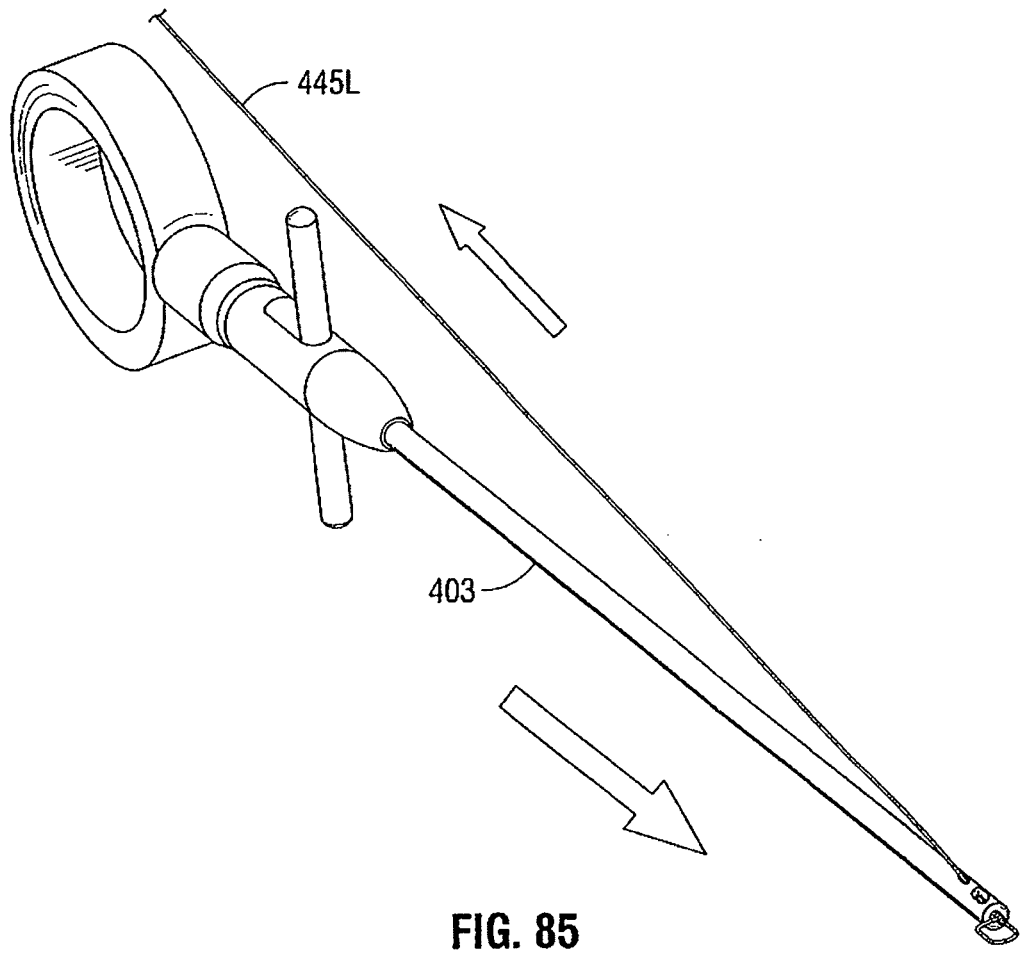
Figure 86:
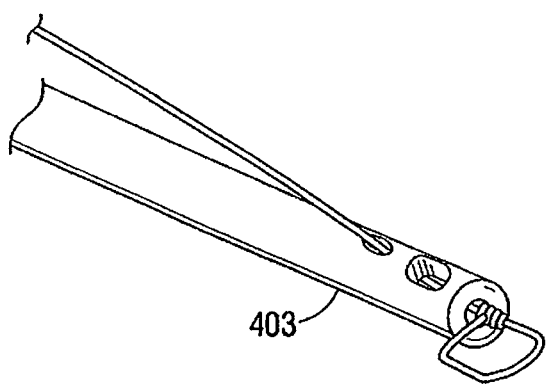
Figure 87:
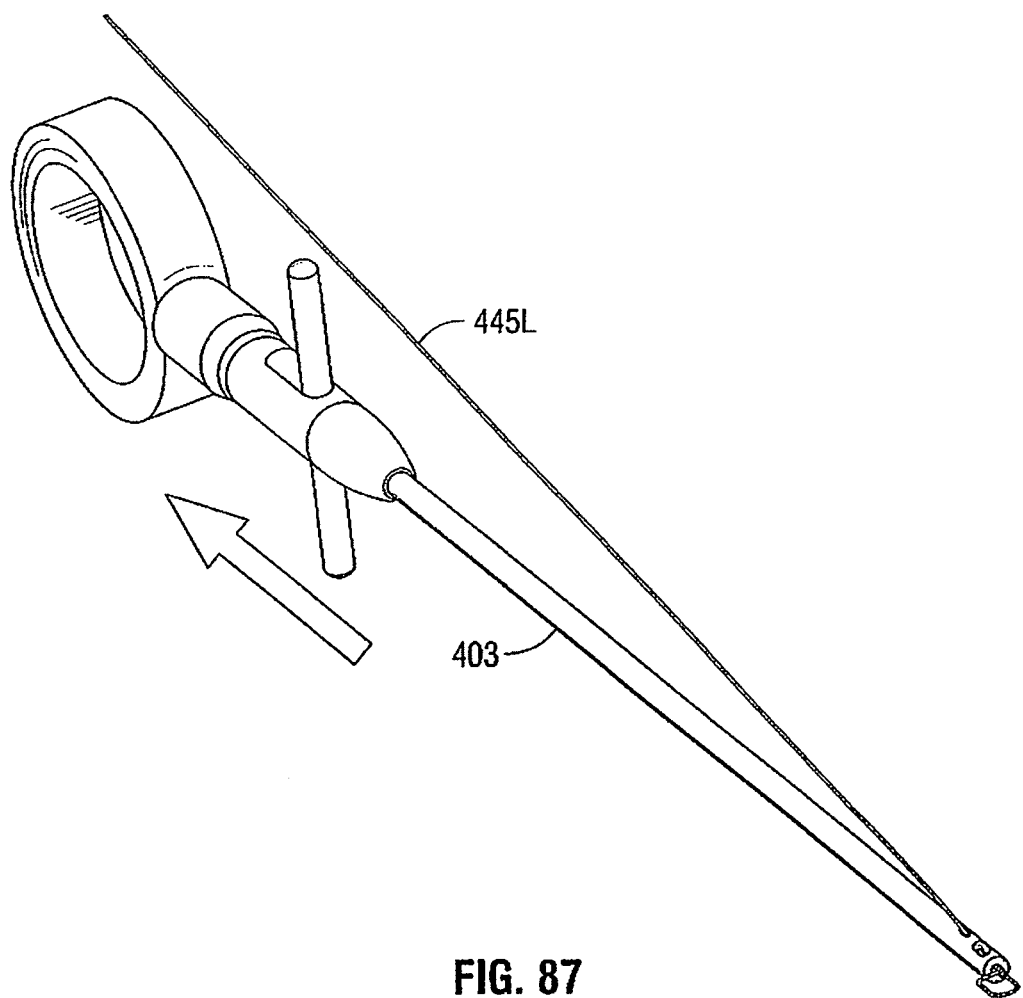
Figure 88:
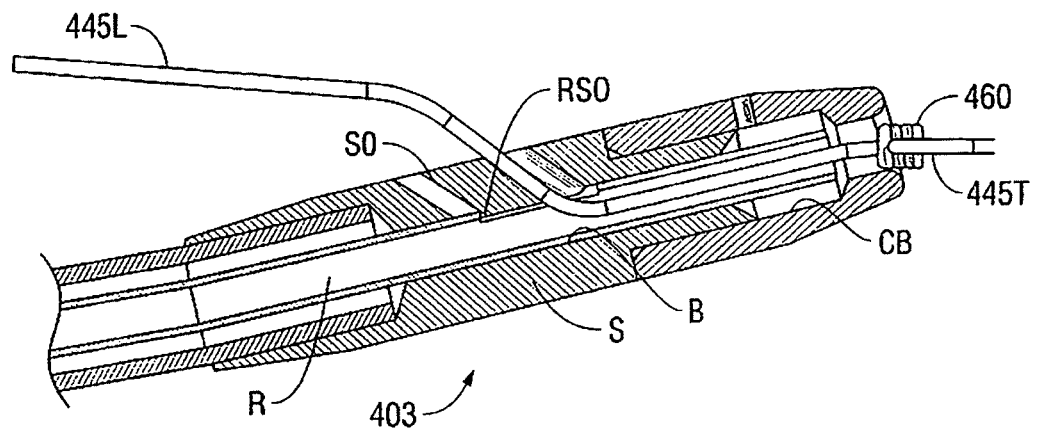
Figure 89:
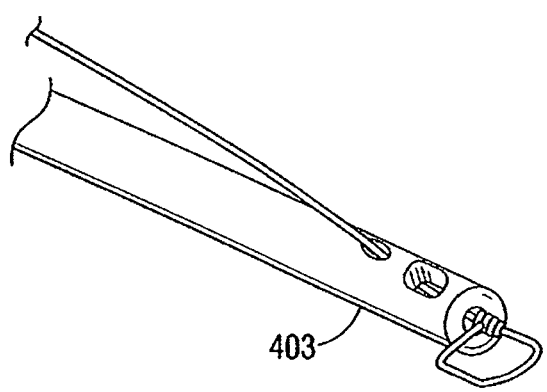
Figure 90:
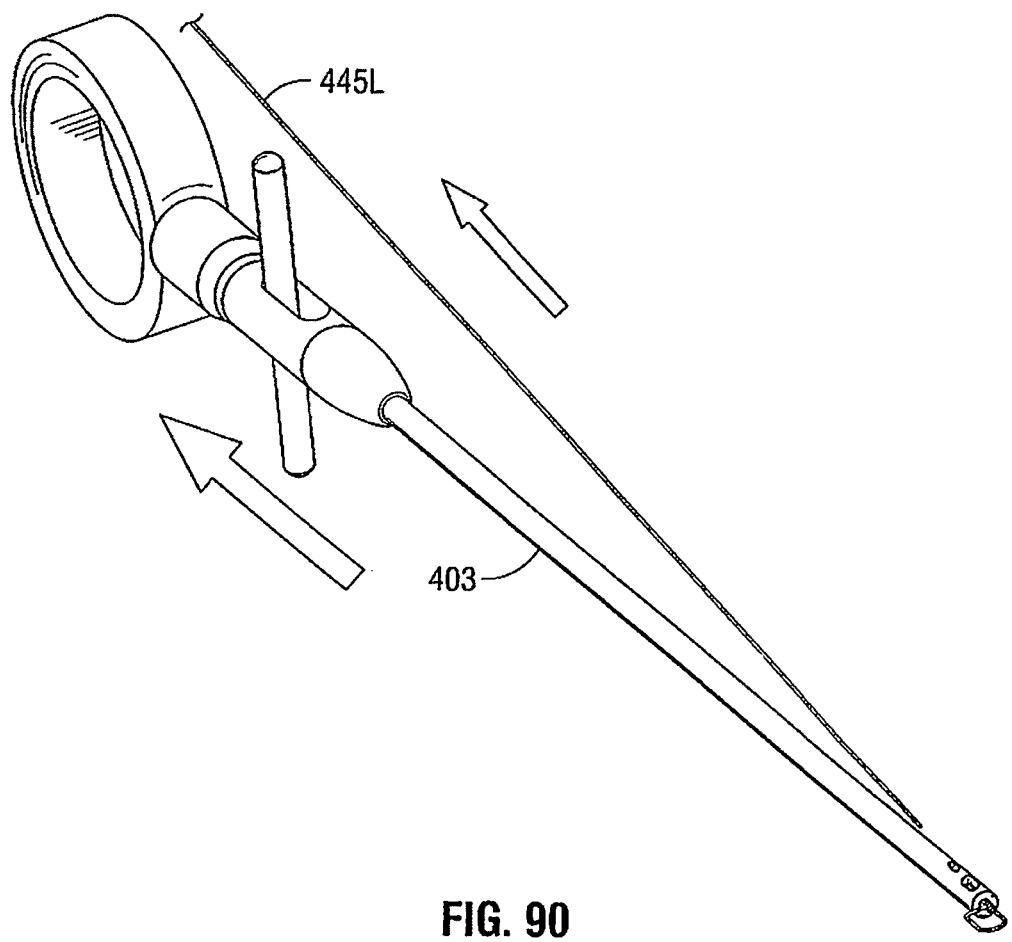
Figure 91:
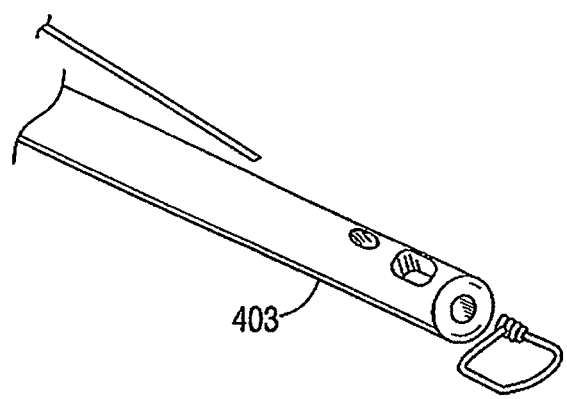
Figure 92:
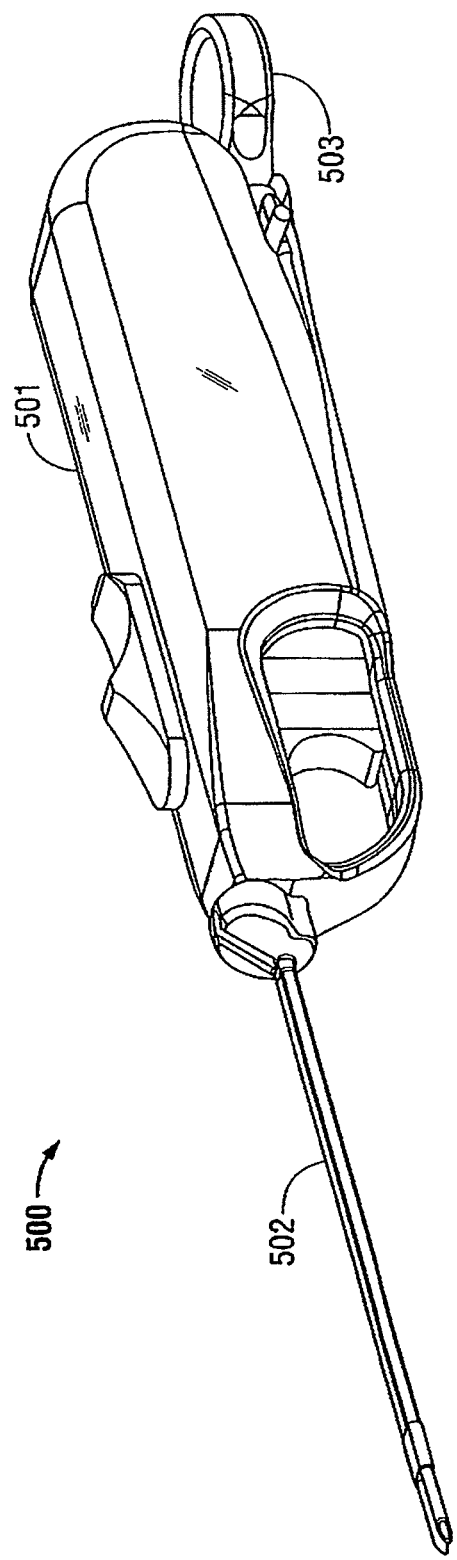
Figure 93:
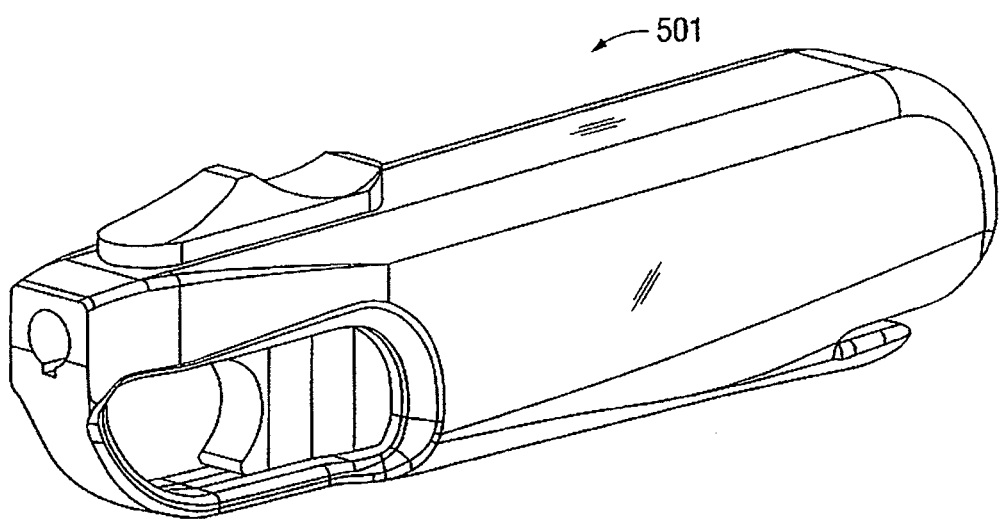
Figure 94:
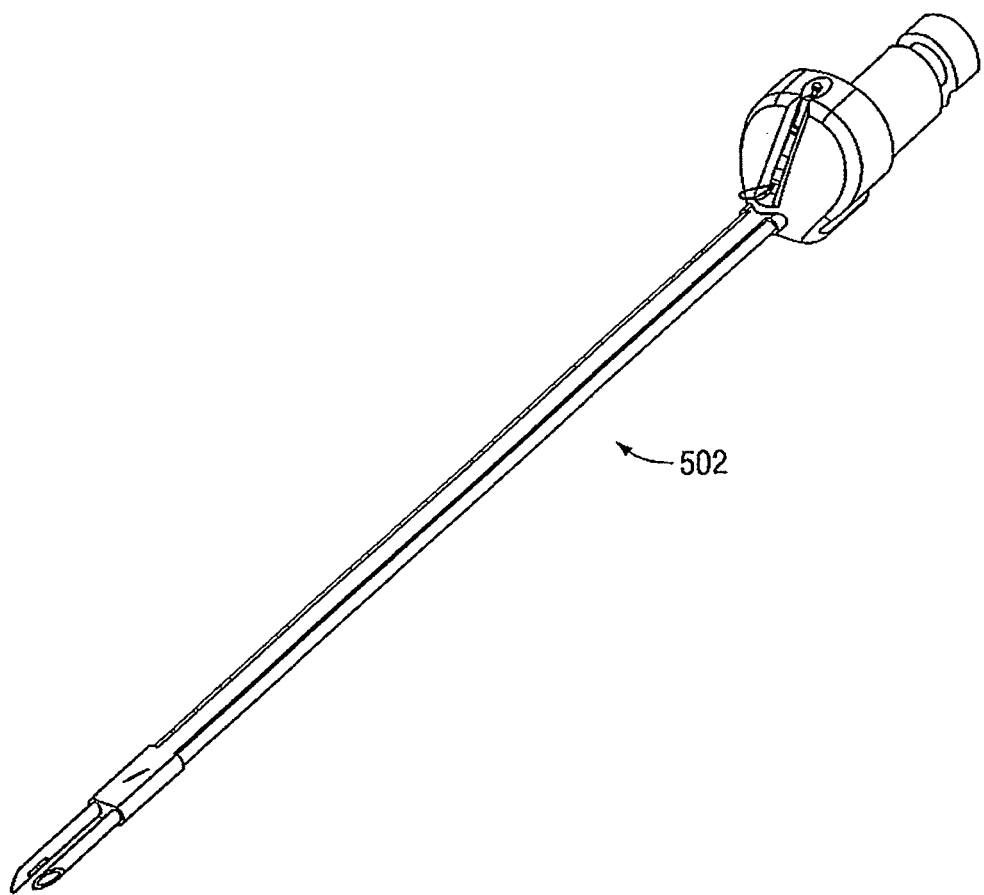
Figure 95:
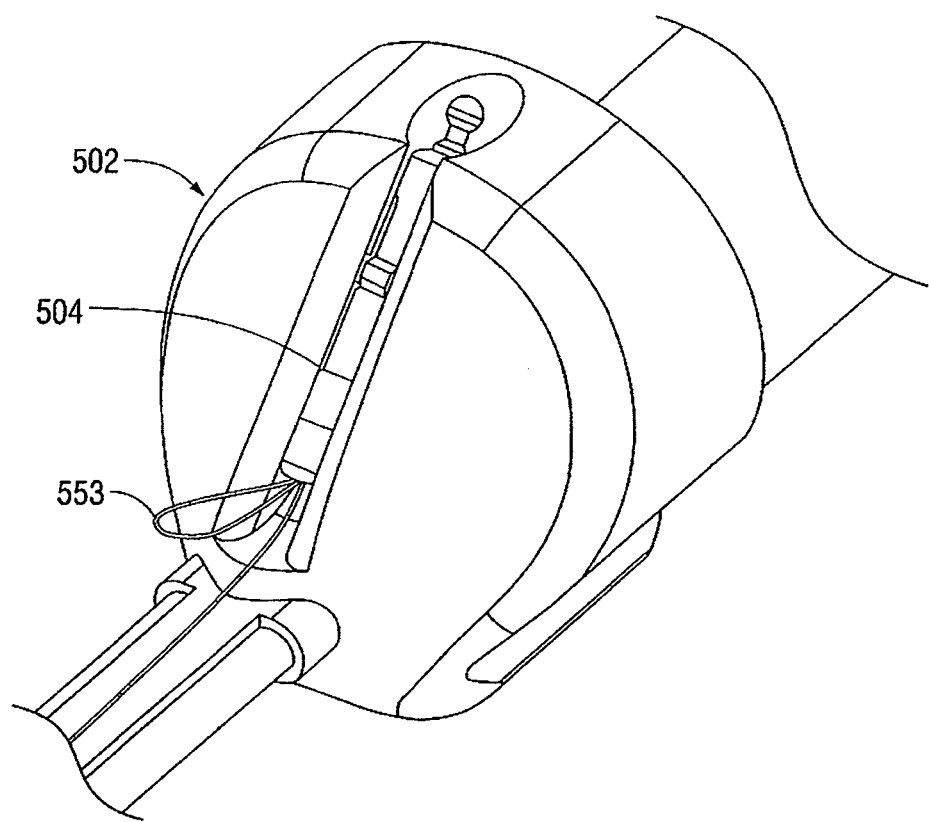
Figure 96:
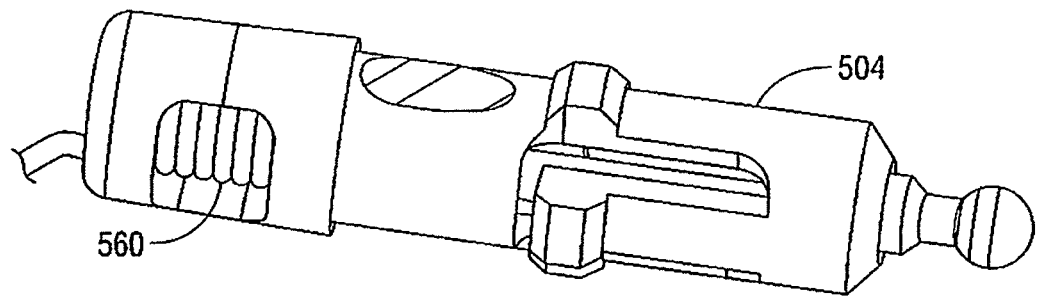
Figure 97:
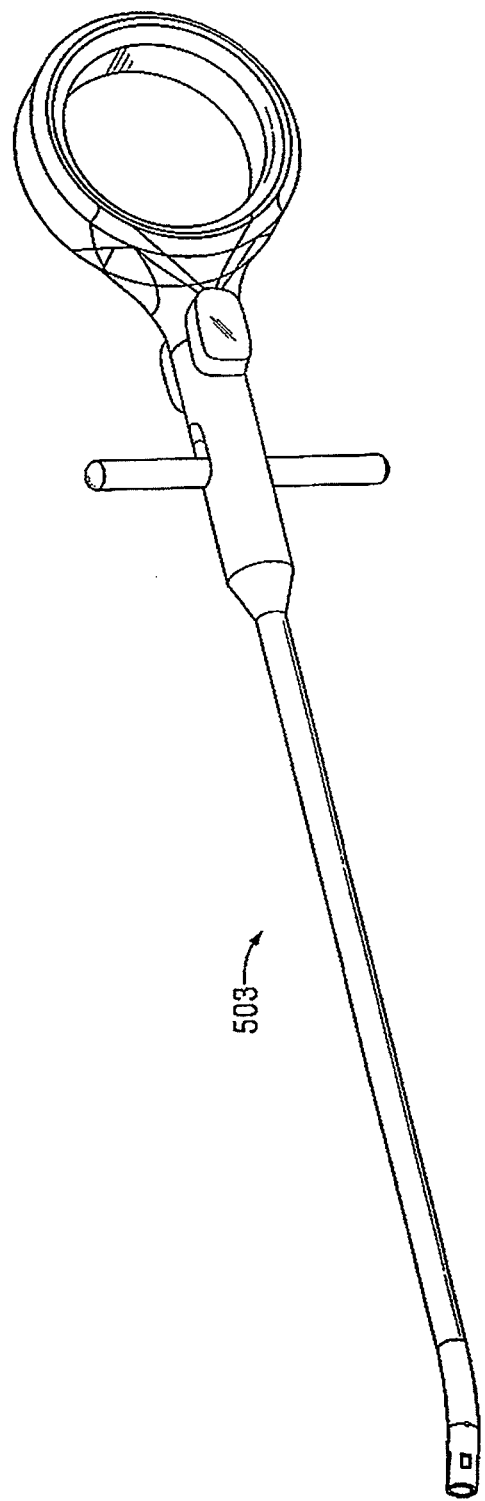

Then, and looking now at FIGS. 85 and 86, pusher/cutter 403 is advanced distally so as to bring pre-formed, un-cinched knot 460 to the near side surface of the meniscus. Next, as shown in FIGS. 87-89, the pre-formed knot is tightened. Then leading portion 445L of suture 445 is trimmed away by pusher/cutter 403 (FIGS. 90 and 91). Finally, pusher/cutter 403 is removed, leaving suture 445 closing the tear in the meniscus with a low-profile suture fixation.

In one preferred form of the invention, and looking now at FIG. 88, pusher/cutter 403 comprises a shaft S having a central bore B, a counterbore CB and a side opening SO. A hollow ram R, having a ram side opening RSO, is slidably disposed within bore B of shaft S. Prior to knot deployment, the pre-formed, uncinched knot 460 is seated within counterbore CB; and after leading portion 445L of suture 445 is passed through pre-formed, uncinched knot 460, leading portion 445L is drawn through ram side opening RSO and shaft side opening SO; and when the knot is to be separated from shaft S, ram R is moved distally, first pushing the knot out of the shaft and, after cinching, thereafter cutting leading portion 445L of suture 445 by virtue of moving side opening SO out of alignment with ram side opening RSO.

In one preferred form of the invention, the cinched knot is separated from shaft S in a first discrete step, and then the suture is cut in a second discrete step.

Fifth Preferred Method and Apparatus

In yet another preferred form of the present invention, the pre-formed, uncinched knot can be stored in a disposable tip that is releasably mounted to the needles, with the needles themselves being releasably mounted to the handle, and with the disposable tip being connectable to a pusher after the suture has been passed through the tissue. This construction has the advantage that (i) a single handle can be used for both the needles and pusher, and (ii) a single handle and a single pusher can be provided even where a patient may require multiple stitches (i.e., multiple disposable tips with multiple pre-formed, uncinched knots).

More particularly, and looking now at FIGS. 92-97, there is shown an apparatus 500 for use in closing tear 20 in meniscus 5. Apparatus 500 generally comprises a handle 501, a needle cartridge 502, and a pusher 503. Needle cartridge 502 includes a disposable tip 504 which contains the pre-formed, uncinched knot 560. Specific details of the construction and function of handle 501, needle cartridge 502, pusher 503 and disposable tip 504 will be disclosed in the course of the following discussion of using apparatus 500 to close tear 20 in meniscus 5.

The apparatus 500 is prepared for use by mounting needle cartridge 502 mounted to handle 501, and mounting pusher 503 to handle 501 (FIG. 98).

Figure 99:
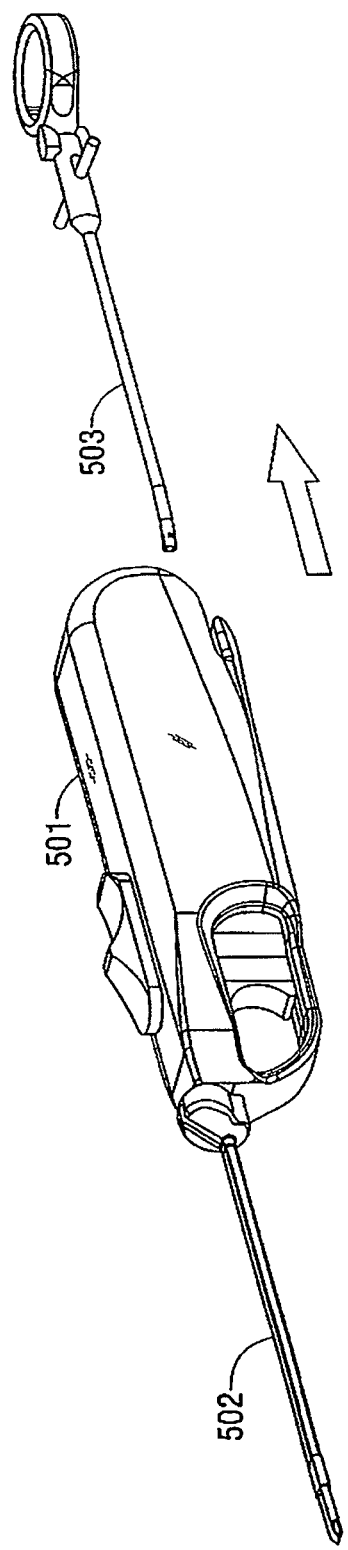
Figure 100:
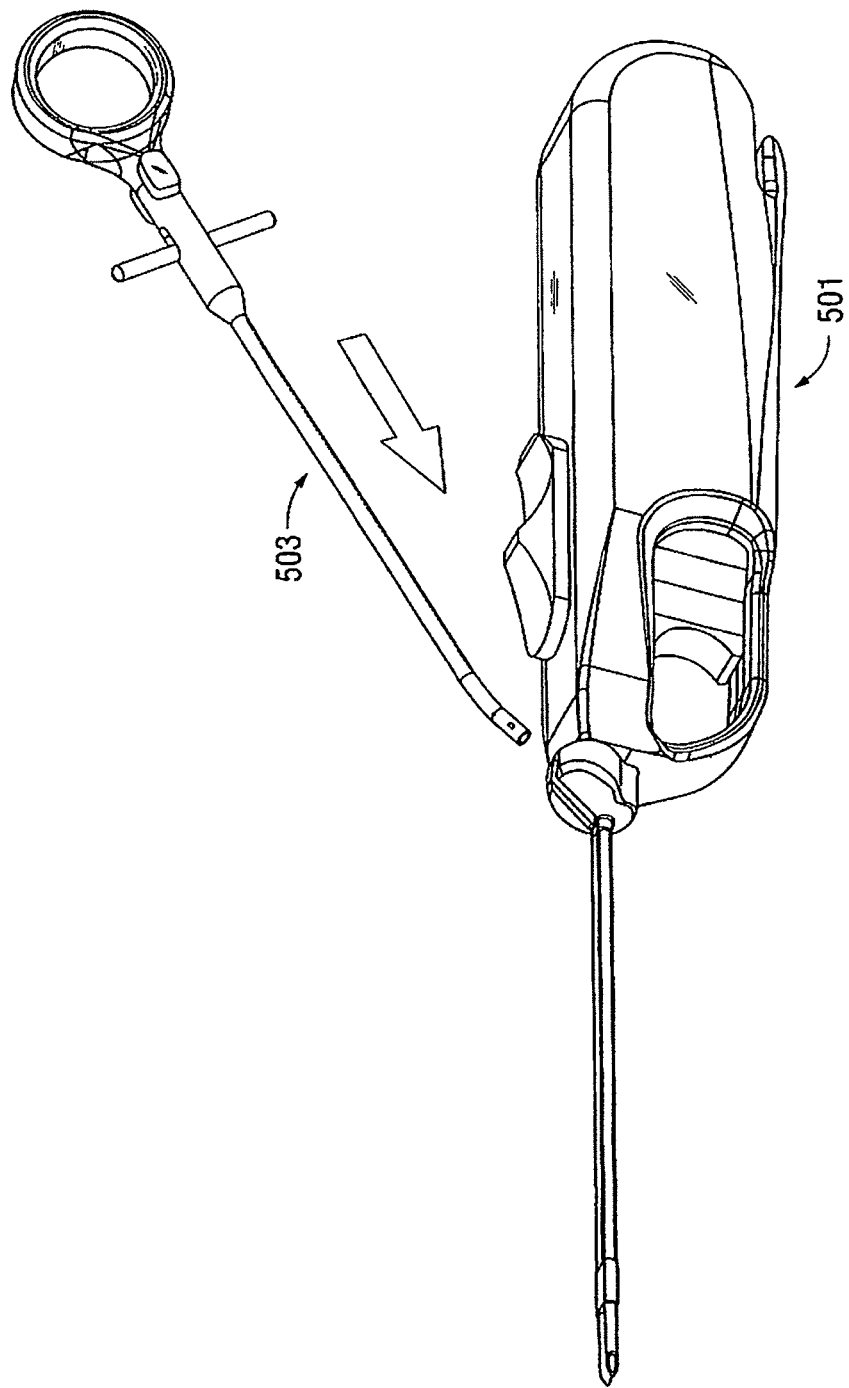
Figure 101:
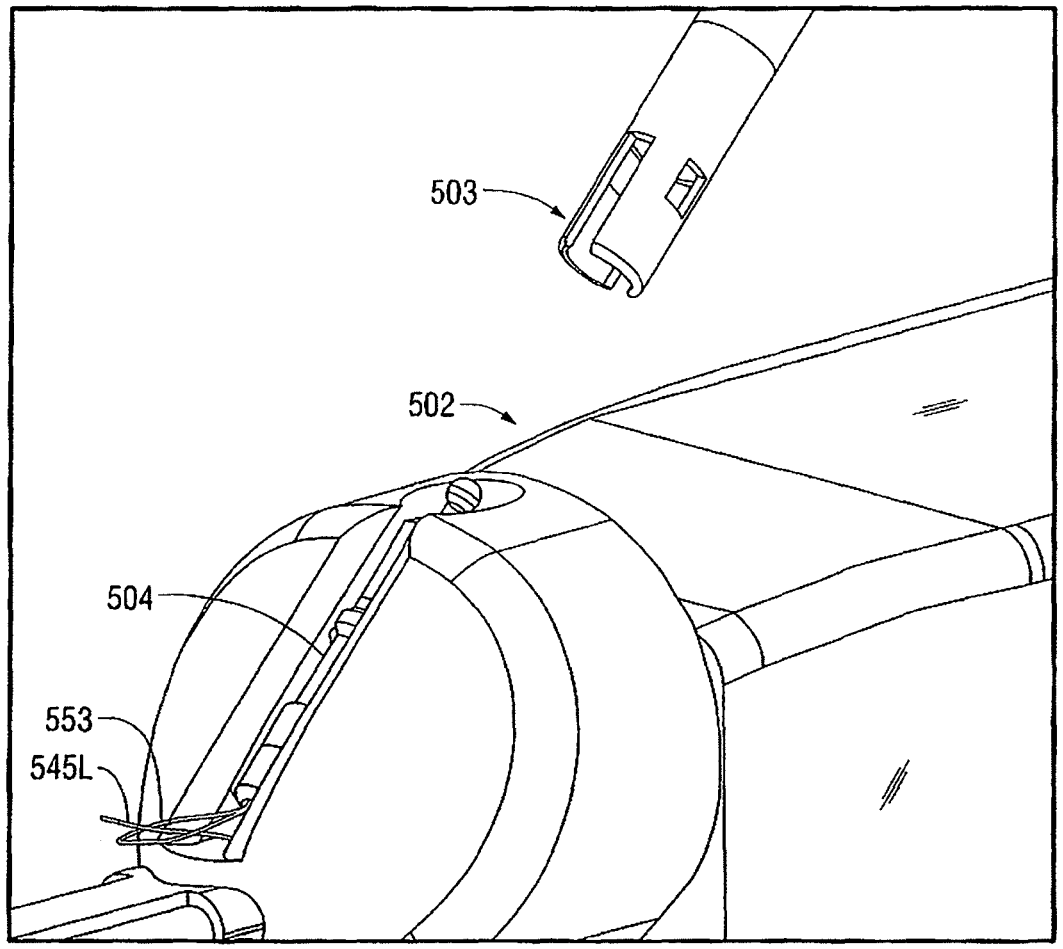
Figure 102:
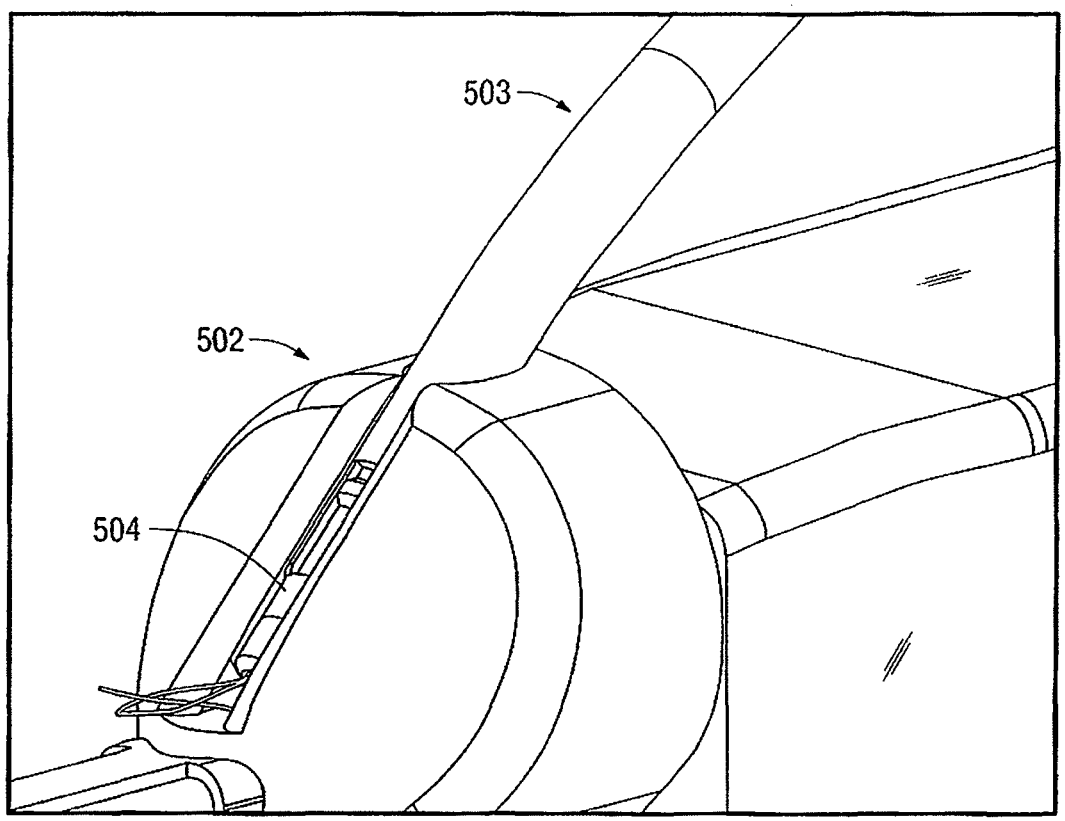
Figure 103:
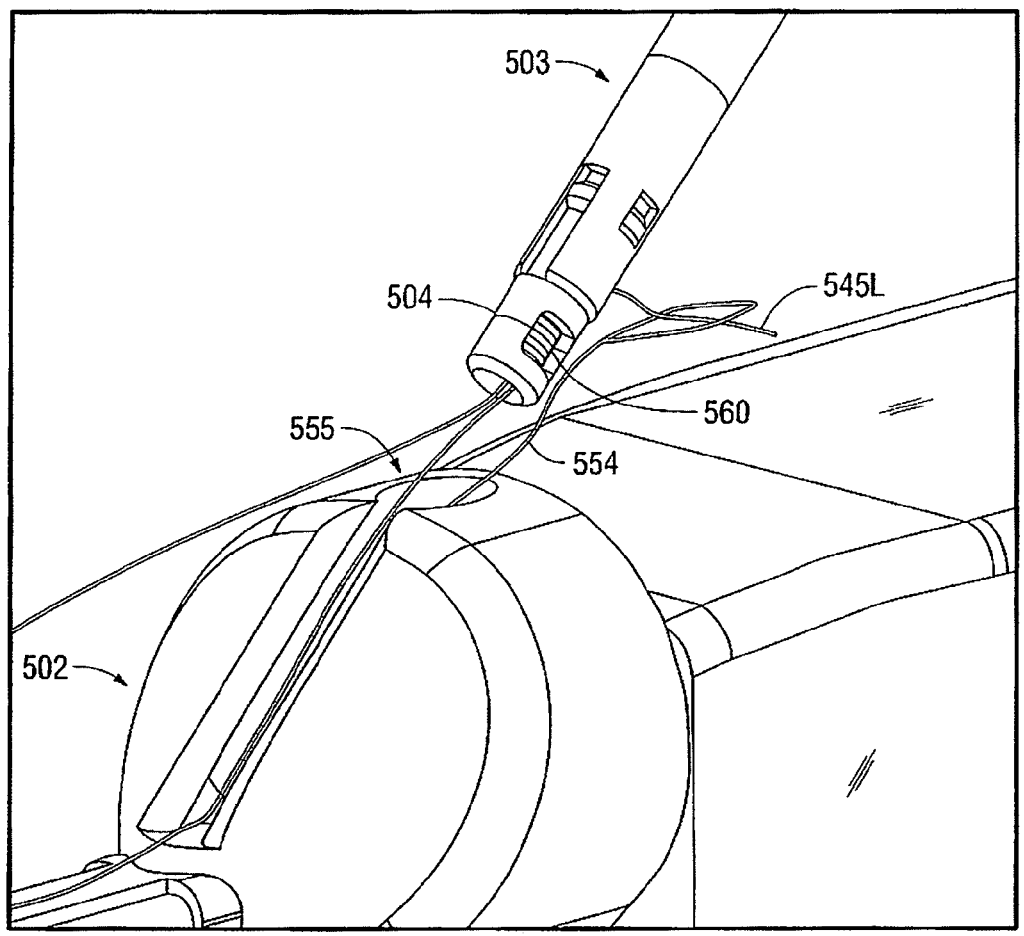

Apparatus 500 utilizes the same suture passing approach as apparatus 400 in order to pass and retract the leading portion of the suture from the near side of the meniscus to the far side of the meniscus and then back. Once the leading portion 545L of suture 545 is retracted to the near side of the meniscus, leading portion 545L of suture 545 is threaded into loop 553 of a snare 554. Snare 554 in turn extends through the body of disposable tip 504, including through pre-formed, uncinched knot 560, and exits disposable tip 504 before being attached to needle cartridge 502 at 555. Then, pusher 503 is detached from handle 501 (FIG. 99) and is brought down into engagement with disposable tip 504 (FIGS. 100-102). Pusher 503 is then withdrawn, carrying disposable tip 504 with it. As disposable tip 504 is withdrawn from needle cartridge 502, snare 554 is pulled back through the retreating disposable tip 504 thereby threading suture 545L through pre-formed, uncinched knot 560. Thereafter, suture 545 is secured in the manner previously discussed.

Sixth Preferred Method and Apparatus

Figure 104:
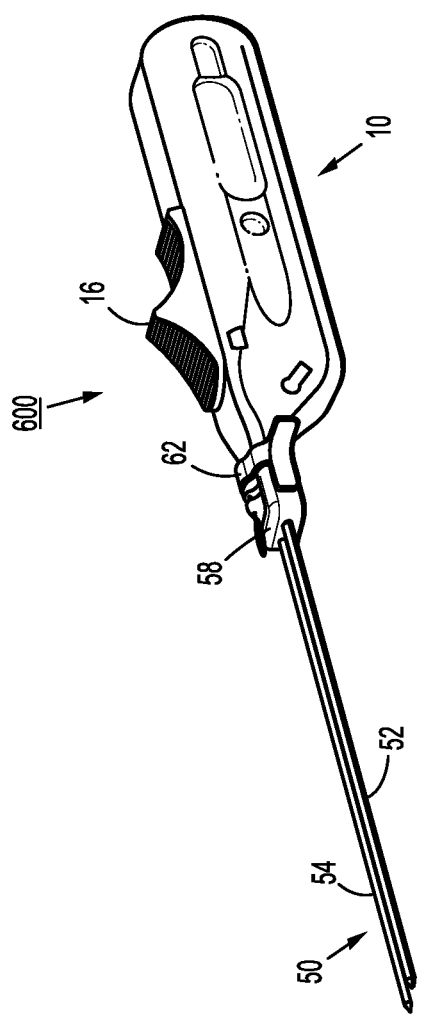
FIG. 104 is a perspective view of a meniscal repair device.
Figure 117:
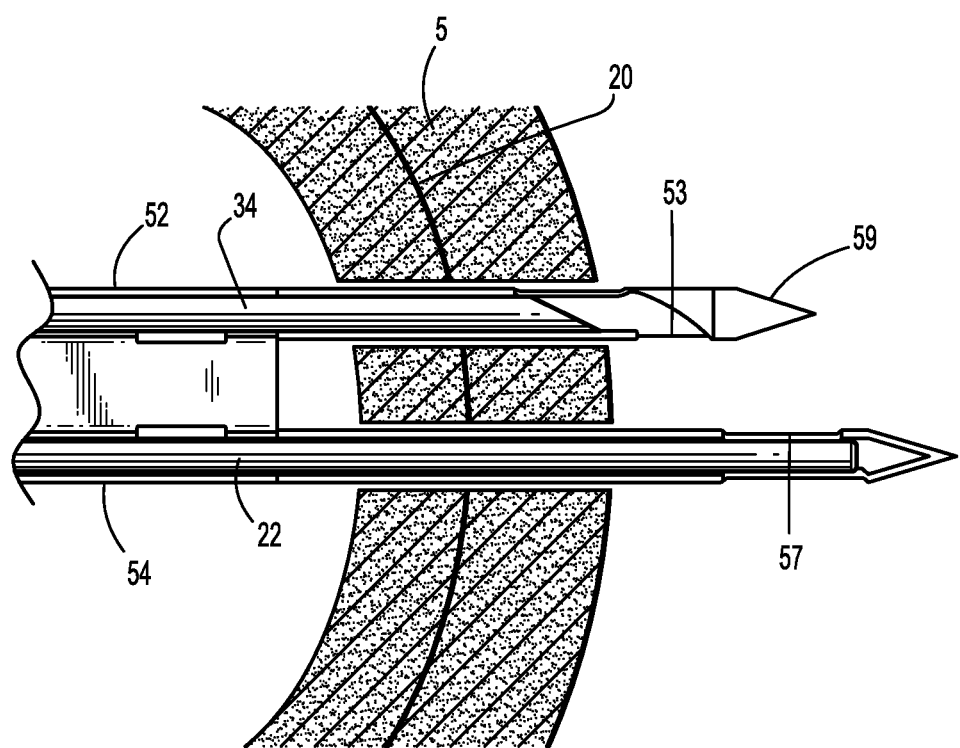
FIG. 117 is a top cross-sectional view of the needle cartridge of FIG. 114 inserted through a meniscus.
Figure 118:
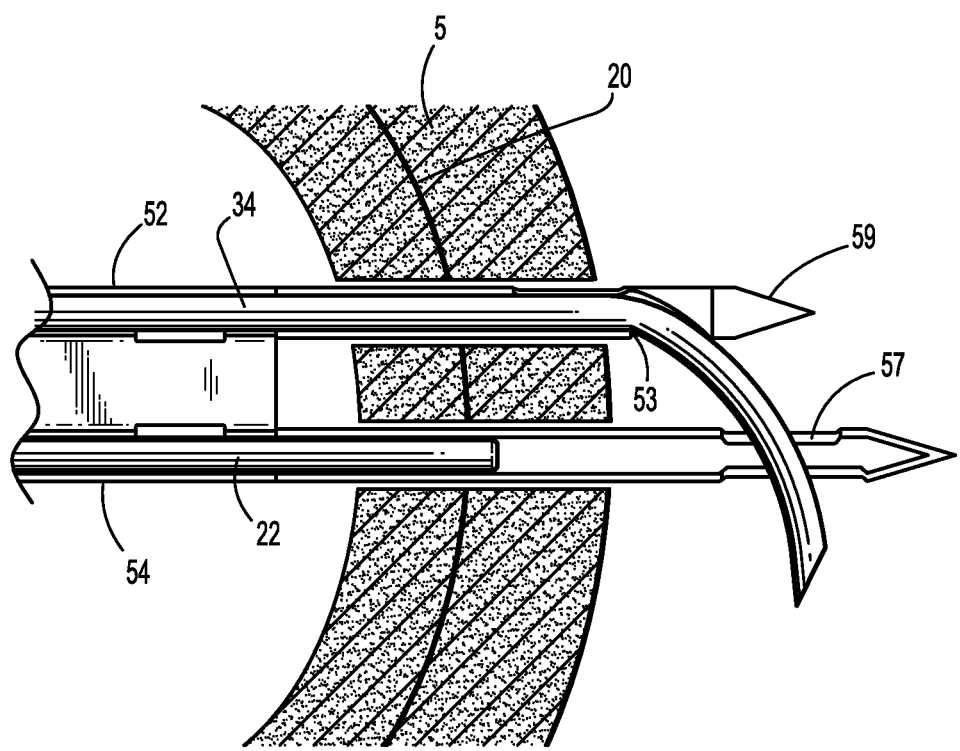
FIG. 118 is a top cross-sectional view of the needle cartridge of FIG. 114 inserted through a meniscus with illustrating a needle extended and an obturator retracted.

Turning now to FIG. 104, there is shown an apparatus 600 for use in closing tear 20 in meniscus 5. The apparatus 600 is pre-loaded with a length of suture material having a pre-formed knot at a first end that, in use, is passed from a suture feed needle 52 to the suture catch needle 54 and is passed through meniscus 5 surrounding tear 20 as determined by a patient's anatomy, as shown in FIGS. 117 and 118.

Figure 105:
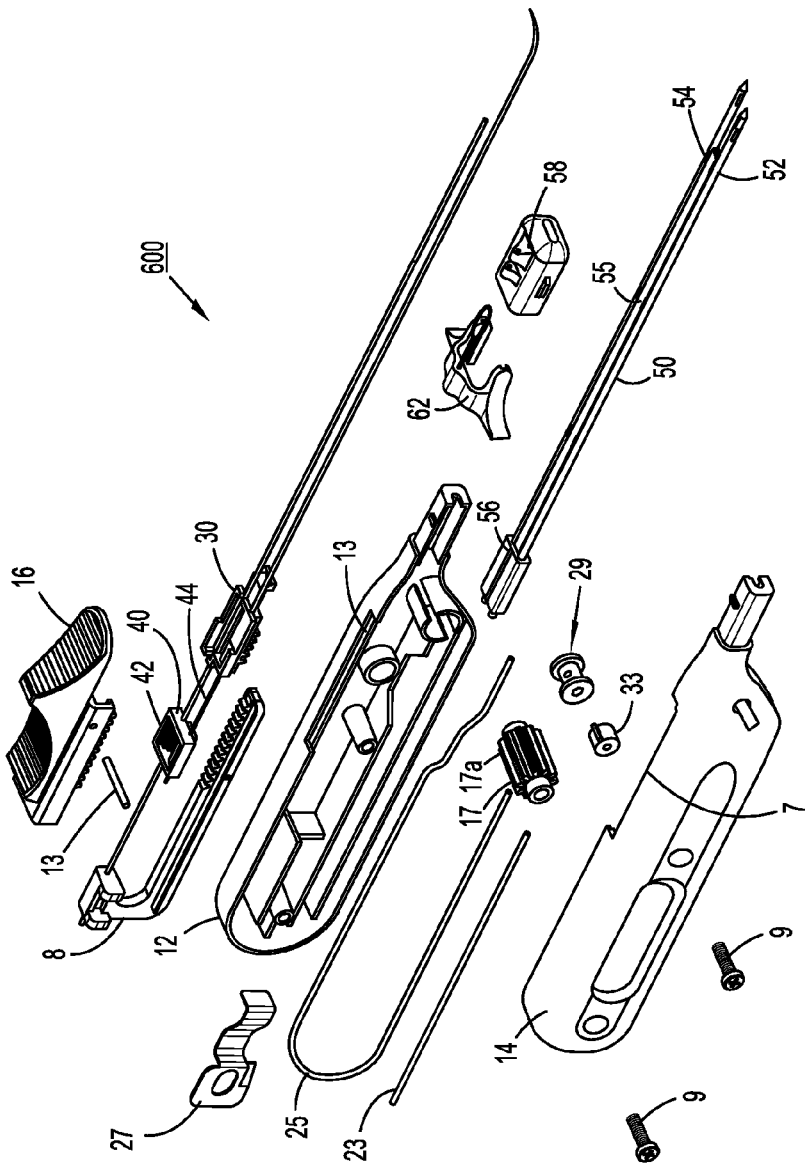
FIG. 105 is an exploded perspective view, with parts separated, of the meniscal repair device of FIG. 104.

As seen in FIG. 105, the apparatus 600 includes a handle 10 that includes a left handle portion 12 and a right handle portion 14 that are attached to each other using fasteners 9. A thumbslide 16 is positioned on a top surface of the handle 10, as shown in FIG. 104. The thumbslide 16 is slidable in a slot defined by opposing recesses 13, 7 formed in the left and right handle portions 12, 14 along the longitudinal axis of the handle 10. The thumbslide 16 has a U-shaped member attached to its bottom surface. Two rows of teeth are disposed along the bottom edges of the U-shaped member. A gear 17 having a plurality of teeth 17a is rotatably supported in the handle 10 between the left and right handle portions 12, 14. The teeth 17a of the gear 17 mesh with teeth 16a of the thumbslide 16, as shown in FIG. 108, such that longitudinal movement of the thumbslide 16 results in rotational motion of the gear 17.

A suture spool 29 is rotatably disposed in the apparatus 600 and holds a quantity of the suture material. A tension spring 33 is operably coupled to the suture spool 29 and applies a predetermined amount of tension to the suture spool 29 and applies a predetermined amount of tension to the suture that is wound around the suture spool 29 such that when the physician pulls on the suture material when withdrawing it from the apparatus 600, the tension spring 33 provides some resistance such that the suture material may be withdrawn in a controlled manner. It is also contemplated that a foam disc may be substituted for the tension spring 33. A lockout spring 27 interacts with an obturator rack 8, as will be discussed in detail hereinbelow. The apparatus 600 also includes a generally U-shaped tube 25 and a generally straight tube 23 for retaining a portion of the length of suture material. It is also contemplated that a foam disc may be substituted for the tension spring 33.

As seen in FIG. 104, needle cartridge 50 is fixedly attached at the distal end of the handle 10 using a hub 56 at the proximal end of the needle cartridge 50. The needle cartridge 50 includes two laterally spaced apart needles including a suture feed needle 52 and a suture catch needle 54. At the distal ends of the suture feed needle 52 and the suture catch needle 54 are tips 52t, 54t. The tips 52t, 54t are configured and adapted to penetrate soft body tissue, i.e., the tips 52t, 54t are pointed. As shown in FIG. 106, the tips 52t, 54t may have a directional orientation that is straight. However, other directional orientations are contemplated and may be selected depending upon a patient's anatomy. For example, a suture feed needle 52a and a suture catch needle 54a including tips 52 at, 54 at that are oriented upwards with respect to the longitudinal axes of the suture feed needle 52a and the suture catch needle 54a, respectively, are shown in FIG. 107. The tips of the needles may also either be oriented to the left or may be oriented to the right. As shown in FIGS. 106 and 107, both the suture feed needle 52 and the suture catch needle 54 include open proximal ends that are coupled to the handle 10 and closed distal tips.

Figure 108:
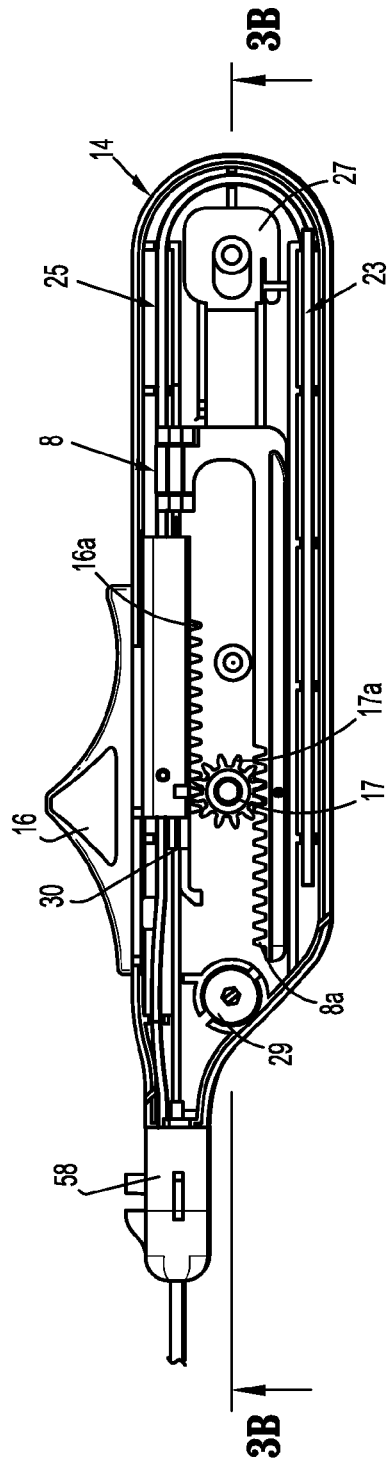
FIG. 108 is a side view of the proximal portion of the meniscal repair device of FIG. 104 with the left handle portion removed.
Figure 109:
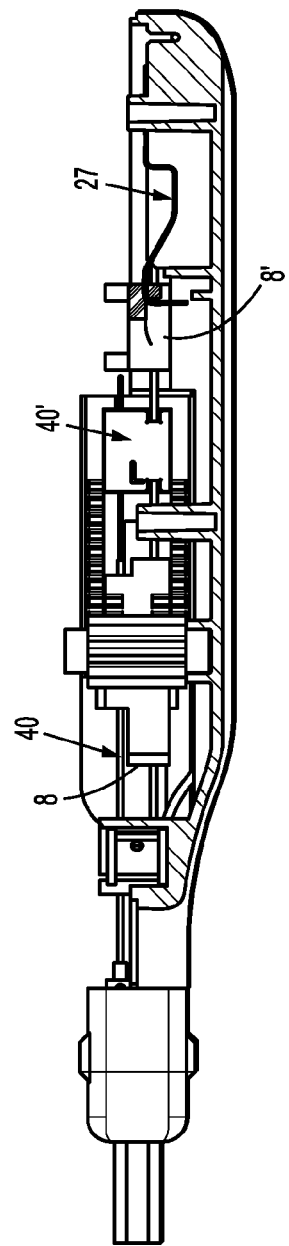
FIG. 109 is a top cross-sectional view of the meniscal repair device of FIG. 104 with the right handle portion removed.
Figure 110:
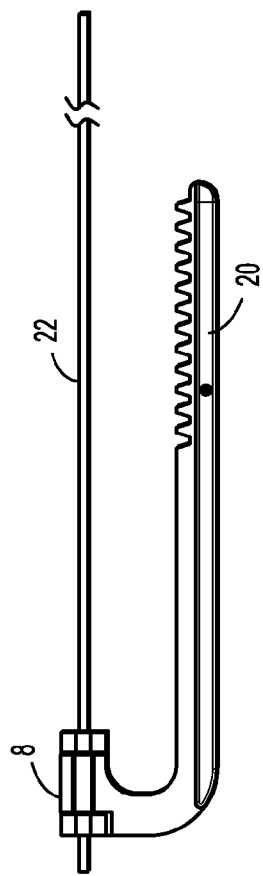
FIG. 110 is a side view of an obturator rack having an obturator disposed therein.

As shown in FIG. 108, the obturator rack 8 is slidably positioned in the bottom region of the handle 10 and includes a plurality of teeth 8a that mesh with the teeth 17a of the gear 17 such that rotation of the gear 17 results in longitudinal movement of the obturator rack 8. An obturator 22 extends distally from the obturator rack 8, as shown in FIG. 110. When the thumbslide 16 is retracted proximally to extend the obturator 22 distally through the catch needle 54, a lockout spring 27 (FIGS. 105, 108, and 109) engages a proximal portion 8' of the obturator rack 8 and inhibits the obturator rack 8 from inadvertently moving distally through the apparatus 600. In addition, the arrangement of the gear 17 and the obturator rack 8 inhibits further actuation of the thumbslide 16.

Figure 111:
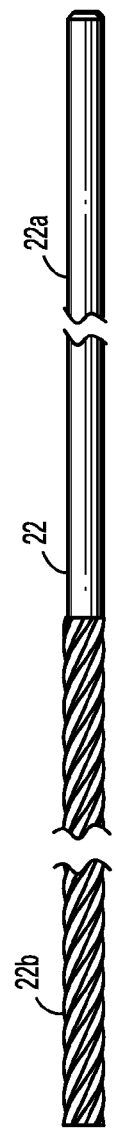
FIG. 111 is a side view of the obturator of FIG. 110.

As seen in FIG. 111, the obturator 22 includes a solid proximal portion 22a and a braided distal portion 22b. The braided distal portion 22b is configured and adapted to follow the path of the suture catch needle 54. The braided distal portion 22b is relatively flexible and experiences less friction against the inner wall of the suture catch needle 54, the braided distal portion 22b.

Figure 112:
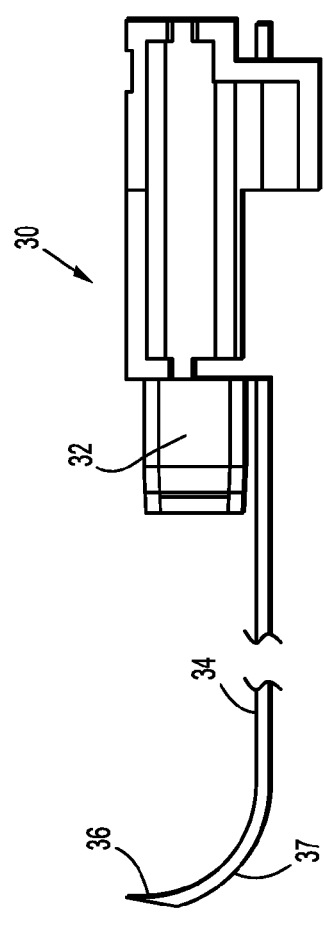
FIG. 112 is a top view of a needle assembly.
Figure 113:
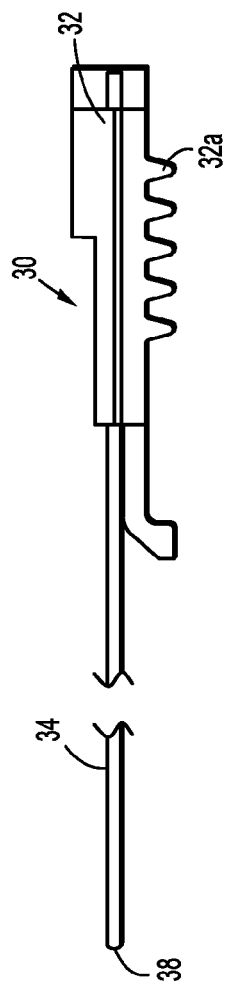
FIG. 113 is a side view of the needle assembly of FIG. 112.

As shown in FIGS. 112 and 113, the apparatus 600 includes a needle assembly 30 including a needle rack 32 and a shape memory needle 34 extending distally therefrom. The shape memory needle 34 is formed from a shape memory material such as nitinol. The shape memory needle 34 has an opening 38 at its distal end for receiving the pre-formed suture end at a first end of the suture. The open distal end 38 of the shape memory needle 34 is beveled to define a sharp end for penetrating soft tissue. The shape memory needle 34 has shape memory properties such that, in its unstressed state, an end region 37 of the shape memory needle 34 is curved relative to the longitudinal axis of the shape memory needle 34. The needle rack 32 is positioned in a bottom portion of the U-shaped member of the thumbslide 16 such that it may translate proximally and distally in conjunction with the thumbslide 16. A plurality of teeth 32a is disposed along a bottom surface of the needle rack 32. The plurality of teeth on the needle rack 32 mesh with the teeth of the gear 17 for effectuating reciprocal motion along the longitudinal axis of the handle 10 in conjunction with movement of the thumbslide 16.

An ejector wire assembly 40, shown in FIG. 105, includes a hub 42 and an ejector wire 44 extending therefrom. The proximal position of the ejector wire assembly 40 is labeled as 40'. The ejector wire 44 has a solid proximal portion and a braided distal portion, similar to the obturator 22. Such a configuration facilitates the ejector wire 44 to follow the curved path of the shape memory needle 34 with minimal frictional engagement therebetween. The hub 42 is positioned longitudinally adjacent to the needle rack 32 such that the ejector wire assembly 40 may translate longitudinally in conjunction with the needle assembly 30. The ejector wire 44 is disposed coaxially within a lumen of the shape memory needle 34. In an initial position, the distal end of the ejector wire 44 is positioned slightly proximal relative to the distal end of the shape memory needle 34, by a distance sufficient to enable the enlarged end at the first end of the suture material to be loaded into and retained within the distal end of the shape memory needle 34 as described below in further detail.

The shape memory needle 34 and the ejector wire 44 are coaxially aligned and translate longitudinally through the suture feed needle 52. The obturator 22 is laterally spaced from the shape memory needle 34 and translates longitudinally through the suture catch needle 54. The distal ends of both needles 52, 54 are closed-ended, sharpened tips 52t, 54t configured and adapted to penetrate soft tissue. A window 57, as shown in FIG. 114, is defined in a distal region of the suture catch needle 54 and is proximal of the closed-ended tip 54t. In addition, the suture feed needle 52 has a slot 53 that faces towards the suture catch needle 54. The suture feed needle 52 includes an internal ramp 59 that guides the shape memory needle 34 towards the window 57. A central rectangular channel 55 is positioned between the suture feed needle 52 and the suture catch needle 54. The channel 55 includes a longitudinally extending opening 61.

A suture spool 29 is rotatably positioned within the handle 10, as shown in FIG. 105, and is pre-loaded with the length of suture material. As previously mentioned, the suture material includes an enlarged end at a first end of the suture material that is initially disposed, via a friction press fit, in the open distal end of the shape memory needle 34. From this first end, the suture material extends distally a short distance so as to pass through the slot 53 of the suture feed needle 52, and then, once through the slot 53, extends proximally along the outside of the suture feed needle 52.

The suture material extends along the outside of the suture feed needle 52 until it passes into and through the interior of the channel 55. The suture material then passes through an opening between the interior of the channel 55 and the interior of the handle 10 so as to enter the interior of the handle 10. Inside the handle, the suture material passes a first time through the generally straight tube 23 and the generally U-shaped tube 25, and is then formed into a loop within the handle 10 so as to pass through the generally straight tube 23 and the generally U-shaped tube 25 a second time. The looped end of the suture material is actuatable during assembly via an opening in the proximal end of the housing 10, allowing the loop to be pulled to maintain tension on the suture material when appropriate. The looped suture, upon passing through the generally straight tube 23 and the generally U-shaped tube 25 for the second time, is passed through an opening in a handle cap 58 (FIG. 105), where it is formed into a second pre-tied knot around a shaft 60 of a snare basket 62. The suture material is then passed from the second pre-tied knot, via an opening in the handle 10, back into the interior of the handle 10, where it is wound around the suture spool 29. The tension spring 33 provides sufficient resistance to prevent the suture material from inadvertently being released from the suture spool 29.

Figure 116:
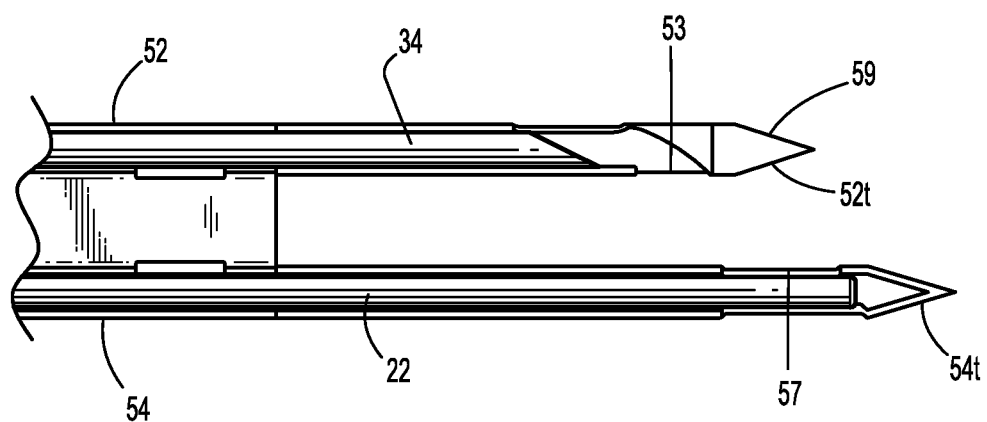
FIG. 116 is a top cross-sectional view of a distal end of the needle cartridge of FIG. 114.

When the apparatus 600 is used in a surgical procedure, the physician selects the apparatus 600 with a needle cartridge 50 having tips 52t, 54t having the desired directional orientation for the procedure to be performed. FIG. 116 illustrates the distal end of the meniscal repair device in its initial configuration. In the initial configuration, the shape memory needle 34 is positioned in its proximal most position relative to the distal end of the suture catch needle 54. The distal tip of the obturator 22 does not extend past the tip 54t of the suture catch needle 54. With the apparatus 600 in this initial configuration, the physician positions the apparatus 600 within the meniscus 5 by inserting tips 52t, 54t through the meniscus 5, as shown in FIG. 117, such that the meniscal wound is traversed by the suture feed needle 52 and the suture catch needle 54. In this position, the distal end of the suture feed needle 52 extends beyond the distal most surface of the meniscus 5, with the distal ends of the shape memory needle 34 and the ejector 44 being disposed adjacent to the distal most surface of the meniscus 5. Also, in this position, the suture catch needle 54, including the distal end of the obturator 22 disposed therein, extends beyond the distal most surface of the meniscus 5.

Once the physician has positioned the apparatus 600 as described above, the apparatus 600 is ready to be actuated. Specifically, the physician moves the thumbslide 16 distally relative to the handle 10, which moves the needle rack 32 distally within the handle 10. The distal movement of the needle rack 32 urges the shape memory needle 34, including the ejector wire 44 disposed therein, distally through the suture feed needle 52. At or near the same time, the distal movement of the nitinol needle rack 32 causes, by engagement of respective gear teeth thereof, rotation of the gear 17. Rotation of the gear 17 in turn causes the obturator rack 8, and the obturator 22 mounted thereto, to move proximally within the handle 10. Continued distal movement of the thumbslide 16 causes the shape memory needle 34 to move distally until its distal end extends through the opening of the slot 53 that is near the distal end of the suture feed needle 52. Due to its shape memory properties and the interaction between the shape memory needle 34 and the internal ramp 59, the shape memory needle 34 bends towards, and eventually through, the window 57 in the suture catch needle 54, as shown in FIG. 118, by passing through the slot 53.

Once the distal end of the shape memory needle 34 is positioned within the window 57, continued distal movement of the thumb slide 16 causes the ejector wire 44 to translate distally relative to the shape memory needle 34 and to eject the enlarged end in the first end of the suture material from the distal end of the shape memory needle 34. In this manner, the first end of the suture is positioned within the window 57 in the suture catch needle 54. During distal movement of the thumbslide 16, the obturator 22 continues to move proximally.

Thereafter, the physician moves the thumbslide 16 proximally relative to the handle 10, which retracts the shape memory needle 34 and the ejector wire 44 back into the suture feed needle 52. At or near the same time, the proximal movement of the thumbslide 16 relative to the handle 10 causes the obturator rack 8, and the obturator 22 mounted thereto, to move distally. The braided distal tip of the obturator 22 contacts the suture material near the enlarged end at the first end of the suture material and presses the suture material against the edges of the window 57, thereby frictionally securing the first end of the suture material in the window 57. Since the end of the suture catch needle 54 is closed, the distal tip of the obturator 22 cannot extend past the distal end of the suture catch needle 54. Once the suture material and the enlarged end at the first end of the suture material are secured within the window 57, the physician withdraws the apparatus 600 from the tissue, thereby drawing the length of suture material through the meniscus 5 to form a loop passing through the meniscus 5 and fully around the distal surface of the meniscus 5.

Figure 119:
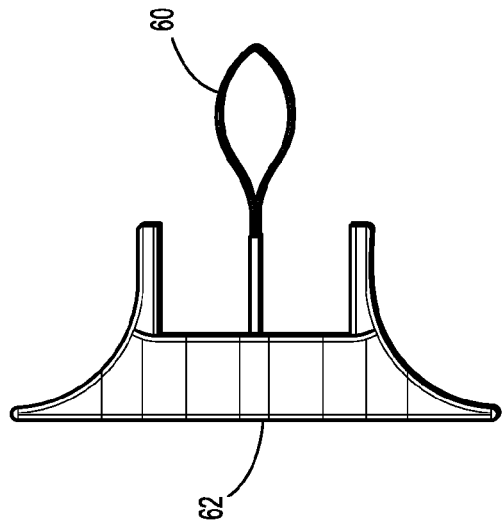
FIG. 119 is a top view of a snare basket.
Figure 120:
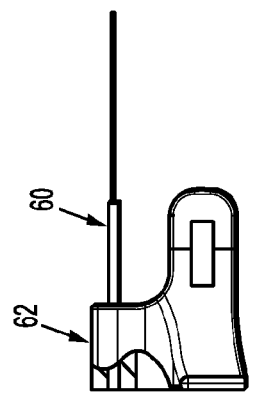
FIG. 120 is a front view of the snare basket of FIG. 119.

As set forth above, the suture material is formed into a second pre-tied knot at a mid-region along its length. Referring to FIGS. 119 and 120, this second pre-tied knot is initially tied around a shaft 60 of a snare basket 62. The shaft 60 of the snare basket 62 has, at its distal end, a collapsible loop. The snare basket 62 is detachably mounted to the distal end of the handle 10. Once the physician has withdrawn the apparatus 600 from the tissue T so as to form the suture loop around the meniscal tear, the physician removes the first end of the suture material from the window 57 of the suture catch needle 54, e.g., by cutting it. With the first end of the suture material thusly freed, the physician then feeds the first end of the suture material through the hoop at the distal end of the shaft 60 of the snare basket 62. The snare basket 62 is then detached from the handle 10, and the second pre-tied knot is pushed distally along the shaft 62 of the snare basket 62, collapsing the loop at the distal end thereof. In doing so, the second pre-tied knot is passed over the collapsed loop as well as over the first end of the suture material, thereby forming a suture knot that can be pushed distally, e.g., by a suture knot pusher device, until the knot is in a position adjacent to the meniscal tear. In this manner, the knot is tightened in order to approximate the torn meniscus 5. Additional manipulation of the knot, e.g., providing an additional hand-tied knot, may be performed by the physician, if desired, by extracting more suture material form the suture spool 29 and manipulating it along with the first end of the suture material into appropriate knot formations.

It will be appreciated that needles 105, 115, 205, 215, 305, 315, 405, 415, 52, 54, etc. may be straight (as shown) or curved as desired. Furthermore, the apparatus 100, 200, 300, 400, 500, 600 may be used with either a medial or lateral approach. Furthermore, it will be understood that the present disclosure is by no means limited to the particular constructions disclosed herein and/or shown in the drawings, but also comprises any modifications and/or equivalents within the scope of the disclosure. Other embodiments within the scope and spirit of the present disclosure will be apparent to those skilled in the art.

What is claimed is:

1. An apparatus for suturing tissue, comprising:
   a housing including a longitudinal axis and a distal end;
   an actuator slidably coupled to the housing along the longitudinal axis of the housing; and
   a needle assembly disposed at the distal end of the housing, the needle assembly including:
     a first needle including a lumen defined therein, and having first and second members disposed with the lumen, the first and second members being translatable through the lumen of the first needle; and
     a second needle including a lumen defined therein, and having a third member disposed within the lumen of the second needle,
     wherein distal movement of the actuator moves the first and second members distally through the first needle and simultaneously moves the third member proximally through the second needle.

2. The apparatus of claim 1, further comprising a length of suture material that is loaded into and retained within the first member.

3. The apparatus of claim 2, wherein the second member is adapted and configured to eject the length of suture material from within the first member.

4. The apparatus of claim 1, wherein the second needle further includes a window defined within an outer surface of the second needle, the window being adapted and configured to receive a length of suture therethrough.

5. The apparatus of claim 4, wherein the third member is adapted and configured to engage the length of suture and to frictionally secure the length of suture within the window.

6. The apparatus of claim 1, wherein the needle assembly is releasably secured to the distal end of the housing.

7. The apparatus of claim 1, wherein the first and second needle include distal ends that are adapted and configured to penetrate tissue.

8. The apparatus of claim 1, wherein the first needle is a suture feed needle.

9. The apparatus of claim 1, wherein the second needle is a suture catch needle.

10. The apparatus of claim 1, wherein the first member is a shape memory needle.

11. The apparatus of claim 1, wherein the second member is an ejector wire.

12. The apparatus of claim 1, wherein the third member is an obturator.

13. The apparatus of claim 1, wherein the first member is a shape memory needle, and the second member is an ejector wire, the ejector wire being disposed within the shape memory needle.

14. The apparatus of claim 1, wherein the second member is disposed within the first member, and the first member travels a first distance and the second member travels a second distance, the second distance being different from the first distance.

* * * * *